(12) United States Patent
Zion et al.

(10) Patent No.: US 9,095,623 B2
(45) Date of Patent: Aug. 4, 2015

(54) TERMINALLY-FUNCTIONALIZED CONJUGATES AND USES THEREOF

(71) Applicant: SmartCells, Inc., Whitehouse Station, NJ (US)

(72) Inventors: Todd C. Zion, Marblehead, MA (US); Thomas M. Lancaster, Stoneham, MA (US)

(73) Assignee: SMARTCELLS, INC., Whitehouse Station, NJ (US)

( * ) Notice: Subject to any disclaimer, the term of this patent is extended or adjusted under 35 U.S.C. 154(b) by 0 days.

(21) Appl. No.: 14/095,068

(22) Filed: Dec. 3, 2013

(65) Prior Publication Data

US 2014/0121159 A1     May 1, 2014

Related U.S. Application Data

(62) Division of application No. 13/257,454, filed as application No. PCT/US2010/022251 on Jan. 27, 2010, now Pat. No. 8,623,345.

(60) Provisional application No. 61/162,105, filed on Mar. 20, 2009, provisional application No. 61/162,058, filed on Mar. 20, 2009, provisional application No. 61/162,092, filed on Mar. 20, 2009.

(51) Int. Cl.
*A61K 39/12* (2006.01)
*A61K 47/48* (2006.01)
*A61K 38/28* (2006.01)

(52) U.S. Cl.
CPC ........... *A61K 47/48261* (2013.01); *A61K 38/28* (2013.01); *A61K 47/48176* (2013.01)

(58) Field of Classification Search
None
See application file for complete search history.

(56) References Cited

U.S. PATENT DOCUMENTS

| 6,410,053 | B1 * | 6/2002 | Taylor | 424/488 |
|---|---|---|---|---|
| 8,062,668 | B2 | 11/2011 | Ying et al. | |
| 2006/0019874 | A1 * | 1/2006 | Radhakrishnan et al. | 514/3 |
| 2010/0130726 | A1 | 5/2010 | Lancaster et al. | |
| 2011/0275560 | A1 | 11/2011 | Zion et al. | |
| 2011/0281791 | A1 | 11/2011 | Zion et al. | |
| 2011/0281792 | A1 | 11/2011 | Zion et al. | |
| 2011/0281939 | A1 | 11/2011 | Zion et al. | |
| 2011/0301083 | A1 | 12/2011 | Zion et al. | |
| 2012/0046223 | A1 | 2/2012 | Zion et al. | |

* cited by examiner

*Primary Examiner* — Susan Tran
(74) *Attorney, Agent, or Firm* — Immac J. Thampoe; John David Reilly

(57) ABSTRACT

The present disclosure provides inter alia conjugates of formula (I):

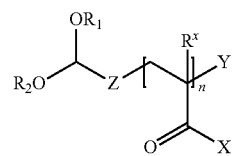

wherein n, $R_1$, $R_2$, $R^x$, Z, X, Y and Z are as defined herein. A conjugate of formula (I) can also be converted to a conjugate of formulae (II) or (III) as described herein. Without limitation, the conjugates can be used to make controlled release materials and chemical sensors.

13 Claims, 11 Drawing Sheets

SEQUENCE LISTING

```
<160> NUMBER OF SEQ ID NOS: 2

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```

TERMINALLY-FUNCTIONALIZED CONJUGATES AND USES THEREOF

RELATED APPLICATIONS

This application claims priority to U.S. Ser. No. 13/257,454 filed Sep. 19, 2011, which claims priority to International Application No. PCT/US2010/022251, filed Jan. 27, 2010, which claims benefit of U.S. Provisional Application No. 61/162,105 filed Mar. 20, 2009, U.S. Provisional Application No. 61/162,058 filed Mar. 20, 2009, and U.S. Provisional Application No. 61/162,092 filed Mar. 20, 2009, the content of each of which is hereby incorporated by reference in its entirety.

REFERENCE TO SEQUENCE LISTING SUBMITTED ELECTRONICALLY

The sequence listing of the present application is submitted electronically via EFS-Web as an ASCII formatted sequence listing with a file name "23031USDIV-SEQTXT-15NOV2013.txt", creation date of Nov. 15, 2013 and a size of 1 KB. This sequence listing submitted via EFS-Web is part of the specification and is herein incorporated by reference in its entirety.

BACKGROUND

The majority of "controlled-release" drug delivery systems known in the prior art (e.g., U.S. Pat. No. 4,145,410 to Sears which describes drug release from capsules which are enzymatically labile) are incapable of releasing drugs at intervals and concentrations which are in direct proportion to the amount of a molecular indicator (e.g., a metabolite) present in the human body. The delivery or release of drug in these prior art systems is thus not literally "controlled," but simply a slow release which is independent of external or internal factors.

The treatment of diabetes mellitus with injectable insulin is a well-known and studied example where uncontrolled, slow release of insulin is undesirable. In fact, it is apparent that the simple replacement of the hormone is not sufficient to prevent the pathological sequelae associated with this disease. The development of these sequelae is believed to reflect an inability to provide exogenous insulin proportional to varying blood glucose concentrations experienced by the patient. To solve this problem several biological and bioengineering approaches to develop a more physiological insulin delivery system have been suggested (e.g., see U.S. Pat. No. 4,348,387 to Brownlee et al.; U.S. Pat. Nos. 5,830,506, 5,902,603, and 6,410,053 to Taylor et al. and U.S. Patent Application Publication No. 2004-0202719 to Zion et al.).

In certain embodiments of the Zion system, multivalent glucose-binding molecules (e.g., lectins) are combined with a glycosylated polymer-insulin conjugate. The glycosylated polymer contains multiple saccharide binding groups and forms an insoluble cross-linked material in the presence of the glucose-binding molecule. The material releases the glycosylated polymer-insulin conjugate in response to increases in glucose concentration. In general, these systems have so far relied on high molecular weight carbohydrate structures that are based on natural carbohydrates such as dextran and glycogen. As discussed below, while these high molecular weight natural carbohydrates are useful, they present certain difficulties and there is therefore a need in the art for alternative conjugates with novel properties and functionalities.

SUMMARY

In one aspect, the present disclosure provides conjugates of formula (I):

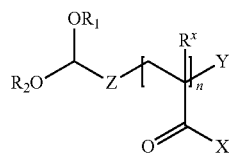

(I)

wherein n, $R_1$, $R_2$, $R^x$, Z, X, Y and Z are as defined herein. In particular at least two occurrence of X include an affinity ligand, e.g., a saccharide.

Conjugates of formula (I) are useful as intermediates in the preparation of other conjugates, e.g., conjugates of formulae (II) and/or (III):

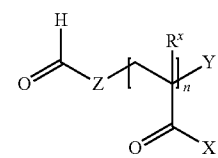

(II)

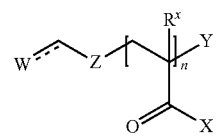

(III)

wherein -----, n, $R_1$, $R_2$, $R^x$, Z, W, X, Y and Z are as defined herein.

The present disclosure also provides methods of preparing conjugates of formulae (I), (II) and (III). For example, a terminal-group functionality, such as the acetal functionality as provided in formula (I), may be converted, through methods known to those skilled in the art, into an aldehyde functionality to provide a conjugate of formula (II). In certain embodiments, such a conjugate, so converted, can then be covalently conjugated to a drug (W) to form a terminally functionalized polymerdrug conjugate of formula (III). In certain embodiments, these terminally functionalized polymerdrug conjugates have greater retention of in vivo bioactivity versus more randomly functionalized polymerdrug conjugates (i.e., wherein the drug is randomly located at various positions along the polymer chain). The use of conjugates that include a detectable label (W) instead of a drug, e.g., in chemical sensors is also described.

In one aspect, conjugates can be used to produce cross-linked materials that are capable of controllably releasing the conjugates in response to a target molecule (e.g., glucose). These materials are prepared by combining the conjugates with multivalent cross-linking agents that non-covalently bind the affinity ligands of the conjugates and thereby cross-link the conjugates to form the cross-linked material. The non-covalent bonds between the multivalent cross-linking agents and the affinity ligands are competitively dissociated in the presence of excess amounts of the target molecule.

DEFINITIONS

Definitions of specific functional groups, chemical terms, and general terms used throughout the specification are described in more detail below. For purposes of this invention, the chemical elements are identified in accordance with the Periodic Table of the Elements, CAS version, Handbook of Chemistry and Physics, 75$^{th}$ Ed inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987.

Certain polymers, as described herein may have one or more double bonds that can exist as either the Z or E isomer, unless otherwise indicated. The invention additionally encompasses polymers as individual isomers substantially free of other isomers and alternatively, as mixtures of various isomers, e.g., racemic mixtures of stereoisomers. In addition to the above-mentioned polymers per se, this invention also encompasses pharmaceutically acceptable derivatives of these polymers and compositions comprising one or more of these polymers.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes an optionally substituted hydrocarbon moiety that may be straight-chain (i.e., unbranched), branched, or cyclic ("carbocyclic") and may be completely saturated or may contain one or more units of unsaturation, but which is not aromatic. Unless otherwise specified, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "unsaturated", as used herein, means that a moiety has one or more double or triple bonds.

The terms "cycloaliphatic", "carbocycle", or "carbocyclic", used alone or as part of a larger moiety, refer to an optionally substituted saturated or partially unsaturated cyclic aliphatic monocyclic or bicyclic ring systems, as described herein, having from 3 to 10 members. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons.

The term "alkyl," as used herein, refers to optionally substituted saturated, straight or branched-chain hydrocarbon radicals derived from an aliphatic moiety containing between 1-6 carbon atoms by removal of a single hydrogen atom. In some embodiments, the alkyl group employed in the invention contains 1-5 carbon atoms. In another embodiment, the alkyl group employed contains 1-4 carbon atoms. In still other embodiments, the alkyl group contains 1-3 carbon atoms. In yet another embodiments, the alkyl group contains 1-2 carbons. Examples of alkyl radicals include, but are not limited to, methyl, ethyl, n-propyl, isopropyl, n-butyl, isobutyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes an optionally substituted monovalent group derived from a straight- or branched-chain aliphatic moiety having at least one carbon-carbon double bond by the removal of a single hydrogen atom. In certain embodiments, the alkenyl group employed in the invention contains 2-6 carbon atoms. In certain embodiments, the alkenyl group employed in the invention contains 2-5 carbon atoms. In some embodiments, the alkenyl group employed in the invention contains 2-4 carbon atoms. In another embodiment, the alkenyl group employed contains 2-3 carbon atoms. Alkenyl groups include, for example, ethenyl, propenyl, butenyl, 1-methyl-2-buten-1-yl, and the like.

The term "alkynyl," as used herein, refers to an optionally substituted monovalent group derived from a straight or branched-chain aliphatic moiety having at least one carbon-carbon triple bond by the removal of a single hydrogen atom. In certain embodiments, the alkynyl group employed in the invention contains 2-6 carbon atoms. In certain embodiments, the alkynyl group employed in the invention contains 2-5 carbon atoms. In some embodiments, the alkynyl group employed in the invention contains 2-4 carbon atoms. In another embodiment, the alkynyl group employed contains 2-3 carbon atoms. Representative alkynyl groups include, but are not limited to, ethynyl, 2-propynyl (propargyl), 1-propynyl, and the like.

The term "aryl" used alone or as part of a larger moiety as in "aralkyl", "aralkoxy", or "aryloxyalkyl", refers to an optionally substituted monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present disclosure, "aryl" refers to an aromatic ring system which includes, but not limited to, phenyl, biphenyl, naphthyl, anthracyl and the like, which may bear one or more substituents.

The term "arylene" refers to a bivalent aryl group as defined herein.

The terms "heteroaryl" used alone or as part of a larger moiety, e.g., "heteroaralkyl", or "heteroaralkoxy", refer to optionally substituted groups having 5 to 10 ring atoms, preferably 5, 6, or 9 ring atoms; having 6, 10, or 14π it electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, carbocyclic, or heterocyclic rings, where the radical or point of attachment is on the heteroaromatic ring. Non limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

The term "heteroarylene" refers to a bivalent heteroaryl group as defined herein.

The term "heteroaliphatic" or "heteroaliphatic group", as used herein, denotes an optionally substituted hydrocarbon moiety having, in addition to carbon atoms, from one to five heteroatoms, that may be straight-chain (i.e., unbranched), branched, or cyclic ("heterocyclic") and may be completely saturated or may contain one or more units of unsaturation, but which is not aromatic. The term "heteroatom" refers to nitrogen, oxygen, or sulfur, and includes any oxidized form of nitrogen or sulfur, and any quaternized form of a basic nitrogen. The term "nitrogen" also includes a substituted nitrogen. Unless otherwise specified, heteroaliphatic groups contain 1-6 carbon atoms wherein 1-3 carbon atoms are optionally and independently replaced with heteroatoms selected from oxygen, nitrogen and sulfur. In some embodiments, heteroaliphatic groups contain 1-4 carbon atoms, wherein 1-2 carbon atoms are optionally and independently replaced with heteroatoms selected from oxygen, nitrogen and sulfur. In yet other embodiments, heteroaliphatic groups contain 1-3 carbon atoms, wherein 1 carbon atom is optionally and independently replaced with a heteroatom selected from oxygen, nitrogen and sulfur. Suitable heteroaliphatic groups include, but are not limited to, linear or branched, heteroalkyl, heteroalkenyl, and heteroalkynyl groups.

As used herein, the terms "heterocycle", "heterocyclyl", "heterocyclic radical", and "heterocyclic ring" are used interchangeably and refer to a stable optionally substituted 5- to 7-membered monocyclic or 7-10-membered bicyclic heterocyclic moiety that is either saturated or partially unsaturated, and having, in addition to carbon atoms, one or more heteroatoms, as defined above. The term "nitrogen" includes a substituted nitrogen. A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or carbocyclic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

The term "bivalent hydrocarbon chain" (also referred to as a "bivalent alkylene group") is a polymethylene group, i.e., $—(CH_2)_z—$, wherein z is a positive integer from 1 to 10, from 1 to 8, from 1 to 6, from 1 to 4, from 1 to 3, from 1 to 2, from 2 to 10, from 2 to 8, from 2 to 6, from 2 to 4, or from 2 to 3. A substituted bivalent hydrocarbon chain is a polymethylene group in which one or more methylene hydrogen atoms are replaced with a substituent. Suitable substituents include those described below for a substituted aliphatic group.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $—(CH_2)_{0-4}R^\circ$; $—(CH_2)_{0-4}OR^\circ$; $—O—(CH_2)_{0-4}$ $—C(O)OR^\circ$; $—(CH_2)_{0-4}CH(OR^\circ)_2$; $—(CH_2)_{0-4}SR^\circ$; $(CH_2)_{0-4}Ph$, which may be substituted with $R^\circ$; $—(CH_2)_{0-4}$ $O(CH_2)_{0-1}Ph$ which may be substituted with $R^\circ$; $—CH=CHPh$, which may be substituted with $R^\circ$; $—NO_2$; $—CN$; $—N_3$; $—(CH_2)_{0-4}N(R^\circ)_2$; $—(CH_2)_{0-4}N(R^\circ)C(O)$ $R^\circ$; $—N(R^\circ)C(S)R^\circ$; $—(CH_2)_{0-4}—N(R^\circ)C(O)NR^\circ_2$; $—N(R^\circ)C(S)NR^\circ_2$; $—(CH_2)_{0-4}N(R^\circ)C(O)OR^\circ$; $—N(R^\circ)N(R^\circ)C(O)R^\circ$; $—N(R^\circ)N(R^\circ)C(O)NR^\circ_2$; $—N(R^\circ)N(R^\circ)C(O)OR^\circ$; $—(CH_2)_{0-4}C(O)R^\circ$; $C(S)R^\circ$; $—(CH_2)_{0-4}C(O)OR^\circ$; $—(CH_2)_{0-4}C(O)SR^\circ$; $—(CH_2)_{0-4}C(O)OSiR^\circ_3$; $—(CH_2)_{0-4}OC(O)R^\circ$; $—OC(O)(CH_2)_{0-4}$ $SR—$, $SC(S)SR^\circ$; $—(CH_2)_{0-4}SC(O)R^\circ$; $—(CH_2)_{0-4}C(O)$ $NR^\circ_2$; $—C(S)NR^\circ_2$; $—C(S)SR^\circ$; $—SC(S)SR^\circ$, $—(CH_2)_{0-4}OC(O)NR^\circ_2$; $—C(O)N(OR^\circ)R^\circ$; $—C(O)C(O)$ $R^\circ$; $—C(O)CH_2C(O)R^\circ$; $—C(NOR^\circ)R^\circ$; $—(CH_2)_{0-4}$ $SSR^\circ$; $—(CH_2)_{0-4}S(O)_2R^\circ$; $—(CH_2)_{0-4}S(O)_2OR^\circ$; $—(CH_2)_{0-4}OS(O)_2R^\circ$; $—S(O)_2NR^\circ_2$; $—(CH_2)_{0-4}S(O)R^\circ$; $—N(R^\circ)S(O)_2NR^\circ_2$; $—N(R^\circ)S(O)_2R^\circ$; $—N(OR^\circ)R^\circ$; $—C(NH)NR^\circ_2$; $—P(O)_2R^\circ$; $P(O)R^\circ_2$; $—OP(O)R^\circ_2$; $—OP(O)(OR^\circ)_2$; $SiR^\circ_3$; $—(C_{1-4}$ straight or branched)alkylene)O—N(R^\circ)_2$; or $—(C_{1-4}$ straight or branched)alkylene) $C(O)O—N(R^\circ)_2$, wherein each $R^\circ$ may be substituted as defined below and is independently hydrogen, $C_{1-6}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $—(CH_2)_{0-2}R^\bullet$, $-(haloR^\bullet)$, $—(CH_2)_{0-2}OH$, $—(CH_2)_{0-2}OR^\bullet$, $—(CH_2)_{0-2}CH(OR^\bullet)_2$; $—O(haloR^\bullet)$, $—CN$, $—N_3$, $—(CH_2)_{0-2}C(O)R^\bullet$, $—(CH_2)_{0-2}C(O)OH$, $—(CH_2)_{0-2}C(O)OR^\bullet$, $—(CH_2)_{0-2}SR^\bullet$, $—(CH_2)_{0-2}SH$, $—(CH_2)_{0-2}NH_2$, $—(CH_2)_{0-2}NHR^\bullet$, $—(CH_2)_{0-2}NR^\bullet_2$, $—NO_2$, $—SiR^\bullet_3$, $—OSiR^\bullet_3$, $—C(O)SR^\bullet$, $—(C_{1-4}$ straight or branched alkylene)C(O)OR^\bullet$, or $—SSR^\bullet$ wherein each $R^\bullet$ is unsubstituted or where preceded by "halo" is substituted only with one or more halogens, and is independently selected from $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_1$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

A "suitable amino-protecting group," as used herein, is well known in the art and includes those described in detail in *Protecting Groups in Organic Synthesis*, T. W. Greene and P. G. M. Wuts, 3$^{rd}$ edition, John Wiley & Sons, 1999. Suitable amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3- pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl(pentacarbonylchromium- or tungsten) carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

A "suitable hydroxyl protecting group" as used herein, is well known in the art and includes those described in detail in *Protecting Groups in Organic Synthesis*, T. W. Greene and P. G. M. Wuts, 3$^{rd}$ edition, John Wiley & Sons, 1999. Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri (p-methoxyphenyl)methyl, 4-(4'-bromophenacyloxyphenyl) diphenylmethyl, 4,4',4"-tris(4,5-dichlorophthalimidophenyl) methyl, 4,4',4"-tris(levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1, 3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N, N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

Agglutinated—When two or more cells are "agglutinated" by a cross-linking agent as described herein, they are each physically associated with the cross-linking agent in a cell-agent-cell complex. Typically, agglutination only occurs once the cross-linking agent concentration reaches a threshold concentration. This concentration is referred to as the minimum agglutination concentration (MAC). The MAC for a given cross-linking agent is commonly measured using a spectrophotometric plate reader that can quantify changes in solution absorbance.

Aptamer—As used herein, the term "aptamer" refers to a polynucleotide or polypeptide that binds specifically to a target molecule. In general, an aptamer is said to "bind specifically" to its target molecule if it associates at a detectable level with the target molecule and does not associate detectably with unrelated molecular entities (e.g., molecules which share no common structural features with the target molecule) under similar conditions. Specific association between a target molecule and an aptamer will typically be dependent upon the presence of a particular structural feature of the target molecule such as an epitope recognized by the aptamer. Generally, if an aptamer is specific for epitope A, the presence of a molecule containing epitope A or the presence of free unlabeled epitope A in a reaction containing both free labeled epitope A and the aptamer thereto, will reduce the amount of labeled epitope A that binds to the aptamer. In general, it is to be understood that specificity need not be absolute. Indeed, it is well known in the art that aptamers may cross-react with other epitopes in addition to the target epitope. Such cross-reactivity may be acceptable depending upon the application for which the aptamer is to be used. Thus the degree of specificity of an aptamer will depend on the context in which it is being used. It is also to be understood that specificity may be evaluated in the context of additional factors such as the affinity of the aptamer for the target molecule versus the affinity of the aptamer for non-target molecules.

Associated—As used herein, two entities are physically "associated" with one another when they are bound by direct non-covalent interactions. Desirable non-covalent interactions include those of the type which occur between an immunoglobulin molecule and an antigen for which the immunoglobulin is specific, for example, ionic interactions, hydrogen bonds, van der Waals interactions, hydrophobic interactions, etc. The strength, or affinity of the physical association can be expressed in terms of the dissociation constant ($K_d$) of the interaction, wherein a smaller $K_d$ represents a greater affinity. For example, the association properties of a selected cross-linking agent and target molecule can be quantified using methods well known in the art.

Biomolecule—As used herein, the term "biomolecule" refers to molecules (e.g., polypeptides, amino acids, polynucleotides, nucleotides, polysaccharides, sugars, lipids, nucleoproteins, glycoproteins, lipoproteins, steroids, metabolites, etc.) whether naturally-occurring or artificially created (e.g., by synthetic or recombinant methods) that are commonly found in cells and tissues. Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

Drug—As used herein, the term "drug" refers to small molecules or biomolecules that alter, inhibit, activate, or otherwise affect a biological event. For example, drugs may include, but are not limited to, anti-AIDS substances, anti-cancer substances, antibiotics, anti-diabetic substances, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anti-coagulants and/or anti-thrombotic agents, local anesthetics, ophthalmics, prostaglandins, anti-depressants, anti-psychotic substances, anti-emetics, and imaging agents. A more complete listing of exemplary drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 1996, and the United States Pharmacopeia-25/National formulary-20, published by the United States Pharmcopeial Convention, Inc., Rockville Md., 2001. Preferably, though not necessarily, the drug is one that has already been deemed safe and effective for use by the appropriate governmental agency or body. For example, drugs for human use listed by the FDA under 21 C.F.R. §§330.5, 331 through 361, and 440 through 460; drugs for veterinary use listed by the FDA under 21 C.F.R. §§500 through 589, are all considered acceptable for use in accordance with the present invention.

Hyperbranched—As used herein, a "hyperbranched" structure is a covalent structure that includes at least one branched branch (e.g., a dendrimeric structure). A hyperbranched structure may include polymeric and/or non-polymeric sub-structures.

Lectin—As used herein, a "lectin" is a protein that binds with specificity to saccharides and polysaccharides. A lectin can be of any origin (e.g., plant, animal or other). In certain embodiments a lectin can be isolated from a natural source. In other embodiments a lectin can be produced synthetically or recombinantly. A lectin can be composed of one or more subunits under physiological conditions. In preferred embodiments a lectin is composed of two or more subunits under physiological conditions (e.g., four subunits). The subunits may be the same or different.

Physiological conditions—As used herein, "physiological conditions" are those conditions that are found in the arterial blood of a typical patient. Generally, the patient is a mammal, e.g., a human, dog, cat, mouse, etc. In human patients, the pH under physiological conditions is typically between about 7.35 and about 7.45 (preferably about 7.40). Human physiological temperatures range from about 36.4 to about 37.4 C (preferably about 36.9 C).

Polymer—As used herein, a "polymer" or "polymeric structure" is a structure that includes a string of covalently bound monomers. A polymer can be made from one type of monomer or more than one type of monomer. The term "polymer" therefore encompasses copolymers, including block-copolymers in which different types of monomer are grouped separately within the overall polymer. A polymer can be linear or branched.

Polynucleotide—As used herein, a "polynucleotide" is a polymer of nucleotides. The terms "polynucleotide", "nucleic acid", and "oligonucleotide" may be used interchangeably. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynylcytidine, C5-methylcytidine, 7-deazaadenosine, 7-deazaguanosine, 8-oxoadenosine, 8-oxoguanosine, O(6)-methylguanine, 4-acetylcytidine, 5-(carboxyhydroxymethyl) uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2'-O-methylcytidine, arabinose, and hexose), or modified phosphate groups (e.g., phosphorothioates and 5'-N-phosphoramidite linkages).

Polypeptide—As used herein, a "polypeptide" is a polymer of amino acids. The terms "polypeptide", "protein", "oligopeptide", and "peptide" may be used interchangeably. Polypeptides may contain natural amino acids, non-natural amino acids (i.e., compounds that do not occur in nature but that can be incorporated into a polypeptide chain) and/or amino acid analogs as are known in the art. Also, one or more of the amino acid residues in a polypeptide may be modified, for example, by the addition of a chemical entity such as a carbohydrate group, a phosphate group, a farnesyl group, an isofarnesyl group, a fatty acid group, a linker for conjugation, functionalization, or other modification, etc. These modifications may include cyclization of the peptide, the incorporation of D-amino acids, etc.

Polysaccharide—As used herein, a "polysaccharide" is a polymer of saccharides. The terms "polysaccharide", "carbohydrate", and "oligosaccharide", may be used interchangeably. The polymer may include natural saccharides (e.g., arabinose, lyxose, ribose, xylose, ribulose, xylulose, allose, altrose, galactose, glucose, gulose, idose, mannose, talose, fructose, psicose, sorbose, tagatose, mannoheptulose, sedoheptulose, octolose, and sialose) and/or modified saccharides (e.g., 2'-fluororibose, 2'-deoxyribose, and hexose). Exemplary disaccharides include sucrose, lactose, maltose, trehalose, gentiobiose, isomaltose, kojibiose, laminaribiose, mannobiose, melibiose, nigerose, rutinose, and xylobiose.

Small molecule—As used herein, the term "small molecule" refers to molecules, whether naturally-occurring or artificially created (e.g., via chemical synthesis), that have a relatively low molecular weight. Typically, small molecules are monomeric and have a molecular weight of less than about 1,500 Da.

Treat—As used herein, the term "treat" (or "treating", "treated", "treatment", etc.) refers to the administration of a material of the present disclosure to a subject in need thereof with the purpose to alleviate, relieve, alter, ameliorate, improve or affect a condition (e.g., diabetes), a symptom or symptoms of a condition (e.g., hyperglycemia), or the predisposition toward a condition.

DETAILED DESCRIPTION OF VARIOUS EMBODIMENTS

Figure 1:
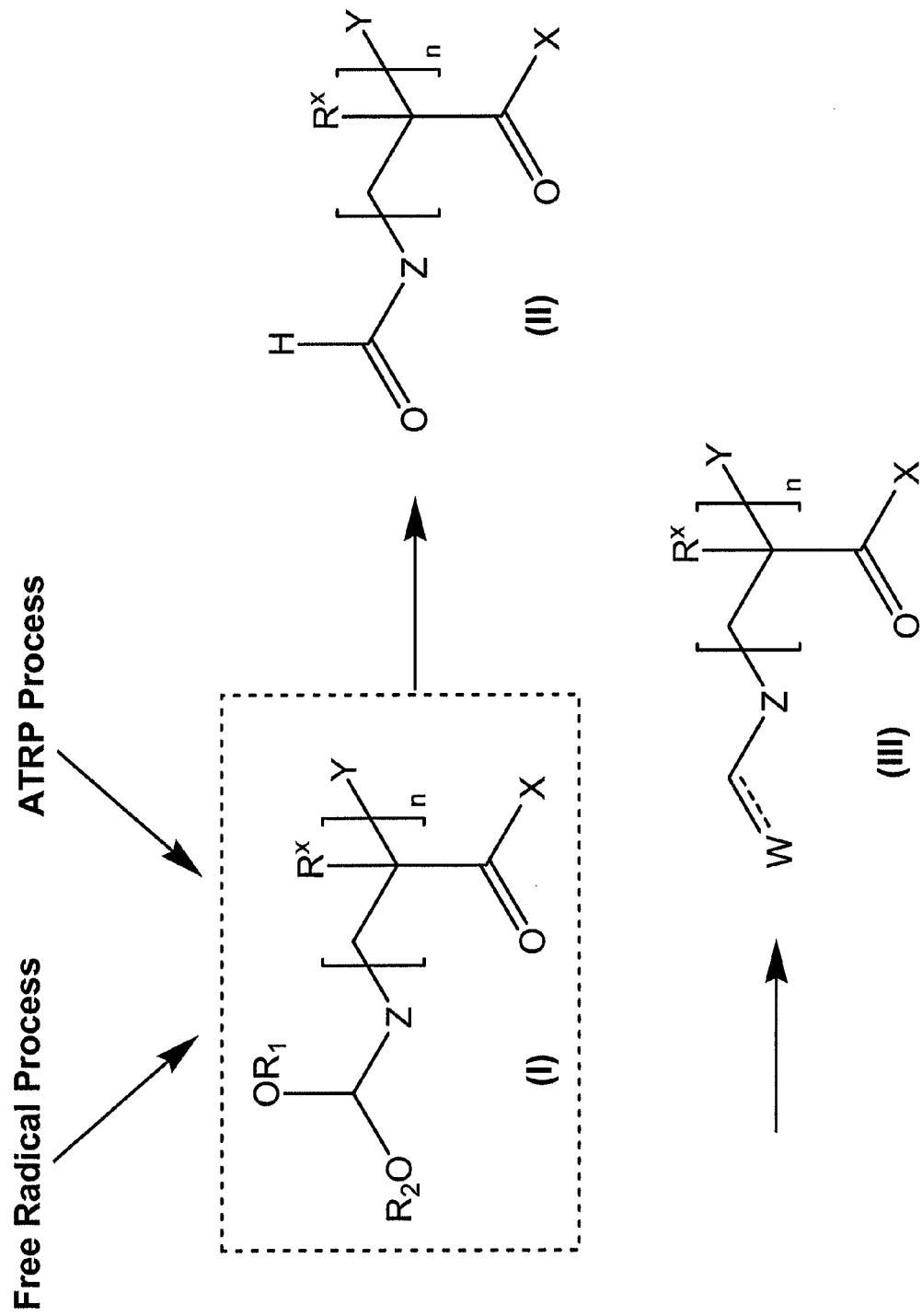
FIG. 1: is a schematic which shows the synthesis of conjugates of formula (I) via an Atom Transfer Radical Polymerization (ATRP) process or a Free Radical-Chain Transfer Process. The conjugate of formulae (II) is prepared from the conjugate of formula (I), in part, by removal of the acetal group. The conjugate of formula (III) is prepared from the conjugate of formula (II) by covalent conjugation of a drug via the aldehyde moiety.

This application refers to a number of documents including patent and non-patent documents. The entirety of each of these documents is incorporated herein by reference.

Whether used to deliver insulin or other drugs, the glycosylated polymer conjugates used in existing Zion conjugates present certain difficulties. Indeed, as a result of the high molecular weight (MW) of the glycosylated polymers, the conjugates have a much higher MW than the native drug. The conjugate is therefore absorbed into the systemic circulation more slowly. In addition, once in the circulation, the intrinsic bioactivity of the conjugate may be reduced and the rate of elimination may be slower. In US 2007/0099820 to Lancaster et al., we described one solution to this problem which involved attaching the drug to a polymer which is enzymatically degraded at the site of administration. While these enzymatically degradable conjugates behaved more like unconjugated insulin once released from the Zion system, we have found that they can suffer from two main disadvantages, namely: an inherent difficulty in manufacturing large quantities of pharmaceutical grade material and unwanted degradation due to enzyme activity in certain species even in the absence of target molecule.

For example, the exemplary glycogen-based conjugates of Lancaster were derived from animal and plant sources with broad and variable MW distributions and residual foreign protein content that required removal prior to insulin conjugation. Each separate lot and type of glycogen had to be subjected to MW fractionation to center and reduce the polydispersity of the distribution leading to substantially increased production costs and corresponding yield losses. Furthermore, each glycogen chain was modified with a variable number of sugar affinity ligands leading to not only a distribution of chain lengths but also a distribution of affinity ligands across those different chain lengths.

As described in the Examples, we also discovered rather unexpectedly that different animal species can possess unique levels of conjugate-degrading enzyme activity. In the case of rats, for example, the amylase activity was enough to render free glycogen conjugates bioactive but low enough to cause only marginal degradation of cross-linked conjugate. In pigs, however, the activity was high enough to cause rapid in vivo degradation of cross-linked conjugates thereby leading to large amounts of insulin release even in the absence of glucose. These results meant that the degradability of conjugates would likely need to be designed specifically for each animal species in order to balance conjugate bioactivity with unwanted degradation of cross-linked conjugates. From a pharmaceutical development perspective, regulatory agencies usually require safety data on the same formulation in two animal species prior to initiating human clinical trials. However, due to species differences in enzyme degradability the pharmacokinetics would likely differ in each of the two species.

There is therefore a need in the art for conjugates that can function within a Zion system without being susceptible to enzymatic degradation. Ideally such conjugates would also be synthetic, well-characterized molecular entities that do not suffer from the production challenges encountered with polymeric natural products. We hypothesized that suitable non-biodegradable conjugates would need to be of low molecular weight in order to exhibit similar pharmacokinetic (PK) and pharmacodynamic (PD) properties to the unconjugated drug. However, we were also aware that previous studies with the Zion system (US 2004/0202719 and "Glucose-responsive materials for self-regulated insulin delivery", Thesis, Massachusetts Institute of Technology, Dept. of Chemical Engineering, 2004) had shown that the ability of conjugates to self-assemble into insoluble cross-linked materials is eliminated as the molecular weight of conjugates is decreased. In order to overcome this problem we developed new families of higher affinity ligands than previously used for these types of applications. In parallel, we developed low molecular weight frameworks to which we chemically attached these ligands in a multivalent fashion with a range of linker arm lengths and chemistries. Unexpectedly, we have found that certain high affinity ligands when conjugated to appropriate frameworks that are low enough in molecular weight to preserve conjugate bioactivity are also capable of forming insoluble cross-linked materials when combined with suitable multivalent cross-linking agents. As discussed in more detail below, we have also shown that the resulting materials can be designed to release conjugates in the presence of varying concentrations of target molecule.

Conjugates

In one aspect, the present disclosure provides conjugates that include two or more separate affinity ligands covalently bound to a polymeric framework. In general, the affinity ligands are capable of competing with a target molecule for binding with a multivalent cross-linking agent. In certain embodiments, the conjugates have low polydispersity, e.g., less than 1.5, or less than 1.25. Depending on the end application, the conjugates may also include a drug and/or a detectable label. As discussed in more detail below, the affinity ligands, drug, and/or detectable label are covalently attached to the conjugate framework. In certain embodiments the conjugate framework (i.e., without including the affinity ligands, drug or detectable label) has a molecular weight of less than 10,000 Da, e.g., in the range of about 100 to about 10,000 Da. In certain embodiments, the conjugate framework has a molecular weight in the range of about 300 to about 5,000 Da. In certain embodiments, the conjugate framework has a molecular weight in the range of about 500 to about 2,500 Da. In certain embodiments, the conjugate framework has a molecular weight in the range of about 1,000 to 2,000 Da. In certain embodiments, the conjugate framework has a molecular weight in the range of about 200 to 1,000 Da. In certain embodiments, the conjugate framework has a molecular weight in the range of about 300 to 800 Da.

1. General Description of Conjugates

In one aspect, the present disclosure provides conjugates of formula (I):

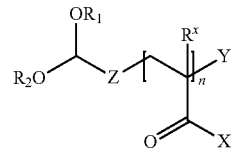

I wherein:

$R_1$ and $R_2$ are independently selected from the group consisting of optionally substituted aliphatic, optionally substituted heteroaliphatic, optionally substituted aryl, or optionally substituted heteroaryl;

$R^x$ is hydrogen or optionally substituted $C_{1-6}$ alkyl;

Z is an optionally substituted bivalent $C_{1-10}$ hydrocarbon chain, wherein 1, 2, 3, 4 or 5 methylene units of Z are optionally and independently replaced with one or more groups selected from —S—, —O—, —$NR^a$—, —(C=$NR^a$)—, —(C=O)—, —(S=O)—, —S(=O)$_2$—, —(C$R^b$=C$R^b$), —(N=N)—, an optionally substituted arylene moiety or an optionally substituted heteroarylene moiety, wherein $R^a$ is hydrogen, optionally substituted aliphatic, optionally substituted heteroaliphatic, optionally substituted aryl, optionally substituted heteroaryl, or a suitable amino protecting group; and $R^b$ is hydrogen, optionally substituted aliphatic, optionally substituted heteroaliphatic, optionally substituted aryl, optionally substituted heteroaryl;

each instance of X is independently —$OR^c$ or —N($R^d$)$_2$, wherein $R^c$ is hydrogen, optionally substituted aliphatic, optionally substituted heteroaliphatic, optionally substituted aryl, optionally substituted heteroaryl, a suitable hydroxyl protecting group, a cation group, or an affinity ligand, and each $R^d$ is, independently, hydrogen, optionally substituted aliphatic, optionally substituted heteroaliphatic, optionally substituted aryl, optionally substituted heteroaryl, a suitable amino protecting group, or an affinity ligand, wherein at least two occurrences of X include an affinity ligand;

Y is hydrogen, halogen, optionally substituted aliphatic, optionally substituted heteroaliphatic, optionally substituted aryl, optionally substituted heteroaryl, —$OR^e$ or —$SR^e$ wherein $R^e$ is hydrogen, optionally substituted aliphatic, optionally substituted heteroaliphatic, optionally substituted aryl, or optionally substituted heteroaryl; and n is an integer between 5-25, inclusive.

These conjugates are useful as intermediates in the preparation of other conjugates, such as, for example, conjugates of formulae (II) and/or (III):

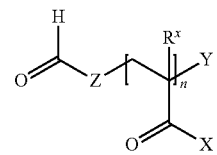

II

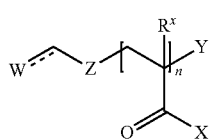

wherein $R^x$, X, Y, Z and n are as defined above and herein;
W is a covalently conjugated drug or detectable label;
and ----- corresponds to a single or double bond.

2. Description of Exemplary Groups i. $R_1$ and $R_2$

As defined generally above, $R_1$ and $R_2$ are independently selected from the group consisting of optionally substituted aliphatic, optionally substituted heteroaliphatic, optionally substituted aryl, or optionally substituted heteroaryl. In certain embodiments $R_1$ and $R_2$ are the same.

In certain embodiments, $R_1$ and $R_2$ are optionally substituted aliphatic. In certain embodiments, $R_1$ and $R_2$ are optionally substituted alkyl. In certain embodiments, $R_1$ and $R_2$ are, independently, an optionally substituted methyl, ethyl, n-propyl, isopropyl, n-butyl, isobutyl, sec-butyl, or tert-butyl group. In certain embodiments, $R_1$ and $R_2$ are, independently, an optionally substituted methyl or ethyl group. In certain embodiments, $R_1$ and $R_2$ are both methyl. In certain embodiments, $R_1$ and $R_2$ are both ethyl.

ii. $R^x$

As defined generally above, $R^x$ is hydrogen or optionally substituted $C_{1-6}$ alkyl.

In certain embodiments, $R^x$ is hydrogen. In certain embodiments, $R^x$ is optionally substituted $C_{1-6}$ alkyl. In certain embodiments, $R^x$ is optionally substituted $C_{1-3}$ alkyl. In certain embodiments, $R^x$ is optionally substituted methyl. In certain embodiments, $R^x$ is —$CH_3$.

iii. Z

As defined generally above, Z is a bivalent $C_{1-10}$ hydrocarbon chain, wherein 1, 2, 3, 4 or 5 methylene units of Z are optionally and independently replaced with one or more groups selected from —S—, —O—, —$NR^a$—, —(C=$NR^a$)—, —(C=O)—, —(S=O)—, —S(=O)$_2$—, —($CR^b$=$CR^b$)—, —(N=N)—, an optionally substituted arylene moiety or an optionally substituted heteroarylene moiety, wherein $R^a$ is hydrogen, optionally substituted aliphatic, optionally substituted heteroaliphatic, optionally substituted aryl, optionally substituted heteroaryl, or a suitable amino protecting group; and $R^b$ is hydrogen, optionally substituted aliphatic, optionally substituted heteroaliphatic, optionally substituted aryl, optionally substituted heteroaryl.

In certain embodiments, Z is an optionally substituted bivalent $C_{1-10}$ hydrocarbon chain.

In certain embodiments, Z is an optionally substituted bivalent $C_{1-8}$ hydrocarbon chain. In certain embodiments, Z is an optionally substituted bivalent $C_{1-6}$ hydrocarbon chain. In certain embodiments, Z is an optionally substituted bivalent $C_{1-4}$ hydrocarbon chain. In certain embodiments, Z is an optionally substituted bivalent $C_{1-2}$ hydrocarbon chain. In certain embodiments, Z is —($CH_2$)—, —($CH_2CH_2$)—, —($CH_2CH_2CH_2$)—, —($CH_2CH_2CH_2CH_2$)—, —($CH_2CH_2CH_2CH_2CH_2$)—, or —($CH_2CH_2CH_2CH_2CH_2CH_2$)—. In certain embodiments, Z is —($CH_2$)— or —($CH_2CH_2$)—. In certain embodiments, Z is —($CH_2$)—. In certain embodiments, Z is —($CH_2CH_2$)—. In certain embodiments, Z is —($CH_2CH_2CH_2$)—. In certain embodiments, Z is —($CH_2CH_2CH_2CH_2$)—.

In certain embodiments, Z is an optionally substituted bivalent $C_{1-10}$ hydrocarbon chain, wherein 1, 2 or 3 methylene units of Z are optionally and independently replaced with one or more groups selected from —S—, —O—, —$NR^a$—, —(C=$NR^a$)—, —(C=O)—, —(S=O)—, —S(=O)$_2$—, —($CR^b$=$CR^b$)—, —(N=N)—, an optionally substituted arylene moiety or an optionally substituted heteroarylene moiety. In certain embodiments, Z is an optionally substituted bivalent $C_{1-10}$ hydrocarbon chain, wherein 1, 2 or 3 methylene units of Z are optionally and independently replaced with one or more groups selected from —S—, —O—, —$NR^a$—, —(C=$NR^a$)—, or —(C=O)—. In certain embodiments, Z is —$CH_2CH_2NH(C$=$O)C(CH_3)_2$—, —$CH_2CH_2N(C$=$NH)(CH_2)_3S$—, —$CH(R^f)_2$, —$CH_2CH(R^f)_2$, —$CH_2CH_2CH(R^f)_2$—, —$CH_2S$—, or —$CH_2CH_2S$—, wherein $R^f$ is optionally substituted aliphatic, optionally substituted heteroaliphatic, optionally substituted aryl, optionally substituted heteroaryl (e.g., in certain embodiments, $R^f$ is optionally substituted aryl; in certain embodiments, $R^f$ is phenyl). In certain embodiments, Z is —$CH_2CH_2NH(C$=$O)C(CH_3)_2$— or —$CH_2CH_2N(C$=$NH)(CH_2)_3S$—. In certain embodiments, Z is —$CH_2CH_2NH(C$=$O)C(CH_3)_2$—. In certain embodiments, Z is —$CH_2CH_2N(C$=$NH)(CH_2)_3S$—.

iv. Y

As defined generally above, Y is hydrogen, halogen, optionally substituted aliphatic, optionally substituted heteroaliphatic, optionally substituted aryl, optionally substituted heteroaryl, —$OR^e$ or —$SR^e$, wherein $R^e$ is hydrogen, optionally substituted aliphatic, optionally substituted heteroaliphatic, optionally substituted aryl, or optionally substituted heteroaryl.

In certain embodiments, Y is a fragment of a free radical initiator. Such a fragment is encompassed by the definition of Y, as initiator fragments may include halogen, —$OR^e$, —$SR^e$, optionally substituted aliphatic, optionally substituted heteroaliphatic, optionally substituted aryl, and optionally substituted heteroaryl moieties.

For example, as depicted below in Table 1, if the initiator is AIBN, ABCN, or VASO 68 (commercially available from DuPont), the initiator fragment is the optionally substituted aliphatic moiety. In certain embodiments, the initiator fragment is optionally substituted with one or more nitrile (—CN) groups.

TABLE 1

| Initiator | Initiator fragment |
|---|---|
| ![AIBN structure] 2,2-azodiisobutyronitrile (AIBN) | ![fragment structure] |

TABLE 1-continued

| Initiator | Initiator fragment |
|---|---|
| 1,1'-Azobis(cyclohexanecarbonitrile) (ABCN) | |
| 4,4'-Azobis(4-cyanopentanoic acid) (VASO 68) | |

In certain embodiments, Y is hydrogen, halogen, or an initiator fragment. In certain embodiments, Y is hydrogen or halogen. In certain embodiments, Y is hydrogen or bromine.

v. X

As defined generally above, each instance of X is independently —$OR^c$ or —$N(R^d)_2$, wherein $R^c$ is hydrogen, optionally substituted aliphatic, optionally substituted heteroaliphatic, optionally substituted aryl, optionally substituted heteroaryl, a suitable hydroxyl protecting group, or an affinity ligand, and each $R^d$ is, independently, hydrogen, optionally substituted aliphatic, optionally substituted heteroaliphatic, optionally substituted aryl, optionally substituted heteroaryl, a suitable amino protecting group, or an affinity ligand. The conjugates each include at least two instances where X includes an affinity ligand.

In certain embodiments, each X is —$OR^c$.
In certain embodiments, each X is —$OR^c$ or —$N(R^d)_2$.
In certain embodiments, each X is —$N(R^d)_2$.
In certain embodiments, each $R^c$ that is not an affinity ligand is hydrogen. In certain embodiments, each $R^c$ that is not an affinity ligand is an optionally substituted aliphatic moiety. In certain embodiments, each $R^c$ that is not an affinity ligand is an optionally substituted heteroaliphatic moiety. In certain embodiments, each $R^c$ that is not an affinity ligand is an optionally substituted aryl. In certain embodiments, each $R^c$ that is not an affinity ligand is an optionally substituted heteroaryl. In certain embodiments, each $R^c$ that is not an affinity ligand is a suitable hydroxyl protecting group. In certain embodiments, each $R^c$ that is not an affinity ligand is a cation group. In certain embodiments, each $R^c$ that is not an affinity ligand is a cation selected from sodium, lithium, potassium, calcium, or magnesium. In certain embodiments, each $R^c$ that is not an affinity ligand is a sodium cation. In certain embodiments, each $R^c$ that is not an affinity ligand is an affinity ligand. In certain embodiments, $R^c$ is a combination of any of the above embodiments, such as, for example, wherein $R^c$ may be either hydrogen, a cation group, or an affinity ligand.

In certain embodiments, each $R^d$ that is not an affinity ligand is, independently, hydrogen or an optionally substituted aliphatic moiety. In certain embodiments, each $R^d$ that is not an affinity ligand is, independently, hydrogen or an optionally substituted heteroaliphatic moiety. In certain embodiments, each $R^d$ that is not an affinity ligand is, independently, hydrogen or an optionally substituted aryl. In certain embodiments, each $R^d$ that is not an affinity ligand is, independently, hydrogen or an optionally substituted heteroaryl. In certain embodiments, each $R^d$ that is not an affinity ligand is, independently, hydrogen or a suitable amino protecting group. In certain embodiments, each $R^d$ is, independently, hydrogen or an affinity ligand. In certain embodiments, $R^d$ is a combination of any of the above embodiments, such as, for example, wherein $R^d$ may be either hydrogen, an affinity ligand, or an optionally substituted aliphatic group.

The term "cation", as used herein, refers to an atom or group of atoms carrying a positive charge. The cation is paired with one or more anionic (e.g., carboxylate, C(=O)O⁻) groups to form a salt. Exemplary cations include alkali metal, alkaline earth metal, ammonium and $N^+(C_{1-4}alkyl)_4$ cationic species. Representative alkali or alkaline earth metal cations include sodium cation, lithium cation, potassium cation, calcium cation, magnesium cation, and the like. Other cations include nontoxic ammonium, quaternary ammonium, and amine cations formed using counterions such as halide, hydroxide, carboxylate, sulfate, phosphate, nitrate, lower alkyl sulfonate and aryl sulfonate. See, for example, Berge et al., *J. Pharmaceutical Sciences* 66:1-19, 1977.

In general, the two or more affinity ligands within the conjugate are capable of competing with a target molecule for binding with a multivalent cross-linking agent (as described below). In certain embodiments, the relative affinity of the conjugate and target molecule for the cross-linking agent is in the range of 1:1 to 100:1 (where a relative affinity of 100:1 means that, in an equilibrium mixture of conjugate, target molecule and cross-linking agent (in pH 7 HEPES buffered saline at 37 C), the cross-linking agent will bind about equal molar amounts of conjugate and target molecule if the concentration of target molecule is 100× the concentration of conjugate). In certain embodiments, the relative affinity is in the range of 1:1 to 50:1, 1:1 to 10:1, 1:1 to 5:1 or 1:1 to 2:1. The two or more separate affinity ligands may have the same or different chemical structures. For example, the two or more separate affinity ligands may have the same chemical structure as the target molecule (e.g., glucose) or may be a chemically related species of the target molecule. For example, when the target molecule is glucose the affinity ligands may include a saccharide. Thus, in certain embodiments, the affinity ligands are capable of competing with glucose for binding to a multivalent glucose binding molecule (e.g., without limitation Con A, mannan-binding lectin or MBL, etc.).

In certain embodiments, the affinity ligand is of formula (IVa) or (IVb):

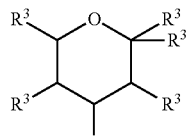

IVa

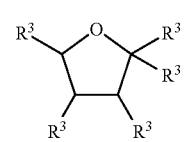

IVb wherein:
each $R^3$ is independently hydrogen, $-OR^y$, $-N(R^y)_2$, $-SR^y$, $-O-Y^L$, $-G-Z^L$, or $-CH_2R^z$;
each $R^z$ is independently hydrogen, $-OR^y$, $-N(R^y)_2$, $-SR^y$, or $-O-Y^L$;
each $R^y$ is independently $-R^4$, $-SO_2R^4$, $-S(O)R^4$, $-P(O)(OR^4)_2$, $-C(O)R^4$, $-CO_2R^4$, or $-C(O)N(R^4)_2$;
each $Y^L$ is independently a monosaccharide, disaccharide, or trisaccharide;
each G is independently a covalent bond or an optionally substituted $C_{1-9}$ alkylene, wherein one or more methylene units of G is optionally replaced by $-O-$, $-S-$, $-N(R^4)-$, $-C(O)-$, $-OC(O)-$, $-C(O)O-$, $-C(O)N(R^4)-$, $-N(R^4)C(O)-$, $-N(R^4)C(O)N(R^4)-$, $-SO_2-$, $-SO_2N(R^4)-$, $-N(R^4)SO_2-$, or $-N(R^4)SO_2N(R^4)-$;
each $Z^L$ is independently halogen, $-N(R^4)_2$, $-OR^4$, $-SR^4$, $-N_3$, $-C\equiv CR^4$, $-CO_2R^4$, $-C(O)R^4$, or $-OSO_2R^4$; and
each $R^4$ is independently hydrogen or an optionally substituted group selected from $C_{1-6}$ aliphatic, phenyl, a 4-7 membered heterocyclic ring having 1-2 heteroatoms selected from nitrogen, oxygen, or sulfur, or a 5-6 membered monocyclic heteroaryl ring having 1-4 heteroatoms selected from nitrogen, oxygen, or sulfur.

In certain embodiments, the affinity ligand of formula (IVa) or (IVb) is a monosaccharide. In certain embodiments, the affinity ligand is a disaccharide. In certain embodiments, the affinity ligand is a trisaccharide. In certain embodiments, the affinity ligand is a tetrasaccharide. In certain embodiments, the affinity ligand comprises no more than four saccharide moieties.

As defined generally above, each $R^3$ is independently hydrogen, $-OR^y$, $-N(R^y)_2$, $-SR^y$, $-O-Y^L$, $-G-Z^L$, or $-CH_2R^z$. In certain embodiments, $R^3$ is hydrogen. In certain embodiments, $R^3$ is $-OH$. In other embodiments, $R^3$ is $-NHC(O)CH_3$. In certain embodiments, $R^3$ is $-O-Y^L$. In certain other embodiments, $R^3$ is $-G-Z^L$. In some embodiments, $R^3$ is $-CH_2OH$. In other embodiments, $R^3$ is $-CH_2-O-Y^L$. In yet other embodiments, $R^3$ is $-NH_2$. One of ordinary skill in the art will appreciate that each $R^3$ substituent in formula (IVa) or (IVb) may be of (R) or (S) stereochemistry.

As defined generally above, each $R^z$ is independently hydrogen, $-OR^y$, $-N(R)_2$, $-SR^y$, or $-O-Y^L$. In some embodiments, $R^z$ is hydrogen. In certain embodiments, $R^z$ is $-OH$. In other embodiments, $R^z$ is $-O-Y^L$.

As defined generally above, each $R^y$ is independently $-R^4$, $-SO_2R^4$, $-S(O)R^4$, $-P(O)(OR^4)_2$, $-C(O)R^4$, $-CO_2R^4$, or $-C(O)N(R^4)_2$. In some embodiments, $R^y$ is hydrogen. In other embodiments, $R^y$ is $-R^4$. In some embodiments, $R^y$ is $-C(O)R^4$. In certain embodiments, $R^y$ is acetyl. In other embodiments, $R^y$ is $-SO_2R^4$, $-S(O)R^4$, $-P(O)(OR^4)_2$, $-CO_2R^4$, or $-C(O)N(R^4)_2$.

As defined generally above, $Y^L$ is a monosaccharide, disaccharide, or trisaccharide. In certain embodiments, $Y^L$ is a monosaccharide. In some embodiments, $Y^L$ is a disaccharide. In other embodiments, $Y^L$ is a trisaccharide. In some embodiments, $Y^L$ is mannose, glucose, fructose, galactose, rhamnose, or xylopyranose. In some embodiments, $Y^L$ is sucrose, maltose, turanose, trehalose, cellobiose, or lactose. In certain embodiments, $Y^L$ is mannose. In certain embodiments, $Y^L$ is D-mannose. One of ordinary skill in the art will appreciate that the saccharide $Y^L$ is attached to the oxygen group of $-O-Y^L$ through anomeric carbon to form a glycosidic bond. The glycosidic bond may be of an alpha or beta configuration.

As defined generally above, each G is independently a covalent bond or an optionally substituted $C_{1-9}$ alkylene, wherein one or more methylene units of G is optionally replaced by $-O-$, $-S-$, $-N(R^4)-$, $-C(O)-$, $-OC(O)-$, $-C(O)O-$, $-C(O)N(R^4)-$, $-N(R^4)C(O)-$, $-N(R^4)C(O)N(R^4)-$, $-SO_2-$, $-SO_2N(R^4)-$, $-N(R^4)SO_2-$, or $-N(R^4)SO_2N(R^4)-$. In some embodiments, G is a covalent bond. In certain embodiments, G is $-O-C_{1-8}$ s alkylene. In certain embodiments, G is $-OCH_2CH_2-$.

As defined generally above, each $Z^L$ is independently halogen, $-N(R^4)_2$, $-OR^4$, $-SR^4$, $-N_3$, $-C\equiv CR^4$, $-CO_2R^4$, $-C(O)R^4$, or $-OSO_2R^4$. In some embodiments, $Z^L$ is a halogen or $-OSO_2R^4$. In other embodiments, $Z^L$ is $-N_3$ or $-C\equiv CR^4$. In certain embodiments, $Z^L$ is $-N(R^4)_2$, $-OR^4$, or $-SR^4$. In certain embodiments, $Z^L$ is $-SH$. In certain embodiments, $Z^L$ is $-NH_2$. In certain embodiments, $-G-Z^L$ is $-OCH_2CH_2NH_2$.

In some embodiments, the $R^3$ substituent on the C1 carbon of formula (IVa) is $-G-Z^L$ to give a compound of formula (IVa-i):

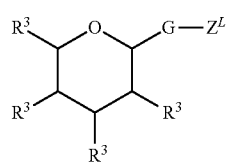

IVa-i wherein $R^3$, G, and $Z^L$ are as defined and described herein.

In some embodiments, the ligand is of formula (IVa-ii):

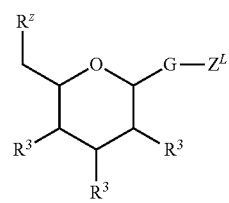

IVa-ii wherein $R^3$, $R^z$, G, and $Z^L$ are as defined and described herein.

For example, in certain embodiments, one might use an affinity ligand that includes one or more of the following: glucose, sucrose, maltose, mannose, derivatives of these (e.g., glucosamine, mannosamine, methylglucose, methylmannose, ethylglucose, ethylmannose, etc.) and/or higher order combinations of these (e.g., a bimannose, a linear and/or branched trimannose, etc.). In certain embodiments, the affinity ligand includes a monosaccharide. In certain embodiments, the affinity ligand includes a disaccharide. In certain embodiments, the affinity ligand includes a trisaccharide. In certain embodiments, the affinity ligand includes a polysaccharide. In some embodiments, the affinity ligand includes a saccharide and one or more amine groups. In some embodiments, the affinity ligand is aminoethylglucose (AEG). In some embodiments, the affinity ligand is aminoethylmannose (AEM). In some embodiments, the affinity ligand is aminoethylbimannose (AEBM). In some embodiments, the affinity ligand is aminoethyltrimannose (AETM). In some embodiments, the affinity ligand is β-aminoethyl-N-acetylglucosamine (AEGA). In some embodiments, the affinity ligand is aminoethylfucose (AEF). In other embodiments, the affinity ligand is D-glucosamine (GA). In certain embodiments, a saccharide ligand is of the "D" configuration. In other embodiments, a saccharide ligand is of the "L" configuration. Below we show the structures of these exemplary affinity ligands. Other exemplary affinity ligands will be recognized by those skilled in the art.

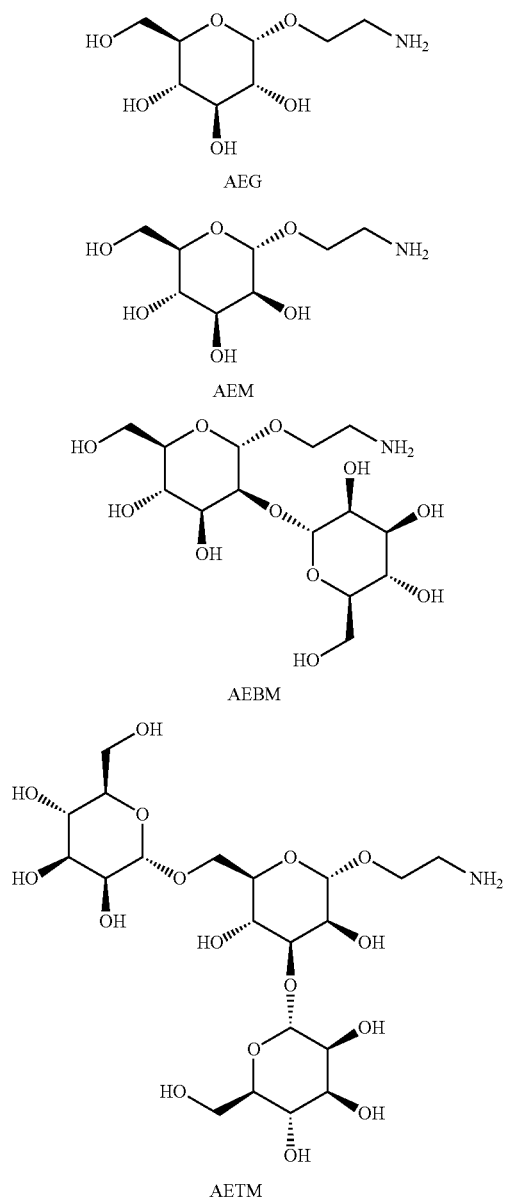

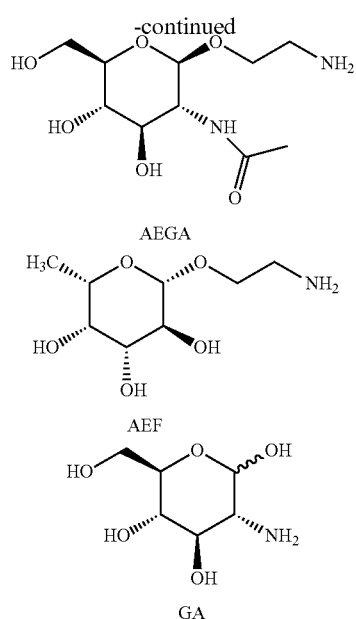

In certain embodiments, a conjugate may include 5 or more, 10 or more, or 20 or more affinity ligands. In certain embodiments, a conjugate may include a framework which comprises 2-5, 2-10, 2-20, 2-25, 2-50 or 2-100 affinity ligands. In certain embodiments, a conjugate may include a framework which comprises as few as 2, 3 or 4 separate affinity ligands, e.g., 2, 3 or 4 AEM, AEBM or AETM ligands (including mixtures thereof).

vi. -----

----- corresponds to a single or double bond. In certain embodiments, ----- is a single bond.

vii. W (Drug)

In certain embodiments, W is a drug. For example, a drug may be included when the material is to be used for therapeutic purposes, e.g., to controllably deliver a drug in a patient. It is to be understood that a conjugate can comprise any drug. A conjugate can comprise more than one copy of the same drug and/or can comprise more than one type of drug. The conjugates are not limited to any particular drug and may include small molecule drugs or biomolecular drugs. In general, the drug(s) used will depend on the disease or disorder to be treated.

In certain embodiments, the drug or detectable label is conjugated to the polymer framework via an amino group. In certain embodiments, the drug or detectable label is conjugated to the polymer framework via a primary amino group.

As used herein, when two entities are "covalently conjugated" to one another they are linked by a direct or indirect covalent interaction. An indirect covalent interaction is when two entities are covalently connected through a linker group (e.g., an alkylene group, arylene group, heteroarylene group, heteroatom, ester linkage, amide linkage, and the like).

For example, in certain embodiments, the group

corresponds to the group

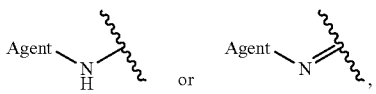

wherein the group [Agent-NH—] or [Agent-N=] is the drug directly covalently conjugated via a primary amino group.

Without limitation, in various embodiments a conjugate can comprise any one of the following drugs: diclofenac, nifedipine, rivastigmine, methylphenidate, fluoroxetine, rosiglitazone, prednison, prednisolone, codeine, ethylmorphine, dextromethorphan, noscapine, pentoxiverine, acetylcysteine, bromhexine, epinephrine, isoprenaline, orciprenaline, ephedrine, fenoterol, rimiterol, ipratropium, cholinetheophyllinate, proxiphylline, bechlomethasone, budesonide, deslanoside, digoxine, digitoxin, disopyramide, proscillaridin, chinidine, procainamide, mexiletin, flecamide, alprenolol, proproanolol, nadolol, pindolol, oxprenolol, labetalol, tirnolol, atenolol, pentaeritrityltetranitrate, isosorbiddinitrate, isosorbidmononitrate, niphedipin, phenylamine, verapamil, diltiazem, cyclandelar, nicotinylalcholhol, inositolnicotinate, alprostatdil, etilephrine, prenalterol, dobutamine, dopamine, dihydroergotamine, guanetidine, betanidine, methyldopa, reserpine, guanfacine, trimethaphan, hydralazine, dihydralazine, prazosine, diazoxid, captopril, nifedipine, enalapril, nitroprusside, bendroflumethiazide, hydrochlorthiazide, metychlothiazide, polythiazide, chlorthalidon, cinetazon, clopamide, mefruside, metholazone, bumetanide, ethacrynacide, spironolactone, amiloride, chlofibrate, nicotinic acid, nicheritrol, brompheniramine, cinnarizine, dexchlorpheniramine, clemastine, antazoline, cyproheptadine, proethazine, cimetidine, ranitidine, sucralfat, papaverine, moxaverine, atropin, butylscopolamin, emepron, glucopyrron, hyoscyamine, mepensolar, methylscopolamine, oxiphencyclimine, probanteline, terodilin, sennaglycosides, sagradaextract, dantron, bisachodyl, sodiumpicosulfat, etulos, diphenolxylate, loperamide, salazosulfapyridine, pyrvin, mebendazol, dimeticon, ferrofumarate, ferrosuccinate, ferritetrasemisodium, cyanochobalamine, folid acid heparin, heparin co-factor, diculmarole, warfarin, streptokinase, urokinase, factor VIII, factor IX, vitamin K, thiopeta, busulfan, chlorambucil, cyclophosphamid, melfalan, carmustin, mercatopurin, thioguanin, azathioprin, cytarabin, vinblastin, vinchristin, vindesin, procarbazine, dacarbazine, lomustin, estramustin, teniposide, etoposide, cisplatin, amsachrin, aminogluthetimid, phosphestrol, medroxiprogresterone, hydroxiprogesterone, megesterol, noretisteron, tamoxiphen, ciclosporin, sulfosomidine, bensylpenicillin, phenoxymethylpenicillin, dicloxacillin, cloxacillin, flucoxacillin, ampicillin, amoxicillin, pivampicillin, bacampicillin, piperacillin, meziocillin, mecillinam, pivmecillinam, cephalotin, cephalexin, cephradin, cephydroxil, cephaclor, cefuroxim, cefotaxim, ceftazidim, cefoxitin, aztreonam, imipenem, cilastatin, tetracycline, lymecycline, demeclocycline, metacycline, oxitetracycline, doxycycline, chloramphenicol, spiramycin, fusidic acid, lincomycin, clindamycin, spectinomycin, rifampicin, amphotericin B, griseofulvin, nystatin, vancomycin, metronidazole, tinidazole, trimethoprim, norfloxacin, salazosulfapyridin, aminosalyl, isoniazid, etambutol, nitrofurantoin, nalidixic acid, metanamine, chloroquin, hydroxichloroquin, tinidazol, ketokonazol, acyclovir, interferon idoxuridin, retinal, tiamin, dexpantenol, pyridoxin, folic acid, ascorbic acid, tokoferol, phytominadion, phenfluram, corticotropin, tetracosactid, tyrotropin, somatotoprin, somatrem, vasopressin, lypressin, desmopressin, oxytocin, chloriongonadotropin, cortison, hydrocortisone, fluodrocortison, prednison, prednisolon, fluoximesteron, mesterolon, nandrolon, stanozolol, oximetolon, cyproteron, levotyroxin, liotyronin, propylthiouracil, carbimazol, tiamazol, dihydrotachysterol, alfacalcidol, calcitirol, insulin, tolbutamid, chlorpropamid, tolazamid, glipizid, glibenclamid, phenobarbital, methyprylon, pyrityidion, meprobamat, chlordiazepoxid, diazepam, nitrazepam, baclofen, oxazepam, dikaliumclorazepat, lorazepam, flunitrazepam, alprazolam, midazolam, hydroxizin, dantrolene, chlomethiazol, propionmazine, alimemazine, chlorpromazine, levomepromazine, acetophenazine, fluphenazine, perphenazine, prochlorperazine, trifluoperazine, dixyrazine, thiodirazine, periciazin, chloprothixene, tizanidine, zaleplon, zuclopentizol, flupentizol, thithixen, haloperidol, trimipramin, opipramol, chlomipramin, desipramin, lofepramin, amitriptylin, nortriptylin, protriptylin, maptrotilin, caffeine, cinnarizine, cyclizine, dimenhydinate, meclozine, prometazine, thiethylperazine, metoclopramide, scopolamine, phenobarbital, phenytoine, ethosuximide, primidone, carbamazepine, chlonazepam, orphenadrine, atropine, bensatropine, biperiden, metixene, procylidine, levodopa, bromocriptin, amantadine, ambenon, pyridostigmine, synstigmine, disulfuram, morphine, codeine, pentazocine, buprenorphine, pethidine, phenoperidine, phentanyl, methadone, piritramide, dextropropoxyphene, ketobemidone, acetylsalicylic acid, celecoxib, phenazone, phenylbutazone, azapropazone, piroxicam, ergotamine, dihydroergotamine, cyproheptadine, pizitifen, flumedroxon, allopurinol, probenecid, sodiummaurothiomalate auronofin, penicillamine, estradiol, estradiolvalerianate, estriol, ethinylestradiol, dihydrogesteron, lynestrenol, medroxiprogresterone, noretisterone, cyclophenile, clomiphene, levonorgestrel, mestranol, ornidazol, tinidazol, ekonazol, chlotrimazol, natamycine, miconazole, sulbentin, methylergotamine, dinoprost, dinoproston, gemeprost, bromocriptine, phenylpropanolamine, sodiumchromoglicate, azetasolamide, dichlophenamide, betacarotene, naloxone, calciumfolinate, in particular clonidine, thephylline, dipyradamol, hydrochlothiazade, scopolamine, indomethacine, furosemide, potassium chloride, morphine, ibuprofen, salbutamol, terbutalin, calcitonin, etc. It is to be understood that this list is intended to be exemplary and that any drug, whether known or later discovered, may be used in a conjugate of the present disclosure.

In various embodiments, a conjugate may include a hormonal drug which may be peptidic or non-peptidic, e.g., adrenaline, noradrenaline, angiotensin, atriopeptin, aldosterone, dehydroepiandrosterone, androstenedione, testosterone, dihydrotestosterone, calcitonin, calcitriol, calcidiol, corticotropin, cortisol, dopamine, estradiol, estrone, estriol, erythropoietin, follicle-stimulating hormone, gastrin, ghrelin, glucagon, gonadotropin-releasing hormone, growth hormone, growth hormone-releasing hormone, human chorionic gonadotropin, histamine, human placental lactogen, insulin, insulin-like growth factor, inhibin, leptin, a leukotriene, lipotropin, melatonin, orexin, oxytocin, parathyroid hormone, progesterone, prolactin, prolactin-releasing hormone, a prostglandin, renin, serotonin, secretin, somatostatin, thrombopoietin, thyroid-stimulating hormone, thyrotropin-releasing hormone (or thyrotropin), thyrotropin-releasing hormone, thyroxine, triiodothyronine, vasopressin, etc. In certain embodiments, the hormone may be selected from glucagon, insulin, insulin-like growth factor, leptin, thyroid-stimulating hormone, thyrotropin-releasing hormone (or thyrotropin), thyrotropin-releasing hormone, thyroxine, and triiodothyronine. It is to be understood that this list is intended to be exemplary and that any hormonal drug, whether known or later discovered, may be used in a conjugate of the present disclosure.

In various embodiments, a conjugate may include a thyroid hormone.

In various embodiments, a conjugate may include an anti-diabetic drug (i.e., a drug which has a beneficial effect on patients suffering from diabetes).

Figure 11:
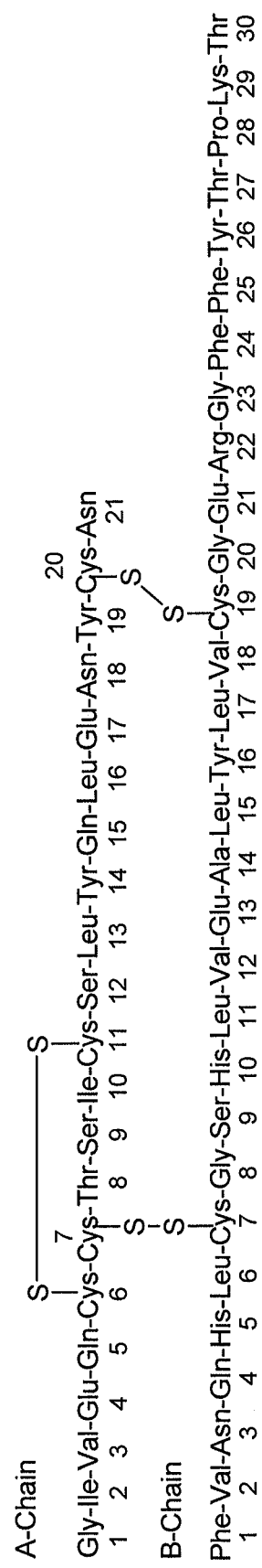
FIG. 11: shows the structure of wild-type human insulin.

In various embodiments, a conjugate may include an insulin molecule. By "an insulin molecule" we intend to encompass both wild-type and modified forms of insulin as long as they are bioactive (i.e., capable of causing a detectable reduction in glucose when administered in vivo). Wild-type insulin includes insulin from any species whether in purified, synthetic or recombinant form (e.g., human insulin, porcine insulin, bovine insulin, rabbit insulin, sheep insulin, etc.). A number of these are available commercially, e.g., from Sigma-Aldrich (St. Louis, Mo.). A variety of modified forms of insulin are known in the art (e.g. see Crotty and Reynolds, Pediatr. Emerg. Care. 23:903-905, 2007 and Gerich, Am. J. Med. 113:308-16, 2002 and references cited therein). Modified forms of insulin may be chemically modified (e.g., by addition of a chemical moiety such as a PEG group or a fatty acyl chain as described below) and/or mutated (i.e., by addition, deletion or substitution of one or more amino acids). In general, a bioactive mutant form of insulin will typically differ from wild-type insulin by 1-10 (e.g., from 1-5 or 1-2) amino acid substitutions, additions or deletions. The wild-type sequence of human insulin (A-chain and B-chain) is shown below and in FIG. 11.

```
A-Chain (SEQ ID NO: 1):
GIVEQCCTSICSLYQLENYCN

B-Chain (SEQ ID NO: 2):
FVNQHLCGSHLVEALYLVCGERGFFYTPKT
```

Human insulin differs from rabbit, porcine, bovine, and sheep insulin only in amino acids A8, A9, A10, and B30 (see table below).

| Insulin | Amino Acid Position | | | |
|---|---|---|---|---|
| | A8 | A9 | A10 | B30 |
| human | Thr | Ser | Ile | Thr |
| rabbit | Thr | Ser | Ile | Ser |
| porcine | Thr | Ser | Ile | Ala |
| bovine | Ala | Ser | Val | Ala |
| sheep | Ala | Gly | Val | Ala |

In various embodiments, an insulin molecule of the present disclosure is mutated at the B28 and/or B29 positions of the B-peptide sequence. For example, insulin lispro (HUMALOG®) is a rapid acting insulin mutant in which the penultimate lysine and proline residues on the C-terminal end of the B-peptide have been reversed ($Lys^{B28}Pro^{B29}$-human insulin). This modification blocks the formation of insulin multimers. Insulin aspart (NOVOLOG®) is another rapid acting insulin mutant in which proline at position B28 has been substituted with aspartic acid ($Asp^{B28}$-human insulin). This mutant also prevents the formation of multimers. In some embodiments, mutation at positions B28 and/or B29 is accompanied by one or more mutations elsewhere in the insulin polypeptide. For example, insulin glulisine (APIDRA®) is yet another rapid acting insulin mutant in which aspartic acid at position B3 has been replaced by a lysine residue and lysine at position B29 has been replaced with a glutamic acid residue ($Lys^{B3}Glu^{B29}$-human insulin).

In various embodiments, an insulin molecule of the present disclosure has an isoelectric point that is shifted relative to human insulin. In some embodiments, the shift in isoelectric point is achieved by adding one or more arginine residues to the N-terminus of the insulin A-peptide and/or the C-terminus of the insulin B-peptide. Examples of such insulin polypeptides include $Arg^{A0}$-human insulin, $Arg^{B31}Arg^{B32}$-human insulin, $Gly^{A21}Arg^{B31}Arg^{B32}$-human insulin, $Arg^{A0}Arg^{B31}Arg^{B32}$-human insulin, and $Arg^{A0}Gly^{A21}Arg^{B31}Arg^{B32}$-human insulin. By way of further example, insulin glargine (LANTUS®) is an exemplary long acting insulin mutant in which $Asp^{A21}$ has been replaced by glycine, and two arginine residues have been added to the C-terminus of the B-peptide. The effect of these changes is to shift the isoelectric point, producing a solution that is completely soluble at pH 4. Thus, in some embodiments, an insulin molecule of the present disclosure comprises an A-peptide sequence wherein A21 is Gly and B-peptide sequence wherein B31 is Arg-Arg. It is to be understood that the present disclosure encompasses all single and multiple combinations of these mutations and any other mutations that are described herein (e.g., $Gly^{A21}$-human insulin, $Gly^{A21}Arg^{B31}$-human insulin, $Arg^{B31}Arg^{B32}$-human insulin, $Arg^{B31}$-human insulin).

In various embodiments, an insulin molecule of the present disclosure is truncated. For example, in certain embodiments, a B-peptide sequence of an insulin polypeptide of the present disclosure is missing B1, B2, B3, B26, B27, B28, B29 and/or B30. In certain embodiments, combinations of residues are missing from the B-peptide sequence of an insulin polypeptide of the present disclosure. For example, the B-peptide sequence may be missing residues B(1-2), B(1-3), B(29-30), B(28-30), B(27-30) and/or B(26-30). In some embodiments, these deletions and/or truncations apply to any of the aforementioned insulin molecules (e.g., without limitation to produce des(B30)-insulin lispro, des(B30)-insulin aspart, des(B30)-insulin glulisine, des(B30)-insulin glargine, etc.).

In some embodiments, an insulin molecule contains additional amino acid residues on the N- or C-terminus of the A or B-peptide sequences. In some embodiments, one or more amino acid residues are located at positions A0, A21, B0 and/or B31. In some embodiments, one or more amino acid residues are located at position A0. In some embodiments, one or more amino acid residues are located at position A21. In some embodiments, one or more amino acid residues are located at position B0. In some embodiments, one or more amino acid residues are located at position B31. In certain embodiments, an insulin molecule does not include any additional amino acid residues at positions A0, A21, B0 or B31.

In certain embodiments, an insulin molecule of the present disclosure is mutated such that one or more amidated amino acids are replaced with acidic forms. For example, asparagine may be replaced with aspartic acid or glutamic acid. Likewise, glutamine may be replaced with aspartic acid or glutamic acid. In particular, $Asn^{A18}$, $Asn^{A21}$, or $Asn^{B3}$, or any combination of those residues, may be replaced by aspartic acid or glutamic acid. $Gln^{A15}$ or $Gln^{B4}$, or both, may be replaced by aspartic acid or glutamic acid. In certain embodiments, an insulin molecule has aspartic acid at position A21 or aspartic acid at position B3, or both.

One skilled in the art will recognize that it is possible to mutate yet other amino acids in the insulin molecule while retaining biological activity. For example, without limitation, the following modifications are also widely accepted in the art: replacement of the histidine residue of position B10 with aspartic acid (His$^{B10}$→Asp$^{B10}$); replacement of the phenylalanine residue at position B1 with aspartic acid (Phe$^{B1}$→Asp$^{B10}$); replacement of the threonine residue at position B30 with alanine (Thr$^{B30}$→Ala$^{B30}$); replacement of the tyrosine residue at position B26 with alanine (Tyr$^{B26}$→Ala$^{B26}$); and replacement of the serine residue at position B9 with aspartic acid (Ser$^{B9}$→Asp$^{B9}$).

In various embodiments, an insulin molecule of the present disclosure has a protracted profile of action. Thus, in certain embodiments, an insulin molecule of the present disclosure may be acylated with a fatty acid. That is, an amide bond is formed between an amino group on the insulin molecule and the carboxylic acid group of the fatty acid. The amino group may be the alpha-amino group of an N-terminal amino acid of the insulin molecule, or may be the epsilon-amino group of a lysine residue of the insulin molecule. An insulin molecule of the present disclosure may be acylated at one or more of the three amino groups that are present in wild-type insulin or may be acylated on lysine residue that has been introduced into the wild-type sequence. In certain embodiments, an insulin molecule may be acylated at position B1. In certain embodiments, an insulin molecule may be acylated at position B29. In certain embodiments, the fatty acid is selected from myristic acid (C14), pentadecylic acid (C15), palmitic acid (C16), heptadecylic acid (C17) and stearic acid (C18). For example, insulin detemir (LEVEMIR®) is a long acting insulin mutant in which Thr$^{B30}$ has been deleted, and a C14 fatty acid chain (myristic acid) has been attached to Lys$^{B29}$.

In some embodiments, the N-terminus of the A-peptide, the N-terminus of the B-peptide, the epsilon-amino group of Lys at position B29 or any other available amino group in an insulin molecule of the present disclosure is covalently linked to a fatty acid moiety of general formula:

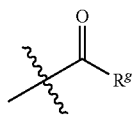

where R$^g$ is hydrogen or a C$_{1-30}$ alkyl group. In some embodiments, R$^g$ is a C$_{1-20}$ alkyl group, a C$_{3-19}$ alkyl group, a C$_{5-18}$ alkyl group, a C$_{6-17}$ alkyl group, a C$_{8-16}$ alkyl group, a C$_{10-15}$ alkyl group, or a C$_{12-14}$ alkyl group. In certain embodiments, the insulin polypeptide is conjugated to the moiety at the A1 position. In certain embodiments, the insulin polypeptide is conjugated to the moiety at the B1 position. In certain embodiments, the insulin polypeptide is conjugated to the moiety at the epsilon-amino group of Lys at position B29. In certain embodiments, position B28 of the insulin molecule is Lys and the epsilon-amino group of Lys$^{B28}$ is conjugated to the fatty acid moiety. In certain embodiments, position B3 of the insulin molecule is Lys and the epsilon-amino group of Lys$^{B3}$ is conjugated to the fatty acid moiety. In some embodiments, the fatty acid chain is 8-20 carbons long. In some embodiments, the fatty acid is octanoic acid (C8), nonanoic acid (C9), decanoic acid (C10), undecanoic acid (C11), dodecanoic acid (C12), or tridecanoic acid (C13). In certain embodiments, the fatty acid is myristic acid (C14), pentadecanoic acid (C15), palmitic acid (C16), heptadecanoic acid (C17), stearic acid (C18), nonadecanoic acid (C19), or arachidic acid (C20). For example, insulin detemir (LEVEMIR®) is a long acting insulin mutant in which Thr$^{B30}$ has been deleted, and a C14 fatty acid chain (myristic acid) is attached to Lys$^{B29}$.

In certain embodiments, an insulin molecule of the present disclosure comprises the mutations and/or chemical modifications of one of the following insulin molecules: Lys$^{B28}$Pro$^{B29}$-human insulin (insulin lispro), Asp$^{B28}$-human insulin (insulin aspart), Lys$^{B3}$Glu$^{B29}$-human insulin (insulin glulisine), Arg$^{B31}$Arg$^{B32}$-human insulin (insulin glargine), N$^{B29}$-myristoyl-des(B30)-human insulin (insulin detemir), Ala$^{B26}$-human insulin, Asp$^{B1}$-human insulin, Arg$^{A0}$-human insulin, Asp$^{B1}$Glu$^{B13}$-human insulin, Gly$^{A21}$-human insulin, Gly$^{A21}$Arg$^{B31}$Arg$^{B32}$-human insulin, Arg$^{A0}$Arg$^{B31}$Arg$^{B32}$-human insulin, Arg$^{A0}$Gly$^{A21}$Arg$^{B31}$Arg$^{B32}$-human insulin, des(B30)-human insulin, des(B27)-human insulin, des(B28-B30)-human insulin, des(B1)-human insulin, des(B1-B3)-human insulin.

In certain embodiments, an insulin molecule of the present disclosure comprises the mutations and/or chemical modifications of one of the following insulin molecules: N$^{\epsilon B29}$-palmitoyl-human insulin, N$^{\epsilon B29}$-myrisotyl-human insulin, N$^{\epsilon B28}$-palmitoyl-Lys$^{B28}$Pro$^{B29}$-human insulin, N$^{\epsilon B28}$-myristoyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B29}$-palmitoyl-des(B30)-human insulin, N$^{\epsilon B30}$-myristoyl-Thr$^{B29}$Lys$^{B30}$-human insulin, N$^{B30}$-palmitoyl-Thr$^{B29}$Lys$^{B30}$-human insulin, N$^{\epsilon B29}$-(N-palmitoyl-γ-glutamyl)-des(B30)-human insulin, N$^{\epsilon B29}$-(N-lithocolyl-γ-glutamyl)-des(B30)-human insulin, N$^{\epsilon B29}$-(ω-carboxyheptadecanoyl)-des(B30)-human insulin, N$^{\epsilon B29}$-(ω-carboxyheptadecanoyl)-human insulin.

In certain embodiments, an insulin molecule of the present disclosure comprises the mutations and/or chemical modifications of one of the following insulin molecules: N$^{\epsilon B29}$-octanoyl-human insulin, N$^{\epsilon B29}$-myristoyl-Gly$^{A21}$Arg$^{B31}$Arg$^{B31}$-human insulin, N$^{\epsilon B29}$-myristoyl-Gly$^{A21}$Gln$^{B3}$Arg$^{B31}$Arg$^{B32}$-human insulin, N$^{\epsilon B29}$-myristoyl-Arg$^{A0}$Gly$^{A21}$Arg$^{B31}$Arg$^{B32}$-human insulin, N$^{\epsilon B29}$-Arg$^{A0}$Gly$^{A21}$Gln$^{B3}$Arg$^{B31}$Arg$^{B32}$-human insulin, N$^{\epsilon B29}$-myristoyl-Arg$^{A0}$Gly$^{A21}$Asp$^{B3}$Arg$^{B31}$Arg$^{B32}$-human insulin, N$^{\epsilon B29}$-myristoyl-Arg$^{B31}$Arg$^{B32}$-human insulin, N$^{\epsilon B29}$-myristoyl-Arg$_{A0}$Arg$^{B31}$Arg$^{B32}$-human insulin, N$^{\epsilon B29}$-octanoyl-Gly$^{A21}$Arg$^{B31}$Arg$^{B32}$-human insulin, N$^{\epsilon B29}$-octanoyl-Gly$^{A21}$Gln$^{B3}$Arg$^{B31}$Arg$^{B32}$-human insulin, N$^{\epsilon B29}$-octanoyl-Arg$^{A0}$Gly$^{A21}$Arg$^{B31}$Arg$^{B32}$-human insulin, N$^{\epsilon B29}$-octanoyl-Arg$^{A0}$Gly$^{A21}$Gln$^{B3}$Arg$^{B31}$Arg$^{B32}$-human insulin, N$^{\epsilon B29}$-octanoyl-Arg$^{B0}$Gly$^{A21}$Asp$^{B3}$Arg$^{B31}$Arg$^{B32}$-human insulin, N$^{\epsilon B29}$-octanoyl-Arg$^{B31}$Arg$^{B32}$-human insulin, N$^{\epsilon B29}$-octanoyl-Arg$^{A0}$Arg$^{B31}$Arg$^{B3}$-human insulin.

In certain embodiments, an insulin molecule of the present disclosure comprises the mutations and/or chemical modifications of one of the following insulin polypeptides: N$^{\epsilon B28}$-myristoyl-Gly$^{A21}$Lys$^{B28}$Pro$^{B29}$Arg$^{B3}$ Arg$^{B32}$-human insulin, N$^{\epsilon B28}$-myristoyl-Gly$^{A21}$Gln$^{B3}$Lys$^{B28}$Pro$^{B30}$Arg$^{B31}$Arg$^{B32}$-human insulin, N$^{\epsilon B28}$-myristoyl-Arg$^{A0}$Gly$^{A21}$Lys$^{B28}$Pro$^{B29}$Arg$^{B3}$Arg$^{B32}$-human insulin, N$^{\epsilon B28}$-myristoyl-Arg$^{A0}$Gly$^{A21}$Gln$^{B3}$Lys$^{B28}$Pro$^{B29}$Arg$^{B31}$Arg$^{B32}$-human insulin, N$^{\epsilon B28}$-myristoyl-Arg$^{A0}$Gly$^{A21}$Asp$^{B3}$Lys$^{B28}$Pro$^{B29}$Arg$^{B31}$Arg$^{B32}$-human insulin, N$^{\epsilon B28}$-myristoyl-Lys$^{B28}$Pro$^{B29}$Arg$^{B31}$Arg$^{B32}$-human insulin, N$^{\epsilon B28}$-myristoyl-arg$^{A0}$Lys$^{B28}$Pro$^{B29}$Arg$^{B3}$ Arg$^{B32}$-human insulin, N$^{\epsilon B28}$-octanoyl-Gly$^{A21}$Lys$^{B28}$Pro$^{B29}$Arg$^{B31}$Arg$^{B32}$-human insulin.

In certain embodiments, an insulin molecule of the present disclosure comprises the mutations and/or chemical modifications of one of the following insulin molecules: N$^{\epsilon B28}$-octanoyl-Gly$^{A21}$Gln$^{B3}$Lys$^{B28}$Pro$^{B29}$Arg$^{B31}$Arg$^{B32}$-human insulin, $N^{\epsilon B28}$-octanoyl-Arg$^{A21}$Gly$^{A21}$Lys$^{B28}$Pro$^{B29}$Arg$^{B31}$Arg$^{B32}$-human insulin, $N^{\epsilon B28}$-octanoyl-Arg$^{A0}$Gly$^{A21}$Gln$^{B3}$Lys$^{B28}$Pro$^{B29}$Arg$^{B31}$Arg$^{B32}$-human insulin, $N^{\epsilon B28}$-octanoyl-Arg$^{A0}$Gly$^{A21}$Asp$^{B3}$Lys$^{B28}$Pro$^{B29}$Arg$^{B31}$Arg$^{B32}$-human insulin, $N^{\epsilon B28}$-octanoyl-Lys$^{B28}$Pro$^{B29}$Arg$^{B31}$Arg$^{B32}$-human insulin, $N^{\epsilon B28}$-octanoyl-Arg$^{A0}$Lys$^{B28}$Pro$^{B29}$Arg$^{B31}$Arg$^{B32}$ human insulin.

In certain embodiments, an insulin molecule of the present disclosure comprises the mutations and/or chemical modifications of one of the following insulin molecules: $N^{\epsilon B29}$-tridecanoyl-des(B30)-human insulin, $N^{\epsilon B29}$-tetradecanoyl-des(B30)-human insulin, $N^{\epsilon B29}$-decanoyl-des(B30)-human insulin, $N^{\epsilon B29}$-dodecanoyl-des(B30)-human insulin, $N^{\epsilon B29}$-tridecanoyl-Gly$^{A21}$-des(B30)-human insulin, $N^{\epsilon B29}$-tetradecanoyl-Gly$^{A21}$-des(B30)-human insulin, $N^{\epsilon B29}$-decanoyl-Gly$^{A21}$-des(B30)-human insulin, $N^{\epsilon B29}$-dodecanoyl-Gly$^{A21}$-des(B30)-human insulin, $N^{\epsilon B29}$-tridecanoyl-Gly$^{A21}$Gln$^{B3}$-des(B30)-human insulin, $N^{\epsilon B29}$-tetradecanoyl-Gly$^{A21}$Gln$^{B3}$-des(B30)-human insulin, $N^{\epsilon B29}$-decanoyl-Gly$^{A21}$-Gln$^{B3}$-des(B30)-human insulin, $N^{\epsilon B29}$-dodecanoyl-Gly$^{A21}$-Gln$^{B3}$-des(B30)-human insulin, $N^{\epsilon B29}$-tridecanoyl-Ala$^{A21}$-des(B30)-human insulin, $N^{\epsilon B29}$-tetradecanoyl-Ala$^{A21}$-des(B30)-human insulin, $N^{\epsilon B29}$-decanoyl-Ala$^{A21}$-des(B30)-human insulin, $N^{\epsilon B29}$-dodecanoyl-Ala$^{A21}$-des(B30)-human insulin, $N^{\epsilon B29}$-tridecanoyl-Ala$^{A21}$ Gln$^{B3}$-des(B30)-human insulin, $N^{\epsilon B29}$-tetradecanoyl-Ala$^{A21}$Gln$^{B3}$-des(B30)-human insulin, $N^{\epsilon B29}$-decanoyl-Ala$^{A21}$Gln$^{B3}$-des(B30)-human insulin, $N^{\epsilon B29}$-dodecanoyl-Ala$^{A21}$Gln$^{B3}$-des(B30)-human insulin, $N^{\epsilon B29}$-tridecanoyl-Gln$^{B3}$-des(B30)-human insulin, $N^{\epsilon B29}$-tetradecanoyl-Gln$^{B3}$-des(B30)-human insulin, $N^{\epsilon B29}$-decanoyl-Gln$^{B3}$-des(B30)-human insulin, $N^{\epsilon B29}$-dodecanoyl-Gln$^{B3}$ des(B30)-human insulin.

In certain embodiments, an insulin molecule of the present disclosure comprises the mutations and/or chemical modifications of one of the following insulin molecules: $N^{\epsilon B29}$-tridecanoyl-Gly$^{A21}$-human insulin, $N^{\epsilon B29}$-tetradecanoyl-Gly$^{A21}$-human insulin, $N^{\epsilon B29}$-decanoyl-Gly$^{A21}$-human insulin, $N^{\epsilon B29}$-dodecanoyl-Gly$^{A21}$-human insulin, $N^{\epsilon B29}$-tridecanoyl-Ala$^{A21}$-human insulin, $N^{\epsilon B29}$-tetradecanoyl-Ala$^{A21}$-human insulin, $N^{\epsilon B29}$-decanoyl-Ala$^{A21}$-human insulin, $N^{\epsilon B29}$ dodecanoyl-Ala$^{A21}$-human insulin.

In certain embodiments, an insulin molecule of the present disclosure comprises the mutations and/or chemical modifications of one of the following insulin molecules: $N^{\epsilon B29}$ tridecanoyl-Gly$^{A21}$Gln$^{B3}$-human insulin, $N^{\epsilon B29}$-tetradecanoyl-Gly$^{A21}$Gln$^{B3}$-human insulin, $N^{\epsilon B29}$-decanoyl-Gly$^{A21}$Gln$^{B3}$-human insulin, $N^{\epsilon B29}$-dodecanoyl-Gly$^{A21}$Gln$^{B3}$-human insulin, $N^{\epsilon B29}$ tridecanoyl-Ala$^{A21}$Gln$^{B3}$-human insulin, $N^{\epsilon B29}$-tetradecanoyl-Ala$^{A21}$Gln$^{B3}$-human insulin, $N^{\epsilon B29}$-decanoyl-Ala$^{A21}$Gln$^{B3}$-human insulin, $N^{\epsilon B29}$-dodecanoyl-Ala$^{A21}$Gln$^{B3}$-human insulin.

In certain embodiments, an insulin molecule of the present disclosure comprises the mutations and/or chemical modifications of one of the following insulin molecules: $N^{\epsilon B29}$ tridecanoyl-Gln$^{B3}$-human insulin, $N^{\epsilon B29}$-tetradecanoyl-Gln$^{B3}$-human insulin, $N^{\epsilon B29}$-decanoyl-Gln$^{B3}$-human insulin, $N^{\epsilon B29}$-dodecanoyl-Gln$^{B3}$-human insulin.

In certain embodiments, an insulin molecule of the present disclosure comprises the mutations and/or chemical modifications of one of the following insulin molecules: $N^{\epsilon B29}$ tridecanoyl-Glu$^{B30}$-human insulin, $N^{B29}$-tetradecanoyl-Glu$^{B30}$-human insulin, $N^{\epsilon B29}$-decanoyl-Glu$^{B30}$-human insulin, $N^{\epsilon B29}$-dodecanoyl-Glu$^{B30}$-human insulin.

In certain embodiments, an insulin molecule of the present disclosure comprises the mutations and/or chemical modifications of one of the following insulin molecules: $N^{\epsilon B29}$ tridecanoyl-Gly$^{A21}$Glu$^{B30}$-human insulin, $N^{\epsilon B29}$-tetradecanoyl-Gly$^{A21}$Glu$^{B30}$-human insulin, $N^{\epsilon B29}$-decanoyl-Gly$^{A21}$Glu$^{B30}$-human insulin, $N^{\epsilon B29}$-dodecanoyl-Gly$^{A21}$Glu$^{B30}$-human insulin.

In certain embodiments, an insulin molecule of the present disclosure comprises the mutations and/or chemical modifications of one of the following insulin molecules: $N^{\epsilon B29}$ tridecanoyl-Gly$^{A21}$Gln$^{B3}$Glu$^{B30}$-human insulin, $N^{\epsilon B29}$-tetradecanoyl-Gly$^{A21}$Gln$^{B3}$Glu$^{B30}$-human insulin, $N^{\epsilon B29}$-decanoyl-Gly$^{A21}$Gln$^{B3}$Glu$^{B30}$-human insulin, $N^{\epsilon B29}$-dodecanoyl-Gly$^{A21}$Gln$^{B3}$Glu$^{B30}$-human insulin, $N^{\epsilon B29}$-tridecanoyl-Ala$^{A21}$Glu$^{B30}$-human insulin, $N^{\epsilon B29}$-tetradecanoyl-Ala$^{A21}$Glu$^{B30}$-human insulin, $N^{\epsilon B29}$-decanoyl-Ala$^{A21}$Glu$^{B30}$-human insulin, $N^{\epsilon B29}$-dodecanoyl-Ala$^{A21}$Glu$^{B30}$-human insulin, $N^{\epsilon B29}$-tridecanoyl-Ala$^{A21}$Glu$^{B3}$-human insulin, $N^{\epsilon B29}$-tridecanoyl-Ala$^{A21}$Gln$^{B3}$Glu$^{B30}$-human insulin, $N^{\epsilon B29}$-tetradecanoyl-Ala$^{A21}$Gln$^{B3}$Glu$^{B30}$-human insulin, $N^{\epsilon B29}$-decanoyl-Ala$^{A21}$Gln$^{B3}$Glu$^{B30}$-human insulin, $N^{\epsilon B29}$-dodecanoyl-Ala$^{A21}$Gln$^{B3}$Glu$^{B30}$-human insulin.

In certain embodiments, an insulin molecule of the present disclosure comprises the mutations and/or chemical modifications of one of the following insulin molecules: $N^{\epsilon B29}$-tridecanoyl-Gln$^{B3}$Glu$^{B30}$-human insulin, $N^{\epsilon B29}$-tetradecanoyl-Gln$^{B3}$Glu$^{B30}$-human insulin, $N^{\epsilon B29}$-decanoyl-Gln$^{B3}$Glu$^{B30}$-human insulin, $N^{\epsilon B29}$-dodecanoyl-Gln$^{B3}$Glu$^{B30}$-human insulin.

In certain embodiments, an insulin molecule of the present disclosure comprises the mutations and/or chemical modifications of one of the following insulin molecules: $N^{\epsilon B29}$ formyl-human insulin, $N^{\alpha B1}$-formyl-human insulin, $N^{\alpha A1}$-formyl-human insulin, $N^{\epsilon B29}$-formyl-$N^{\alpha B1}$-formyl-human insulin, $N^{\epsilon B29}$-formyl-$N^{\alpha A1}$-formyl-human insulin, $N^{\alpha A1}$-formyl-$N^{\alpha B1}$-formyl-human insulin, $N^{\epsilon B29}$-formyl-$N^{\alpha A1}$-formyl-$N^{\alpha B1}$-formyl-human insulin.

In certain embodiments, an insulin molecule of the present disclosure comprises the mutations and/or chemical modifications of one of the following insulin molecules: $N^{\epsilon B29}$ acetyl-human insulin, $N^{\alpha B1}$-acetyl-human insulin, $N^{\alpha A1}$-acetyl-human insulin, $N^{\epsilon B29}$-acetyl-$N^{\alpha B1}$-acetyl-human insulin, $N^{\epsilon B29}$-acetyl-$N^{\alpha A1}$-acetyl-human insulin, $N^{\alpha A1}$-acetyl-$N^{\alpha B1}$-acetyl-human insulin, $N^{\epsilon B29}$-acetyl-$N^{\alpha A1}$-acetyl-$N^{\alpha B1}$-acetyl-human insulin.

In certain embodiments, an insulin molecule of the present disclosure comprises the mutations and/or chemical modifications of one of the following insulin molecules: $N^{\epsilon B29}$ propionyl-human insulin, $N^{\alpha B1}$-propionyl-human insulin, $N^{\alpha A1}$-propionyl-human insulin, $N^{\epsilon B29}$-acetyl-$N^{\alpha B1}$-propionyl-human insulin, $N^{\epsilon B29}$-propionyl-$N^{\alpha A1}$-propionyl-human insulin, $N^{\alpha A1}$-propionyl-$N^{\alpha B1}$-propionyl-human insulin, $N^{\epsilon B29}$-propionyl-$N^{\alpha A1}$-propionyl-$N^{\alpha B1}$-propionyl-human insulin.

In certain embodiments, an insulin molecule of the present disclosure comprises the mutations and/or chemical modifications of one of the following insulin molecules: $N^{\epsilon B29}$ butyryl-human insulin, $N^{\alpha B1}$-butyryl-human insulin, $N^{\alpha A1}$-butyryl-human insulin, $N^{\epsilon B29}$-butyryl-$N^{\alpha B1}$-butyryl-human insulin, $N^{\epsilon B29}$-butyryl-$N^{\alpha A1}$-butyryl-human insulin, $N^{\alpha A1}$-butyryl-$N^{\alpha B1}$-butyryl-human insulin, $N^{\epsilon B29}$-butyryl-$N^{\alpha A1}$-butyryl-$N^{\alpha B1}$-butyryl-human insulin.

In certain embodiments, an insulin molecule of the present disclosure comprises the mutations and/or chemical modifications of one of the following insulin molecules: $N^{\epsilon B29}$ pentanoyl-human insulin, $N^{\alpha B1}$-pentanoyl-human insulin, $N^{\alpha A1}$-pentanoyl-human insulin, $N^{\epsilon B29}$ pentanoyl-$N^{\alpha B1}$-pentanoyl-human insulin, $N^{\epsilon B29}$-pentanoyl-$N^{\alpha A1}$-pentanoyl-human insulin, $N^{\alpha A1}$-pentanoyl-$N^{\alpha B1}$-pentanoyl-human insulin, $N^{\epsilon B29}$-pentanoyl-$N^{\alpha A1}$-pentanoyl-$N^{\alpha B1}$-pentanoyl-human insulin.

In certain embodiments, an insulin molecule of the present disclosure comprises the mutations and/or chemical modifications of one of the following insulin molecules: $N^{\epsilon B29}$ hexanoyl-human insulin, $N^{\alpha B1}$-hexanoyl-human insulin, $N^{\alpha A1}$-hexanoyl-human insulin, $N^{\epsilon B29}$-hexanoyl-$N^{\alpha B1}$-hexanoyl-human insulin, $N^{\epsilon B29}$-hexanoyl-$N^{\alpha A1}$-hexanoyl-human insulin, $N^{\alpha A1}$-hexanoyl-$N^{\alpha B1}$-hexanoyl-human insulin, $N^{\epsilon B29}$-hexanoyl-$N^{\alpha A1}$-hexanoyl-$N^{\alpha B1}$-hexanoyl-human insulin.

In certain embodiments, an insulin molecule of the present disclosure comprises the mutations and/or chemical modifications of one of the following insulin molecules: $N^{\epsilon B29}$-heptanoyl-human insulin, $N^{\alpha B1}$-heptanoyl-human insulin, $N^{\alpha A1}$-heptanoyl-human insulin, $N^{\epsilon B29}$-heptanoyl-$N^{\alpha B1}$-heptanoyl-human insulin, $N^{\epsilon B29}$-heptanoyl-$N^{\alpha A1}$-heptanoyl-human insulin, $N^{\alpha A1}$-heptanoyl-$N^{\alpha B1}$-heptanoyl-human insulin, $N^{\epsilon B29}$-heptanoyl-$N^{\alpha A1}$-heptanoyl-$N^{\alpha B1}$-heptanoyl-human insulin.

In certain embodiments, an insulin molecule of the present disclosure comprises the mutations and/or chemical modifications of one of the following insulin molecules: $N^{\alpha B1}$-octanoyl-human insulin, $N^{\alpha A1}$-octanoyl-human insulin, $N^{\epsilon B29}$-octanoyl-$N^{\alpha B1}$-octanoyl-human insulin, $N^{\epsilon B29}$-octanoyl-$N^{\alpha A1}$-octanoyl-human insulin, $N^{\alpha A1}$-octanoyl-$N^{\alpha B1}$-octanoyl-human insulin, $N^{\epsilon B29}$-octanoyl-$N^{\alpha A1}$-octanoyl-$N^{\alpha B1}$-octanoyl-human insulin.

In certain embodiments, an insulin molecule of the present disclosure comprises the mutations and/or chemical modifications of one of the following insulin molecules: $N^{\epsilon B29}$ nonanoyl-human insulin, $N^{\alpha B1}$-nonanoyl-human insulin, $N^{\alpha A1}$-nonanoyl-human insulin, $N^{\epsilon B29}$-nonanoyl-$N^{\alpha B1}$-nonanoyl-human insulin, $N^{\epsilon B29}$-nonanoyl-$N^{\alpha A1}$-nonanoyl-human insulin, $N^{\alpha A1}$-nonanoyl-$N^{\alpha B1}$-nonanoyl-human insulin, $N^{\epsilon B29}$-nonanoyl-$N^{\alpha A1}$-nonanoyl-$N^{\alpha B1}$-nonanoyl-human insulin.

In certain embodiments, an insulin molecule of the present disclosure comprises the mutations and/or chemical modifications of one of the following insulin molecules: $N^{\epsilon B29}$-decanoyl-human insulin, $N^{\alpha B1}$-decanoyl-human insulin, $N^{\alpha A1}$-decanoyl-human insulin, $N^{\epsilon B29}$-decanoyl-$N^{60\ B1}$-decanoyl-human insulin, $N^{\epsilon B29}$-decanoyl-$N^{\alpha A1}$-decanoyl-human insulin, $N^{\alpha A1}$-decanoyl-$N^{\alpha B1}$-decanoyl-human insulin, $N^{\epsilon B29}$-decanoyl-$N^{\alpha A1}$-decanoyl-$N^{\alpha B1}$-decanoyl-human insulin.

In certain embodiments, an insulin molecule of the present disclosure comprises the mutations and/or chemical modifications of one of the following insulin molecules: $N^{\epsilon B28}$ formyl-Lys$^{B28}$Pro$^{B29}$-human insulin, $N^{\alpha B1}$-formyl-Lys$^{B28}$Pro$^{B29}$-human insulin, $N^{\alpha A1}$-formyl-Lys$^{B28}$Pro$^{B29}$-human insulin, $N^{\epsilon B28}$-formyl-N-formyl-Lys$^{B28}$Pro$^{B29}$-human insulin, $N^{\epsilon B28}$-formyl-$N^{\alpha A1}$-formyl-Lys$^{B28}$Pro$^{B29}$-human insulin, $N^{\alpha A1}$-formyl-$N^{\alpha B1}$-formyl-Lys$^{B28}$Pro$^{B29}$-human insulin, $N^{\epsilon B28}$-formyl-$N^{\alpha A1}$-formyl-N-formyl-Lys$^{B28}$Pro$^{B29}$-human insulin, $N^{\epsilon B29}$-acetyl-Lys$^{B28}$Pro$^{B29}$-human insulin, $N^{\alpha B1}$-acetyl-Lys$^{B28}$Pro$^{B29}$-human insulin, $N^{\alpha A1}$-acetyl-Lys$^{B2}$Pro$^{B29}$-human insulin, $N^{\epsilon B28}$-acetyl-$N^{\alpha B1}$-acetyl-Lys$^{B28}$Pro$^{B29}$-human insulin.

In certain embodiments, an insulin molecule of the present disclosure comprises the mutations and/or chemical modifications of one of the following insulin molecules: $N^{\epsilon B28}$ acetyl-$N^{\alpha A1}$-acetyl-Lys$^{B28}$Pro$^{B29}$-human insulin, $N^{\alpha A1}$-acetyl-$N^{\alpha B1}$-acetyl-Lys$^{B28}$Pro$^{B29}$-human insulin, $N^{\epsilon B28}$-acetyl-$N^{\alpha A1}$-acetyl-$N^{\alpha B1}$-acetyl-Lys$^{B28}$Pro$^{B29}$-human insulin.

In certain embodiments, an insulin molecule of the present disclosure comprises the mutations and/or chemical modifications of one of the following insulin molecules: $N^{\epsilon B28}$-propionyl-Lys$^{B28}$Pro$^{B29}$-human insulin, $N^{\alpha B1}$-propionyl-Lys$^{B28}$Pro$^{B29}$-human insulin, $N^{\alpha A1}$-propionyl-Lys$^{B28}$Pro$^{B29}$-human insulin, $N^{\epsilon B28}$-propionyl-$N^{\alpha B1}$-propionyl-Lys$^{B28}$Pro$^{B29}$-human insulin, $N^{\epsilon B28}$-propionyl-$N^{\alpha A1}$-propionyl-Lys$^{B28}$Pro$^{B29}$-human insulin, $N^{\alpha A1}$-propionyl-$N^{B1}$-propionyl-Lys$^{B28}$Pro$^{B29}$-human insulin, $N^{\epsilon B28}$-propionyl-$N^{\alpha A1}$-propionyl-$N^{\alpha B1}$-propionyl-Lys$^{B28}$Pro$^{B29}$-human insulin.

In certain embodiments, an insulin molecule of the present disclosure comprises the mutations and/or chemical modifications of one of the following insulin molecules: $N^{\epsilon B28}$ butyryl-Lys$^{B28}$Pro$^{B29}$-human insulin, $N^{\alpha B1}$-butyryl-Lys$^{B28}$Pro$^{B29}$-human insulin, $N^{\alpha A1}$-butyryl-Lys$^{B28}$Pro$^{B29}$-human insulin, $N^{\epsilon B28}$-butyryl-$N^{\alpha B1}$-butyryl-Lys$^{B28}$Pro$^{B29}$-human insulin, $N^{\epsilon B28}$-butyryl-$N^{\alpha A1}$-butyryl-Lys$^{B28}$Pro$^{B29}$-human insulin, $N^{\alpha A1}$-butyryl-$N^{\alpha B1}$-butyryl-Lys$^{B28}$Pro$^{B29}$ human insulin, $N^{\epsilon B28}$-butyryl-$N^{\alpha A1}$-butyryl-$N^{\alpha B1}$-butyryl-Lys$^{B28}$Pro$^{B29}$-human insulin.

In certain embodiments, an insulin molecule of the present disclosure comprises the mutations and/or chemical modifications of one of the following insulin molecules: $N^{\epsilon B28}$-pentanoyl-Lys$^{B28}$Pro$^{B29}$-human insulin, $N^{\alpha B1}$-pentanoyl-Lys$^{B28}$Pro$^{B29}$-human insulin, $N^{\alpha A1}$-pentanoyl-Lys$^{B28}$Pro$^{B29}$-human insulin, $N^{\epsilon B28}$-pentanoyl-$N^{\alpha B1}$-pentanoyl-Lys$^{B28}$Pro$^{B29}$-human insulin, $N^{\epsilon B28}$-pentanoyl-$N^{\alpha A1}$-pentanoyl-Lys$^{B28}$Pro$^{B29}$-human insulin, $N^{\alpha A1}$-pentanoyl-$N^{\alpha B1}$-pentanoyl-Lys$^{B28}$Pro$^{B29}$-human insulin, $N^{\epsilon B28}$-pentanoyl-$N^{\alpha A1}$-pentanoyl-$N^{\alpha B1}$-pentanoyl-Lys$^{B28}$Pro$^{B29}$-human insulin.

In certain embodiments, an insulin molecule of the present disclosure comprises the mutations and/or chemical modifications of one of the following insulin molecules: $N^{\epsilon B28}$ hexanoyl-Lys$^{B28}$Pro$^{B29}$-human insulin, $N^{\alpha B1}$-hexanoyl-Lys$^{B28}$Pro$^{B29}$-human insulin, $N^{\alpha A1}$-hexanoyl-Lys$^{B28}$Pro$^{B29}$-human insulin, $N^{\epsilon B28}$-hexanoyl-$N^{\alpha B1}$-hexanoyl-Lys$^{B28}$Pro$^{B29}$-human insulin, $N^{\epsilon B28}$-hexanoyl-$N^{\alpha A1}$-hexanoyl-Lys$^{B28}$Pro$^{B29}$-human insulin, $N^{\alpha A1}$-hexanoyl-$N^{\alpha B1}$-hexanoyl-Lys$^{B28}$Pro$^{B29}$-human insulin, $N^{\epsilon B28}$-hexanoyl-$N^{\alpha A1}$-hexanoyl-$N^{\alpha B1}$-hexanoyl-Lys$^{B28}$Pro$^{B29}$-human insulin.

In certain embodiments, an insulin molecule of the present disclosure comprises the mutations and/or chemical modifications of one of the following insulin molecules: $N^{\epsilon B28}$-heptanoyl-Lys$^{B28}$Pro$^{B29}$-human insulin, $N^{\alpha B1}$-heptanoyl-Lys$^{B28}$Pro$^{B29}$-human insulin, $N^{\alpha A1}$ heptanoyl-Lys$^{B28}$Pro$^{B29}$-human insulin, $N^{\epsilon B28}$-heptanoyl-$N^{\alpha B1}$-heptanoyl-Lys$^{B28}$Pro$^{B29}$-human insulin, $N^{\epsilon B28}$-heptanoyl-$N^{\alpha A1}$-heptanoyl-Lys$^{B28}$Pro$^{B29}$-human insulin, $N^{\alpha A1}$-heptanoyl-$N^{\alpha B1}$-heptanoyl-Lys$^{B28}$Pro$^{B29}$-human insulin, $N^{\epsilon B2}$-heptanoyl-$N^{\alpha A1}$-heptanoyl-$N^{\alpha B1}$-heptanoyl-Lys$^{B28}$Pro$^{B29}$-human insulin.

In certain embodiments, an insulin molecule of the present disclosure comprises the mutations and/or chemical modifications of one of the following insulin molecules: $N^{\epsilon B28}$ octanoyl-Lys$^{B28}$Pro$^{B29}$-human insulin, $N^{60\ B1}$-octanoyl-Lys$^{B28}$Pro$^{B29}$-human insulin, $N^{\alpha A1}$-octanoyl-Lys$^{B28}$Pro$^{B29}$-human insulin, $N^{\epsilon B28}$-octanoyl-$N^{\alpha B1}$-octanoyl-Lys$^{B28}$Pro$^{B29}$-human insulin, $N^{\epsilon B28}$-octanoyl-$N^{\alpha A1}$-octanoyl-Lys$^{B28}$Pro$^{B29}$-human insulin, $N^{\alpha A1}$-octanoyl-$N^{\alpha B1}$-octanoyl-Lys$^{B28}$Pro$^{B29}$-human insulin, $N^{\epsilon B28}$-octanoyl-$N^{\alpha A1}$-octanoyl-$N^{\alpha B1}$-octanoyl-Lys$^{B28}$Pro$^{B29}$-human insulin.

In certain embodiments, an insulin molecule of the present disclosure comprises the mutations and/or chemical modifications of one of the following insulin molecules: $N^{\epsilon B28}$-nonanoyl-Lys$^{B28}$Pro$^{B29}$-human insulin, $N^{\alpha B1}$-nonanoyl-Lys$^{B28}$Pro$^{B29}$-human insulin, $N^{\alpha A1}$-nonanoyl-Lys$^{B28}$Pro$^{B29}$-human insulin, $N^{\epsilon B28}$-nonanoyl-$N^{\alpha B1}$-nonanoyl-Lys$^{B28}$Pro$^{B29}$-human insulin, $N^{\epsilon B28}$-nonanoyl-$N^{\alpha A1}$-nonanoyl-Lys$^{B28}$Pro$^{B29}$-human insulin, $N^{\alpha A1}$-nonanoyl-$N^{\alpha B1}$-nonanoyl-Lys$^{B28}$Pro$^{B29}$-human insulin, $N^{\epsilon B28}$-nonanoyl-$N^{\alpha A1}$-nonanoyl-$N^{\alpha B1}$-nonanoyl-Lys$^{B28}$Pro$^{B29}$-human insulin.

In certain embodiments, an insulin molecule of the present disclosure comprises the mutations and/or chemical modifications of one of the following insulin molecules: $N^{\epsilon B28}$-decanoyl-Lys$^{B28}$Pro$^{B29}$-human insulin, Nm-decanoyl-Lys$^{B28}$Pro$^{B29}$-human insulin, $N^{\alpha A1}$-decanoyl-Lys$^{B28}$Pro$^{B29}$-human insulin, $N^{\epsilon B28}$-decanoyl-$N^{\alpha B1}$-decanoyl-Lys$^{B28}$Pro$^{B29}$-human insulin, $N^{\epsilon B28}$-decanoyl-$N^{\alpha A1}$-decanoyl-Lys$^{B28}$Pro$^{B29}$-human insulin, $N^{\alpha A1}$-decanoyl-$N^{\alpha B1}$-decanoyl-Lys$^{B28}$Pro$^{B29}$-human insulin, $N^{\epsilon B28}$-decanoyl-$N^{\alpha A1}$-decanoyl-$N^{\alpha B1}$-decanoyl-Lys$^{B28}$Pro$^{B29}$-human insulin.

In certain embodiments, an insulin molecule of the present disclosure comprises the mutations and/or chemical modifications of one of the following insulin molecules: $N^{\epsilon B29}$ pentanoyl-Gly$^{A21}$Arg$^{B31}$Arg$^{B32}$-human insulin, $N^{\alpha B1}$-hexanoyl-Gly$^{A21}$Arg$^{B31}$Arg$^{B32}$-human insulin, $N^{\alpha A1}$-heptanoyl-Gly$^{A21}$Arg$^{B31}$Arg$^{B32}$-human insulin, $N^{\epsilon B29}$-octanoyl-$N^{\alpha B1}$-octanoyl-Gly$^{A21}$Arg$^{B31}$Arg$^{B32}$-human insulin, $N^{\epsilon B29}$-propionyl-$N^{\alpha A1}$-propionyl-Gly$^{A21}$Arg$^{B31}$Arg$^{B32}$-human insulin, $N^{\alpha A1}$-acetyl-$N^{\alpha B1}$-acetyl-Gly$^{A21}$Arg$^{B31}$Arg$^{B32}$-human insulin, $N^{\epsilon B29}$-formyl-$N^{\alpha A1}$-formyl-$N^{\alpha B1}$-formyl-Gly$^{A21}$Arg$^{B31}$Arg$^{B32}$-human insulin, $N^{\epsilon B29}$-formyl-des(B26)-human insulin, $N^{\alpha B1}$-acetyl-Asp$^{B28}$-human insulin, $N^{\epsilon B29}$-propionyl-$N^{\alpha A1}$-propionyl-$N^{\alpha B1}$-propionyl-Asp$^{B1}$Asp$^{B3}$AspB$^{21}$-human insulin, $N^{\epsilon B29}$-pentanoyl-Gly$^{A21}$-human insulin, $N^{\alpha B1}$-hexanoyl-Gly$^{A21}$-human insulin, $N^{\alpha A1}$-heptanoyl-Gly$^{A21}$-human insulin, $N^{\epsilon B29}$-octanoyl-$N^{\alpha B1}$-octanoyl-Gly$^{A2}$1-human insulin, $N^{\alpha B29}$-propionyl-$N^{\alpha A1}$-propionyl-Gly$^{A21}$-human insulin, $N^{\alpha A1}$-acetyl-$N^{\alpha B1}$-acetyl-Gly$^{A21}$-human insulin, $N^{\epsilon B29}$-formyl-$N^{\alpha A1}$-formyl-$N^{\alpha B1}$-formyl-Gly$^{A21}$-human insulin, $N^{\epsilon B29}$-butyryl-des(B30)-human insulin, $N^{\alpha B1}$-butyryl-des(B30)-human insulin, $N^{\alpha A1}$-butyryl-des(B30)-human insulin, $N^{\epsilon B29}$-butyryl-$N^{\alpha B1}$-butyryl-des(B30)-human insulin, $N^{\epsilon B29}$-butyryl-$N^{\alpha A1}$-butyryl-des(B30)-human insulin, $N^{\alpha A1}$-butyryl-$N^{\alpha B1}$-butyryl-des(B30)-human insulin, $N^{\epsilon B29}$-butyryl-$N^{\alpha A1}$-butyryl-$N^{\alpha B1}$-butyryl-des(B30)-human insulin.

The present disclosure also encompasses modified forms of non-human insulins (e.g., porcine insulin, bovine insulin, rabbit insulin, sheep insulin, etc.) that comprise any one of the aforementioned mutations and/or chemical modifications.

These and other modified insulin molecules are described in detail in U.S. Pat. Nos. 6,906,028; 6,551,992; 6,465,426; 6,444,641; 6,335,316; 6,268,335; 6,051,551; 6,034,054; 5,952,297; 5,922,675; 5,747,642; 5,693,609; 5,650,486; 5,547,929; 5,504,188; 5,474,978; 5,461,031; and 4,421,685; and in U.S. Pat. Nos. 7,387,996; 6,869,930; 6,174,856; 6,011,007; 5,866,538; and 5,750,497, the entire disclosures of which are hereby incorporated by reference.

In various embodiments, an insulin molecule of the present disclosure includes the three wild-type disulfide bridges (i.e., one between position 7 of the A-chain and position 7 of the B-chain, a second between position 20 of the A-chain and position 19 of the B-chain, and a third between positions 6 and 11 of the A-chain).

Methods for conjugating drugs including insulin molecules are described below. In certain embodiments, an insulin molecule is conjugated to the conjugate framework via the A1 amino acid residue. In certain embodiments the A1 amino acid residue is glycine. It is to be understood however, that the present disclosure is not limited to N-terminal conjugation and that in certain embodiments an insulin molecule may be conjugated via a non-terminal A-chain amino acid residue. In particular, the present disclosure encompasses conjugation via the epsilon-amine group of a lysine residue present at any position in the A-chain (wild-type or introduced by site-directed mutagenesis). It will be appreciated that different conjugation positions on the A-chain may lead to different reductions in insulin activity. In certain embodiments, an insulin molecule is conjugated to the conjugate framework via the B1 amino acid residue. In certain embodiments the B1 amino acid residue is phenylalanine. It is to be understood however, that the present disclosure is not limited to N-terminal conjugation and that in certain embodiments an insulin molecule may be conjugated via a non-terminal B-chain amino acid residue. In particular, the present disclosure encompasses conjugation via the epsilon-amine group of a lysine residue present at any position in the B-chain (wild-type or introduced by site-directed mutagenesis). For example, in certain embodiments an insulin molecule may be conjugated via the B29 lysine residue. In the case of insulin glulisine, conjugation to the conjugate framework via the B3 lysine residue may be employed. It will be appreciated that different conjugation positions on the B-chain may lead to different reductions in insulin activity.

In various embodiments, a conjugate may include an insulin sensitizer (i.e., a drug which potentiates the action of insulin). Drugs which potentiate the effects of insulin include biguanides (e.g., metformin) and glitazones. The first glitazone drug was troglitazone which turned out to have severe side effects. Second generation glitazones include pioglitazone and rosiglitazone which are better tolerated although rosiglitazone has been associated with adverse cardiovascular events in certain trials.

In various embodiments, a conjugate may include an insulin secretagogue (i.e., a drug which stimulates insulin secretion by beta cells of the pancreas). For example, in various embodiments, a conjugate may include a sulfonylurea. Sulfonylureas stimulate insulin secretion by beta cells of the pancreas by sensitizing them to the action of glucose. Sulfonylureas can, moreover, inhibit glucagon secretion and sensitize target tissues to the action of insulin. First generation sulfonylureas include tolbutamide, chlorpropamide and carbutamide. Second generation sulfonylureas which are active at lower doses include glipizide, glibenclamide, gliclazide, glibornuride and glimepiride. In various embodiments, a conjugate may include a meglitinide. Suitable meglitinides include nateglinide, mitiglinide and repaglinide. Their hypoglycemic action is faster and shorter than that of sulfonylureas. Other insulin secretagogues include glucagon-like peptide 1 (GLP-1) and GLP-1 analogs (i.e., a peptide with GLP-1 like bioactivity that differs from GLP-1 by 1-10 amino acid substitutions, additions or deletions and/or by a chemical modification). GLP-1 reduces food intake by inhibiting gastric emptying, increasing satiety through central actions and by suppressing glucagon release. GLP-1 lowers plasma glucose levels by increasing pancreas islet cell proliferation and increases insulin production following food consumption. GLP-1 may be chemically modified, e.g., by lipid conjugation as in liraglutide to extend its in vivo half-life. Yet other insulin secretagogues include exendin-4 and exendin-4 analogs (i.e., a peptide with exendin-4 like bioactivity that differs from exendin-4 by 1-10 amino acid substitutions, additions or deletions and/or by a chemical modification). Exendin-4, found in the venom of the Gila Monster, exhibits GLP-1 like bioactivity. It has a much longer half-life than GLP-1 and, unlike GLP-1, it can be truncated by 8 amino acid residues at its N-terminus without losing bioactivity. The N-terminal region of GLP-1 and exendin-4 are almost identical, a significant difference being the second amino acid residue, alanine in GLP-1 and glycine in exendin-4, which gives exendin-4 its resistance to in vivo digestion. Exendin-4 also has an extra 9 amino acid residues at its C-terminus as compared to GLP-1. Mann et al. *Biochem. Soc. Trans.* 35:713-716, 2007 and Runge et al., *Biochemistry* 46:5830-5840, 2007 describe a variety of GLP-1 and exendin-4 analogs which may be used in a conjugate of the present disclosure. The short half-life of GLP-1 results from enzymatic digestion by dipeptidyl peptidase IV (DPP-IV). In certain embodiments, the effects of endogenous GLP-1 may be enhanced by administration of a DPP-IV inhibitor (e.g., vildagliptin, sitagliptin, saxagliptin, linagliptin or alogliptin).

In various embodiments, a conjugate may include amylin or an amylin analog (i.e., a peptide with amylin like bioactivity that differs from amylin by 1-10 amino acid substitutions, additions or deletions and/or by a chemical modification). Amylin plays an important role in glucose regulation (e.g., see Edelman and Weyer, *Diabetes Technol. Ther.* 4:175-189, 2002). Amylin is a neuroendocrine hormone that is co-secreted with insulin by the beta cells of the pancreas in response to food intake. While insulin works to regulate glucose disappearance from the bloodstream, amylin works to help regulate glucose appearance in the bloodstream from the stomach and liver. Pramlintide acetate (SYMLIN®) is an exemplary amylin analog. Since native human amylin is amyloidogenic, the strategy for designing pramlintide involved substituting certain residues with those from rat amylin, which is not amyloidogenic. In particular, proline residues are known to be structure-breaking residues, so these were directly grafted from the rat sequence into the human sequence. Glu-10 was also substituted with an asparagine.

In various embodiments, a pre-conjugated drug may contain one or more reactive moieties (e.g., carboxyl or reactive ester, amine, hydroxyl, aldehyde, sulfhydryl, maleimidyl, alkynyl, azido, etc. moieties). As discussed below, these reactive moieties may, in certain embodiments, facilitate the conjugation process. Specific examples include peptidic drugs bearing alpha-terminal amine and/or epsilon-amine lysine groups. It will be appreciated that any of these reactive moieties may be artificially added to a known drug if not already present. For example, in the case of peptidic drugs a suitable amino acid (e.g., a lysine) may be added or substituted into the amino acid sequence. In addition, as discussed in more detail below, it will be appreciated that the conjugation process may be controlled by selectively blocking certain reactive moieties prior to conjugation.

As discussed above, the present disclosure is not limited to any particular combination of drug and target molecule.

In various embodiments, a material of the present disclosure may be exploited to manipulate a natural feedback mechanism. For example, there are many natural feedback mechanisms (including most hormonal control mechanisms) in which the level of two endogenous substances are interrelated (e.g., glucose and insulin where the level of insulin increases as the level of glucose increases and the level of glucose decreases as the level of insulin increases). In such embodiments one of the endogenous substances can become the target molecule (e.g., glucose) while the other becomes the drug (e.g., insulin). Alternatively, in various embodiments, the drug can be a molecule that (a) has the same function as the other endogenous substance (e.g., reduces glucose levels), (b) stimulates the production of the other endogenous substance and/or (c) potentiates the effect(s) of the other endogenous substance. For example, when glucose is the target molecule one could use an insulin secretagogue or an insulin sensitizer instead of insulin as the drug.

Other non-limiting examples of artificial feedback systems, include, a material which releases glucagon conjugates in response to high levels of insulin, a material which releases anticoagulant conjugates (e.g., coumarines such as warfarin, acenocoumarol, phenprocoumon and phenindione, heparin, direct thrombin inhibitors such as argatroban, lepirudin, bivalirudin, and dabigatran, etc.) in response to thrombosis indicators; a material which releases lactate-lowering drug conjugates (e.g., dichloroacetate) in response to increased lactate levels; etc.

In various embodiments, a material can be designed to release conjugates which include a drug with a function that is not directly related to the target molecule. Without limitation, a material which responds to a target molecule which increases in concentration after a meal (e.g., glucose) may be used to provide long-term, mealtime dosing of a drug. Any drug which needs to be dosed periodically and/or with food would benefit from such a delivery system. As is well known in the art, many traditional drugs need to be administered with food or at mealtimes. For example, drugs which inhibit the absorption of fats (e.g., orlistat) are advantageously present during mealtime. Similarly, drugs which lower lipid levels, e.g., lovastatin, attorvastatin, or simvastatin, or triglyceride levels, e.g., gemfibrozil, may also be advantageously released at mealtimes.

viii. W (Detectable Label)

As noted above, in various embodiments, W is a detectable label. For example, a detectable label may be included in order to detect the location of conjugates within an organism, tissue or cell; when the conjugates are used in a sensor; etc. It is to be understood that a conjugate can comprise any detectable label known in the art. A conjugate can comprise more than one copy of the same label and/or can comprise more than one type of label. In general, the label(s) used will depend on the end application and the method used for detection.

The detectable label may be directly detectable or indirectly detectable, e.g., through combined action with one or more additional members of a signal producing system. Examples of directly detectable labels include radioactive, paramagnetic, fluorescent, light scattering, absorptive and colorimetric labels. Fluorescein isothiocyanate, rhodamine, phycoerythrin phycocyanin, allophycocyanin, γ-phthalaldehyde, fluorescamine, etc. are all exemplary fluorescent labels. Chemiluminescent labels, i.e., labels that are capable of converting a secondary substrate to a chromogenic product are examples of indirectly detectable labels. For example, horseradish peroxidase, alkaline phosphatase, glucose-6-phosphate dehydrogenase, malate dehydrogenase, staphylococcal nuclease, delta-V-steroid isomerase, yeast alcohol dehydrogenate, α-glycerophosphate dehydrogenase, triose phosphate isomerase, asparaginase, glucose oxidase, β-galactosidase, ribonuclease, urease, catalase, glucoamylase, acetylcholinesterase, luciferin, luciferase, aequorin and the like are all exemplary protein based chemiluminescent labels. Luminol, isoluminol, theromatic acridinium ester, imidazole, acridinium salt, oxalate ester, etc. are exemplary non-protein based chemiluminescent labels. Another non-limiting and commonly used example of an indirectly detectable label is an affinity ligand, i.e., a label with strong affinity for a secondary binding partner (e.g., an antibody or aptamer) which may itself be directly or indirectly detectable.

In general, a detectable label may be visualized or detected in a variety of ways, with the particular manner of detection being chosen based on the particular detectable label, where representative detection means include, e.g., scintillation counting, autoradiography, measurement of paramagnetism, fluorescence measurement, light absorption measurement, measurement of light scattering and the like.

In various embodiments, a pre-conjugated label may contain one or more reactive moieties (e.g., carboxyl or reactive ester, amine, hydroxyl, aldehyde, sulfhydryl, maleimidyl, alkynyl, azido, etc. moieties). As discussed below, these reactive moieties may, in certain embodiments, facilitate the conjugation process. Specific examples include peptidic labels bearing alpha-terminal amine and/or epsilon-amine lysine groups. It will be appreciated that any of these reactive moieties may be artificially added to a known label if not already present. For example, in the case of peptidic labels a suitable amino acid (e.g., a lysine) may be added or substituted into the amino acid sequence. In addition, as discussed in more detail below, it will be appreciated that the conjugation process may be controlled by selectively blocking certain reactive moieties prior to conjugation.

ix. n

As defined generally above, n is an integer between 5-25, inclusive.

In certain embodiments, n is an integer between 10-25, inclusive. In certain embodiments, n is an integer between 15-25, inclusive. In certain embodiments, n is an integer between 20-25, inclusive. In certain embodiments, n is an integer between 5-20, inclusive. In certain embodiments, n is an integer between 10-20, inclusive. In certain embodiments, n is an integer between 15-20, inclusive. In certain embodiments, n is 5, 6, 7, 8, 9, 10, 11, 12, 13, 14, 15, 16, 17, 18, 19, 20, 21, 22, 23, 24 or 25. In certain embodiments n is 5. In certain embodiments n is 10. In certain embodiments n is 15. In certain embodiments n is 20. In certain embodiments n is 25.

In certain embodiments, the group:

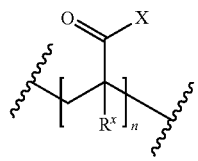

provided in any of the formulae (I), (II) or (III), or subsets thereof, corresponds to a mixture of the groups:

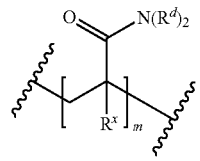 and 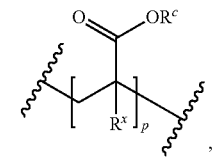, wherein the sum of (m+p) is equal to n.

In certain embodiments, each instance of m and p is, independently, an integer between 1 and 24, inclusive, with the proviso that the sum of (m+p) is greater than or equal to 5 and less than or equal to 25.

In certain embodiments, m and p are present in a ratio of about 1:10, 1:9, 1:8, 1:7, 1:6, 1:5, 1:4, 1:3, 1:2, or 1:1 (m to p).

In certain embodiments, p and m are present in a ratio of about 1:10, 1:9, 1:8, 1:7, 1:6, 1:5, 1:4, 1:3, or 1:2 (p to m).

x. Exemplary Conjugates

In certain embodiments, the present disclosure provides conjugates of formula (I-a1):

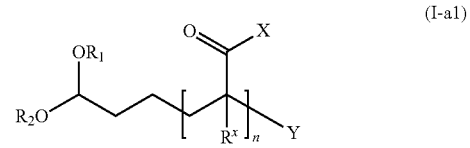

wherein $R_1$, $R_2$, $R^x$, X, Y and n are as defined above and herein.

In certain embodiments, the present disclosure provides conjugates of formula (I-a2):

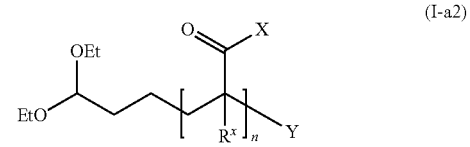

wherein X, Y, $R^x$ and n are as defined above and herein.

In certain embodiments, the present disclosure provides conjugates of formula (I-a3):

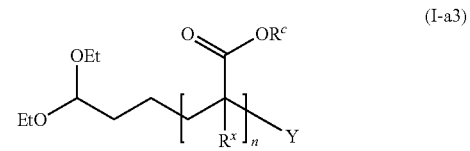

wherein $R^c$, Y, $R^x$ and n are as defined above and herein.

In certain embodiments, the present disclosure provides the conjugates:

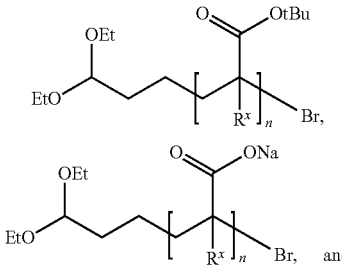

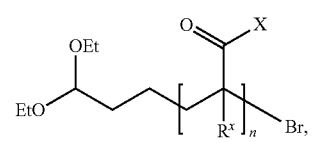

wherein the group:

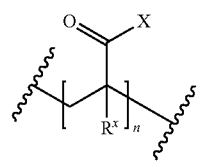

corresponds to a mixture of the groups:

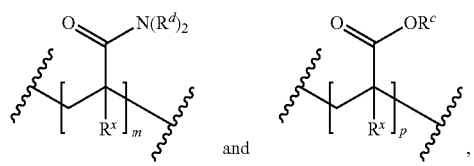

wherein the sum of (m+p) is equal to n, respectively. In certain embodiments, n is 10. In certain embodiments, n is 20.

In certain embodiments, the present disclosure provides conjugates of formula (I-b1):

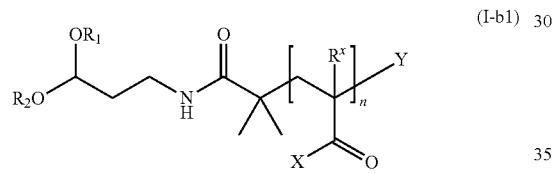

wherein $R_1$, $R_2$, X, Y and $R^x$ and n are as defined above and herein.

In certain embodiments, the present disclosure provides conjugates of formula (I-b2):

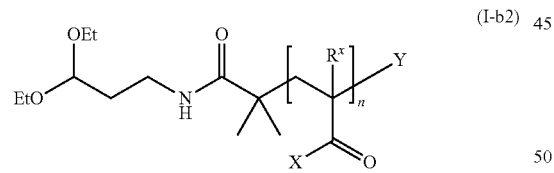

wherein X, Y, $R^x$ and n are as defined above and herein.

In certain embodiments, the present disclosure provides conjugates of formula (I-b3):

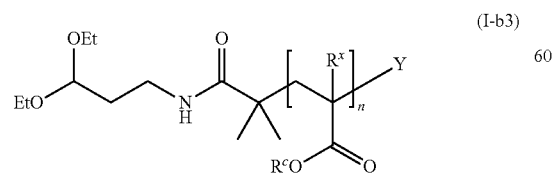

wherein $R^c$, Y, $R^x$ and n are as defined above and herein.

In certain embodiments, the present disclosure provides the conjugates:

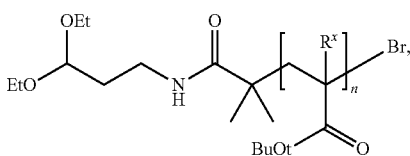

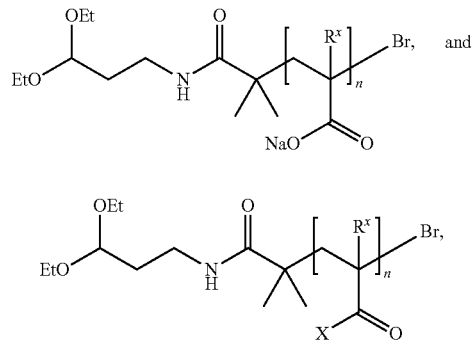

wherein the group:

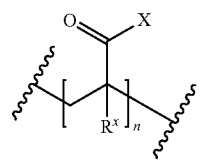

corresponds to a mixture of the groups:

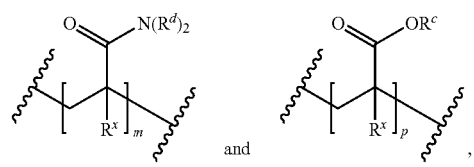

wherein the sum of (m+p) is equal to n, respectively. In certain embodiments, n is 10. In certain embodiments, n is 20.

In certain embodiments, the present disclosure provides conjugates of formula (I-c1):

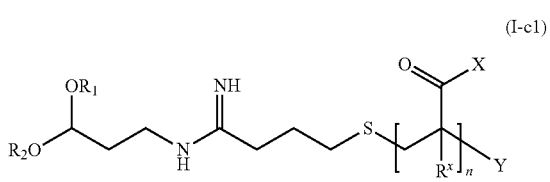

wherein $R_1$, $R_2$, X, Y, $R^x$ and n are as defined above and herein.

In certain embodiments, the present disclosure provides conjugates of formula (I-c2):

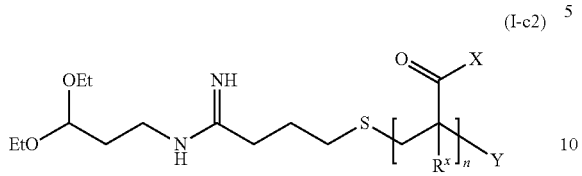

(I-c2)

wherein X, Y, $R^x$ and n are as defined above and herein.

In certain embodiments, the present disclosure provides conjugates of formula (I-c3):

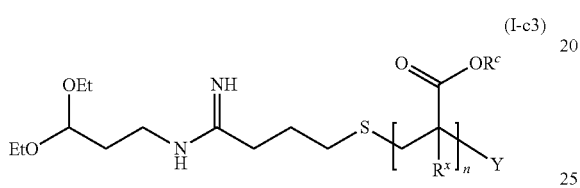

(I-c3)

wherein $R^c$, Y, $R^x$ and n are as defined above and herein.

In certain embodiments, the present disclosure provides the conjugates:

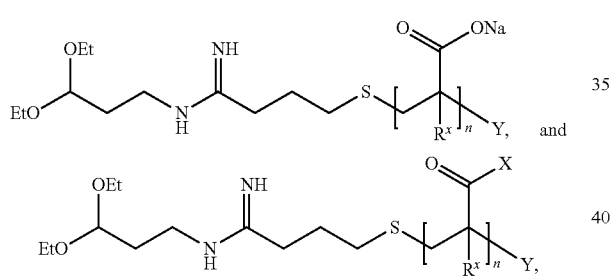

wherein the group:

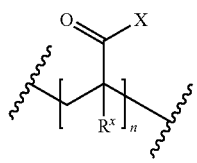

corresponds to a mixture of the groups:

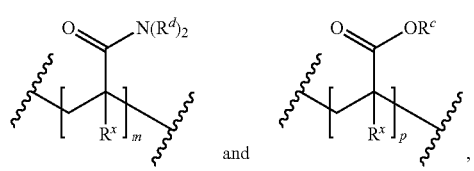

wherein the sum of (m+p) is equal to n, respectively. In certain embodiments, n is 10. In certain embodiments, n is 20.

In certain embodiments, the present disclosure provides conjugates of formulae (II-a1):

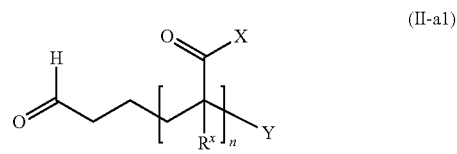

(II-a1)

wherein X, Y, $R^x$ and n are as defined above and herein.

In certain embodiments, the present disclosure provides the conjugates:

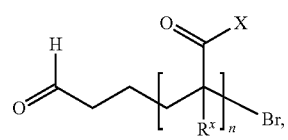

wherein the group:

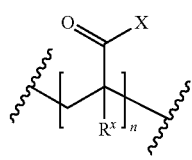

corresponds to a mixture of the groups:

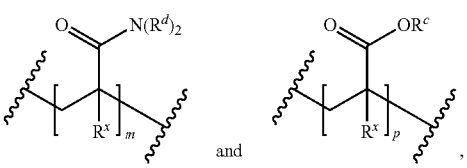

wherein the sum of (m+p) is equal to n, respectively. In certain embodiments, n is 10. In certain embodiments, n is 20.

In certain embodiments, the present disclosure provides conjugates of formula (II-b1):

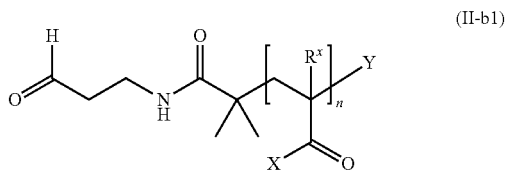

(II-b1)

wherein X, Y, $R^x$ and n are as defined above and herein.

In certain embodiment, the present disclosure provides the conjugates:

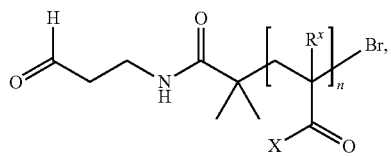

wherein the group:

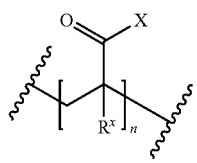

corresponds to a mixture of the groups:

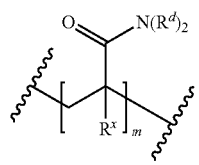 and 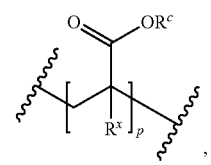, wherein the sum of (m+p) is equal to n, respectively. In certain embodiments, n is 10. In certain embodiments, n is 20.

In certain embodiments, the present disclosure provides conjugates of formula (II-c1):

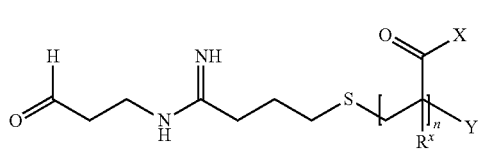

(II-c1)

wherein X, Y, $R^x$ and n are as defined above and herein.

In certain embodiments, the present disclosure provides the conjugates:

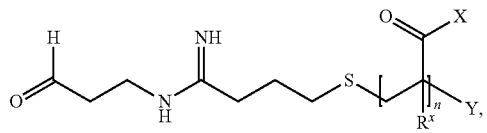

wherein the group:

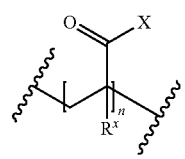

corresponds to a mixture of the groups:

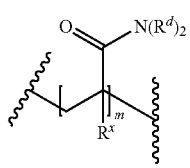 and 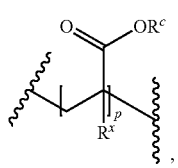, wherein the sum of (m+p) is equal to n, respectively. In certain embodiments, n is 10. In certain embodiments, n is 20.

In certain embodiments, the present disclosure provides conjugates of formulae (III-a1):

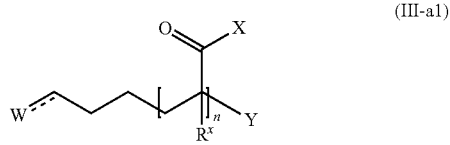

(III-a1)

wherein ------, W, X, Y, $R^x$ and n are as defined above and herein.

In certain embodiments, the present disclosure provides conjugates of formulae (III-a2):

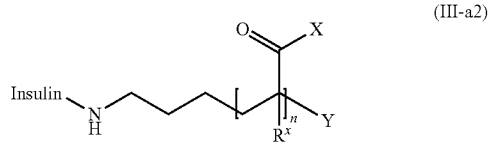

(III-a2)

wherein X, Y, $R^x$ and n are as defined above and herein.

In certain embodiments, the present disclosure provides the conjugates:

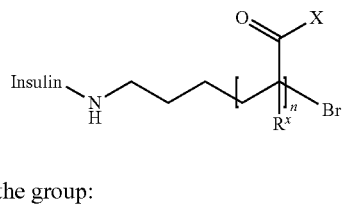

wherein the group:

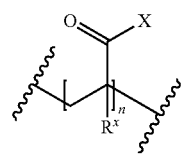

corresponds to a mixture of the groups:

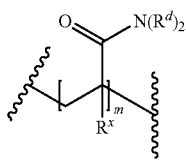 and 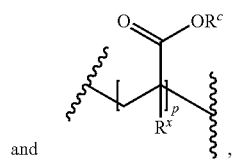, wherein the sum of (m+p) is equal to n, respectively. In certain embodiments, n is 10. In certain embodiments, n is 20.

In certain embodiments, the present disclosure provides conjugates of formula (III-b1):

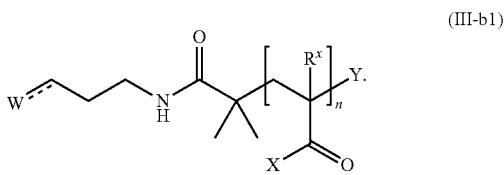

(III-b1)

wherein ------, W, X, Y, $R^x$ and n are as defined above and herein.

In certain embodiments, the present disclosure provides conjugates of formula (III-b2):

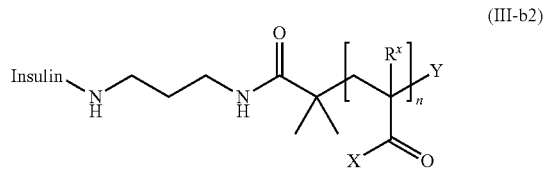

(III-b2)

wherein X, Y, R$^x$ and n are as defined above and herein.

In certain embodiments, the present disclosure provides the conjugates:

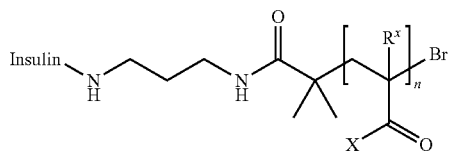

wherein the group:

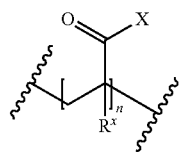

corresponds to a mixture of the groups:

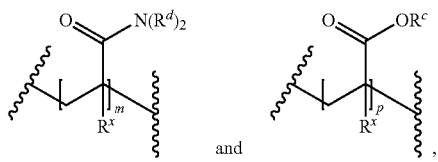

wherein the sum of (m+p) is equal to n, respectively. In certain embodiments, n is 10. In certain embodiments, n is 20.

In certain embodiments, the present disclosure provides conjugates of formula (III-c1):

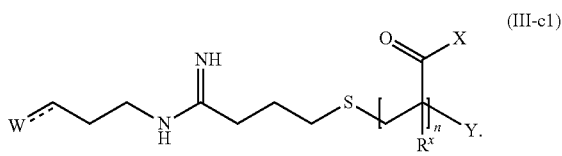

(III-c1)

wherein ===, W, X, Y, R$^x$ and n are as defined above and herein.

In certain embodiments, the present disclosure provides conjugates of formula (III-c2):

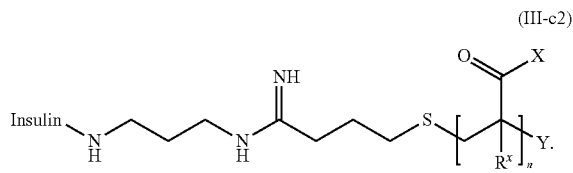

(III-c2)

wherein X, Y, R$^x$ and n are as defined above and herein.

In certain embodiments, the present disclosure provides the conjugates:

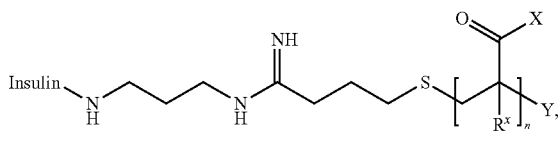

wherein the group:

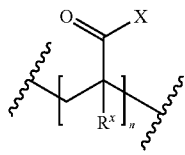

corresponds to a mixture of the groups:

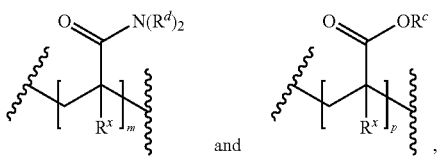

wherein the sum of (m+p) is equal to n, respectively. In certain embodiments, n is 10. In certain embodiments, n is 20.

Characterization of Conjugates

The conjugates of formulae (I), (II) or (III) can be characterized by nuclear magnetic resonance (e.g., $^1$H NMR); gel permeation chromatography (GPC) for molecular weight and polydispersity; and Fourier transform infrared spectroscopy (FTIR) or acid titration for determination of the number of acid groups per chain.

In certain embodiments the conjugate framework (i.e., without including the affinity ligands, drug or detectable label) has a molecular weight of less than 10,000 Da, e.g., in the range of about 100 to about 10,000 Da. In certain embodiments, the conjugate framework has a molecular weight in the range of about 300 to about 5,000 Da. In certain embodiments, the conjugate framework has a molecular weight in the range of about 500 to about 2,500 Da. In certain embodiments, the conjugate framework has a molecular weight in the range of about 1,000 to 2,000 Da. In certain embodiments, the conjugate framework has a molecular weight in the range of about 200 to 1,000 Da. In certain embodiments, the conjugate framework has a molecular weight in the range of about 300 to 800 Da.

In certain embodiments, a mixture of conjugates of formula (I) or (II), or (III) is generated. The conjugates in this mixture may have the same or different molecular weights. In one embodiment, the polydispersity of the mixture is less than 1.5. In one embodiment, the polydispersity of the mixture is less than 1.25.

In certain embodiments, a composition of conjugates of formula (I) is provided with less than 0.1% by weight (based on the overall dry weight of the composition) of an initiating compound, e.g., less than 0.01%. In certain embodiments, a composition is provided with less than 0.1% by weight (based on the overall dry weight of the composition) of a monomer, e.g., less than 0.01%.

In general, the amount of drug (or detectable label) that is loaded onto a conjugate will depend on the molecular weight of the drug (or detectable label) and can be controlled by adjusting the molecular weight of the conjugate framework and/or the level of chemical activation (i.e., when pendant groups are included in the framework). In various embodiments, the drug (or detectable label) loading level may be in the range of 5 to 99% w/w of drug (or detectable label) to conjugate. In various embodiments, loading levels within the narrower range of 50 to 99% may be used, e.g., in the range of 80 to 99%.

Methods of Preparing Conjugates

1. Conjugates of Formula (I)

Conjugates of formula (I) can be prepared by methods known in the art, e.g., for example, see *Polymer Chemistry*, 2$^{nd}$ Edition by Paul C. Hiemenz and Timothy P. Lodge, Published by CRC, 2007 and *Principles of Polymerization*, 4$^{th}$ Edition by George Odian, published by Wiley-Interscience, 2004. In certain embodiments, conjugates of formula (I), or a subset thereof, are prepared via an Atom Transfer Radical Polymerization (ATRP) process. In other embodiments, conjugates of formula (I), or a subset thereof, are prepared via a Free Radical Polymerization Method.

i. Atom Transfer Radical Polymerization (ATRP) Process

In one aspect, the present disclosure provides a method of preparing a conjugate of formula (I),

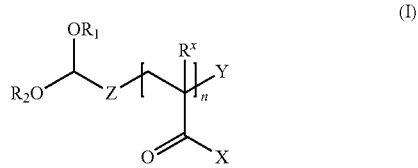
(I)

wherein n, $R_1$, $R_2$, $R^x$, Z, X, Y and Z are as defined herein, comprising the steps of:

(a) providing a mixture of a catalyst, initiating compound and one or more monomers; and (b) polymerizing the mixture to provide a polymer, wherein:

the initiating compound is of the formulae:

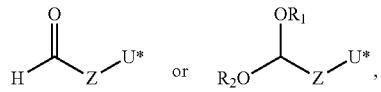

or a mixture thereof, wherein $R_1$ and $R_2$ are as defined herein, and U* is a suitable leaving group; and the monomer(s) is of the formula:

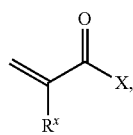

wherein X and $R^x$ are as defined herein.

In certain embodiments, the initiating compound is of the formula:

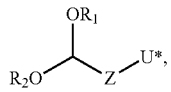

wherein $R_1$ and $R_2$ are as defined herein, and U* is a suitable leaving group.

Suitable U* leaving groups include, but are not limited to, halogen (e.g., Br, Cl, I), —SR$^g$, —OR$^g$, and Si(R$^g$)$_3$, wherein each instance of R$^g$ is independently optionally substituted aliphatic, optionally substituted heteroaliphatic, optionally substituted aryl, or optionally substituted heteroaryl. The initiating compound is designed such that the product contains only one terminal acetal group per conjugate.

In certain embodiments, the initiating compound is of the formulae:

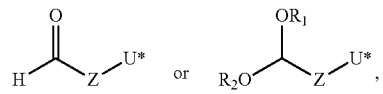

wherein $R_1$ and $R_2$ are as defined herein, and U* is bromine.

In certain embodiments, the initiating compound is of the formula:

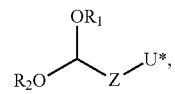

wherein $R_1$ and $R_2$ are as defined herein, and U* is bromine.

In the instance that the initiating compound is provided as a mixture of acetal and aldehyde compounds:

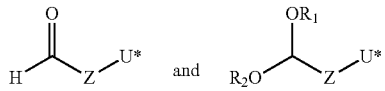

the above method further comprises an additional step (c) of converting any unprotected aldehyde groups to acetal groups present on the product of step (b) to provide a conjugate of formula (I). One of ordinary skill in the art will appreciate that a wide variety of reaction conditions may be employed to promote this transformation, therefore a wide variety of reaction conditions are envisioned; see generally, *March's Advanced Organic Chemistry: Reactions, Mechanisms, and Structure*, M. B. Smith and J. March, 5$^{th}$ Edition, John Wiley & Sons, 2001; *Comprehensive Organic Transformations*, R. C. Larock, 2$^{nd}$ Edition, John Wiley & Sons, 1999; and *Protecting Groups in Organic Synthesis*, T. W. Greene and P. G. M. Wuts, 3$^{rd}$ edition, John Wiley & Sons, 1999. In certain embodiments, the reaction of step (c) is accomplished by treating the product of step (b) with an acid and an alcohol (e.g., HOR$_1$, HOR$_2$). Exemplary acids include hydrochloric, sulfuric, phosphoric, polyphosphoric, methanesulfonic, Eaton's reagent (P$_2$O$_5$/MeSO$_3$H), chlorosulfonic, camphorsulfonic, and p-toluenesulfonic acid. Exemplary alcohols include methanol, ethanol, isopropanol, ethan-1,2-diol, propan-1,3-diol, and the like.

The above method may further comprise additional steps, such as a pH neutralizing step (step d) and/or an ion exchange step (step e).

In certain embodiments, the one or more monomers is of the formula:

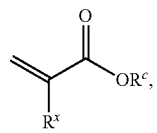

wherein R$^c$ is hydrogen, optionally substituted aliphatic, optionally substituted heteroaliphatic, optionally substituted aryl, optionally substituted heteroaryl, a suitable hydroxyl protecting group or a cation group, and R$^x$ is as defined herein. In certain embodiments, R$^c$ is hydrogen, or an optionally substituted aliphatic group. In certain embodiments, $R^c$ is hydrogen. In certain embodiments, $R^c$ is an optionally substituted aliphatic group.

In certain embodiments, step (a) provides a single monomer. In certain embodiments, step (a) provides two (types of) monomers.

Exemplary monomers include, but are not limited to, acrylic acid (wherein X is —OH and $R^x$ is H), tert-butyl acrylate (wherein X is —OtBu and $R^x$ is H), isopropyl acrylate (wherein X is -OiPr and $R^x$ is H), methacrylate (wherein X is —OMe, and $R^x$ is H), tert-butyl methacrylate (wherein X is -OtBu, and $R^x$ is —CH$_3$), and isopropylmethacrylate (wherein X is -OiPr, and $R^x$ is —CH$_3$). In certain embodiments, at least one of the monomers of step (a) is selected from acrylic acid, tert-butyl acrylate, isopropyl acrylate, methacrylate, or tert-butyl methacrylate, and isopropylmethacrylate. In certain embodiments, step (a) includes a single monomer selected from acrylic acid, tert-butyl acrylate, isopropyl acrylate, methacrylate, or tert-butyl methacrylate, and isopropylmethacrylate. In certain embodiments, the monomer is acrylic acid or tert-butyl acrylate. In certain embodiments, the monomer is acrylic acid. In certain embodiments, the monomer is tert-butyl acrylate.

In certain embodiments, the catalyst of step (a) is a metal catalyst. In certain embodiments, the metal catalyst of step (a) is a transition metal catalyst. In certain embodiments, the transition metal catalyst of step (a) is a copper catalyst. In certain embodiments, the copper catalyst is CuCl, CuBr, CuI, CuBr$_2$ or CuCl$_2$.

In certain embodiments, the reagents in step (a) further comprise a ligand. Exemplary ligands include, but are not limited to, N,N,N',N'',N''-pentamethyldiethylenetriamine (PMDETA), tris[2-(dimethylamino)ethyl]amine (Me$_6$TREN), tris[(2-pyridyl)methyl]amine (TPMA), 4,4'-di-(5-nonyl)-2,2'-dipyridyl (dNbpy) or N-(pyridin-2-ylmethylene)octan-1-amine. In certain embodiments, the ligand is PMDETA or N-(pyridin-2-ylmethylene)octan-1-amine.

In certain embodiments, the step (b) further comprises heating the mixture. In certain embodiments, the step (b) further comprises heating the mixture in a range from about 35° C. to about 100° C. In certain embodiments, the step (b) further comprises heating the mixture in a range from about 40° C. to about 90° C.

ii. Free Radical Polymerization Method

In another aspect, the present disclosure provides a method of preparing a conjugate of formula (I), (I)

wherein n, R$_1$, R$_2$, R$^x$, Z, X, Y and Z are as defined herein, comprising the steps of:

(a) providing a mixture of a free radical initiator and one or more monomers;
(b) polymerizing the mixture; and
(c) adding a chain terminating agent to provide a polymer; wherein:

the monomer(s) are of the formula:

wherein X and $R^x$ are as defined herein; and the chain terminating agent is a compound of the formulae:

or a mixture thereof, wherein Q is selected from —SH, —OH or —NH$_2$.

In certain embodiments, the one or more monomers is of the formula:

wherein $R^c$ is hydrogen, optionally substituted aliphatic, optionally substituted heteroaliphatic, optionally substituted aryl, optionally substituted heteroaryl, a suitable hydroxyl protecting group or a cation group. In certain embodiments, $R^c$ is hydrogen, or an optionally substituted aliphatic group. In certain embodiments, $R^c$ is hydrogen. In certain embodiments, $R^c$ is an optionally substituted aliphatic group.

In certain embodiments, step (a) provides a single monomer. In certain embodiments, step (a) provides two (types of) monomers.

Exemplary monomers include, but are not limited to, acrylic acid (wherein X is —OH and $R^x$ is H), tert-butyl acrylate (wherein X is -OtBu and $R^x$ is H), isopropyl acrylate (wherein X is -OiPr and $R^x$ is H), methacrylate (wherein X is —OMe, and $R^x$ is H), tert-butyl methacrylate (wherein X is -OtBu, and $R^x$ is —CH$_3$), and isopropylmethacrylate (wherein X is -OiPr, and $R^x$ is —CH$_3$). In certain embodiments, at least one of the monomers of step (a) is selected from acrylic acid, tert-butyl acrylate, isopropyl acrylate, methacrylate, or tert-butyl methacrylate, and isopropylmethacrylate. In certain embodiments, step (a) includes a single monomer selected from acrylic acid, tert-butyl acrylate, isopropyl acrylate, methacrylate, or tert-butyl methacrylate, and isopropylmethacrylate. In certain embodiments, the monomer is acrylic acid or tert-butyl acrylate. In certain embodiments, the monomer is acrylic acid. In certain embodiments, the monomer is tert-butyl acrylate.

In certain embodiments, the chain terminating agent is a compound of the formulae:

or a mixture thereof, wherein Q is selected from —SH.

In certain embodiments, the chain terminating agent is a compound of the formula:

or a mixture thereof, wherein Q is selected from —SH.

In the instance that the chain terminating agent is provided as a mixture of acetal and aldehyde:

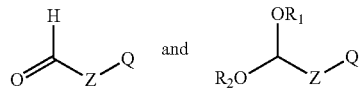

the above method further comprises an additional step (d) of converting any unprotected aldehyde groups to acetal groups present on the product of step (c) to provide a conjugate of formula (I). One of ordinary skill in the art will appreciate that a wide variety of reaction conditions may be employed to promote this transformation, therefore a wide variety of reaction conditions are envisioned; see generally, *March's Advanced Organic Chemistry: Reactions, Mechanisms, and Structure*, M. B. Smith and J. March, $5^{th}$ Edition, John Wiley & Sons, 2001; *Comprehensive Organic Transformaions*, R. C. Larock, $2^{nd}$ Edition, John Wiley & Sons, 1999; and *Protecting Groups in Organic Synthesis*, T. W. Greene and P. G. M. Wuts, $3^{rd}$ edition, John Wiley & Sons, 1999. In certain embodiments, the reaction of step (c) is accomplished by treating the product of step (b) with an acid and an alcohol (e.g., $HOR_1$, $HOR_2$). Exemplary acids include hydrochloric, sulfuric, phosphoric, polyphosphoric, methanesulfonic, Eaton's reagent ($P_2O_5$/$MeSO_3H$), chlorosulfonic, camphorsulfonic, and p-toluenesulfonic acid. Exemplary alcohols include methanol, ethanol, isopropanol, ethan-1,2-diol, propan-1,3-diol, and the like.

The above method may further comprise additional steps, such as a pH neutralizing step (step e) and/or an ion exchange step (step f).

In certain embodiments, the free radical initiator is a photoinitiator, and step (b) includes exposure of the reaction mixture to light to induce polymerization. In certain embodiments, the free radical initiator is a thermal initiator, and step (b) includes heating of the reaction mixture to induce polymerization.

Exemplary photoinitiators include Acetophenone, Diphenyl(2,4,6-trimethylbenzoyl)phosphine oxide, 4,4'-Dimethoxybenzoin, Anthraquinone, Anthraquinone-2-sulfonic acid Sodium salt, Benzene-chromium(0) tricarbonyl, 4-(Boc-aminomethyl)phenyl isothiocyanate, Benzoin, Benzoin ethyl ether, Benzoin isobutyl ether, Benzoin methyl ether, Benzophenone, Benzophenone-3,3',4,4'-tetracarboxylic dianhydride, 4-Benzoylbiphenyl, 2-Benzyl-2-(dimethylamino)-4'-morpholinobutyrophenone, 4,4'-Bis(diethylamino)benzophenone, (±)-Camphorquinone, 2-Chlorothioxanthen-9-one, 5-Dibenzosuberenone, 2,2-Diethoxyacetophenone, 4,4'-Dihydroxybenzophenone, 2,2-Dimethoxy-2-phenylacetophenone, 4-(Dimethylamino)benzophenone, 4,4'-Dimethylbenzil, 3,4-Dimethylbenzophenone, 4'-Ethoxyacetophenone, 2-Ethylanthraquinone, Ferrocene, 3'-Hydroxyacetophenone, 4'-Hydroxyacetophenone, 3-Hydroxybenzophenone, 4-Hydroxybenzophenone, 1-Hydroxycyclohexyl phenyl ketone, 2-Hydroxy-2-methylpropiophenone, 2-Methylbenzophenone, 3-Methylbenzophenone, 9,10-Phenanthrenequinone, 4'-Phenoxyacetophenone, Thioxanthen-9-one, Triarylsulfonium hexafluorophosphate salts, 3-Mercapto-1-propanol, 11-Mercapto-1-undecanol, 1-Mercapto-2-propanol and 3-Mercapto-2-butanol.

Exemplary thermal initiators include 4,4'-Azobis(4-cyanovaleric acid) (VASO 68), 1,1'-Azobis(cyclohexanecarbonitrile) (ACBN), 2,2'-Azobis(2-methylpropionitrile) (AIBN), Benzoyl peroxide, 2,2-Bis(tert-butylperoxy)butane, 2,5-Bis(tert-butylperoxy)-2,5-dimethylhexane, tert-Butyl hydroperoxide, tert-Butyl peracetate, Cumene hydroperoxide, tert-Butyl peroxybenzoate, Lauroyl peroxide and Dicumyl peroxide.

In certain embodiments, the free radical initiator is a thermal initiator. In certain embodiments, the free radical initiator is a thermal initiator selected from 4,4'-Azobis(4-cyanovaleric acid) (VASO 68), 1,1'-Azobis(cyclohexanecarbonitrile) (ACBN) and 2,2'-Azobis(2-methylpropionitrile) (AIBN). In certain embodiments, the free radical initiator is 4,4'-Azobis (4-cyanovaleric acid) (VASO 68).

In certain embodiments, the step (b) further comprises heating the mixture. In certain embodiments, the step (b) further comprises heating the mixture in a range from about 35° C. to about 100° C. In certain embodiments, the step (b) further comprises heating the mixture in a range from about 40° C. to about 90° C. In certain embodiments, the step (b) further comprises heating the mixture in a range from about 40° C. to about 70° C. In certain embodiments, the step (b) further comprises heating the mixture to about 60° C.

2. Modification of Conjugates of Formula (I) and Conjugates of Formulae (II) and (III)

It will be appreciated that conjugates of formula (I) can be prepared from an acid monomer (wherein X is OH), and the resulting conjugate may be treated with a suitable base (e.g., LiOH, NaOH, KOH, and the like) to provide a partial or fully converted salt of that conjugate (wherein X is $OR^c$, and $R^c$ is H or a cation), e.g., a sodium (Na) salt.

In general, any number of groups along the polymer chain can be in acid or salt form. For example, a conjugate of formula (I) may include 1, 2, 3, 4, 5, 6, 7, 8, 9, 10 or more —$CO_2H$ groups. In one embodiment, a sodium salt form is produced with at least 50% conversion of acid —$CO_2H$ groups to sodium salt. In one embodiment, a sodium salt form is produced with at least 60% conversion of acid —$CO_2H$ groups to sodium salt. In one embodiment, a sodium salt form is produced with at least 70% conversion of acid —$CO_2H$ groups to sodium salt. In one embodiment, a sodium salt form is produced with at least 80% conversion of acid —$CO_2H$ groups to sodium salt. In one embodiment, a sodium salt form is produced with at least 90% conversion of acid groups to sodium salt. In one embodiment, a sodium salt form is produced with 100% conversion of acid groups to sodium salt.

Thus, in one aspect, the present disclosure provides a method of preparing a conjugate of the formula:

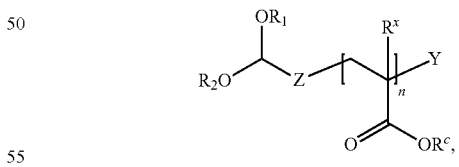

wherein n, $R_1$, $R_2$, $R^x$, Z, Y and Z are as defined herein, and wherein each instance of $R^c$ is independently a hydrogen or a cation, with the proviso that every instance of $R^c$ cannot be hydrogen, comprising the steps of:

(a) providing a conjugate as detailed above via the Free Radical Polymerization Method or ATRP method, wherein X is —$OR^c$ and $R^c$ is hydrogen, optionally substituted aliphatic, optionally substituted heteroaliphatic, optionally substituted aryl, or optionally substituted heteroaryl; and (b) treating the conjugate with a suitable base.

It will also be appreciated that the —C(=O)X groups provided along the polymeric chain may react with one or more compounds bearing nucleophilic groups (e.g., hydroxyl groups, amino groups) in order to covalently conjugate such compounds along the polymeric chain.

For example, in certain embodiments, the —C(=O)X groups provided along the polymeric chain may react with affinity ligands (e.g., saccharides or amino saccharides) in order to provide —C(=O)OR$^c$ or —C(=O)NHR$^d$ pendant groups, wherein R$^c$ and R$^d$ are affinity ligands as defined above and herein.

Figure 4:
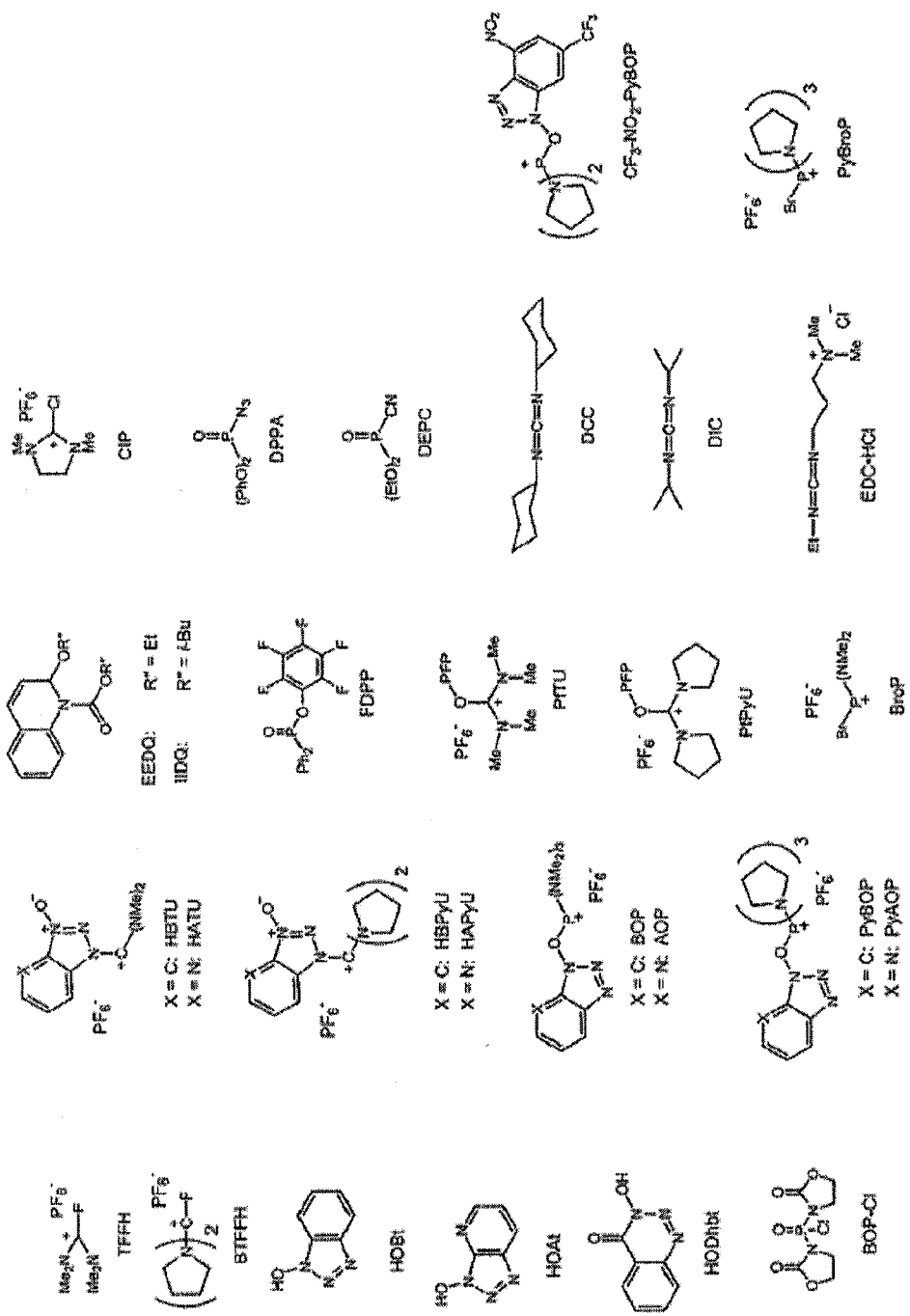
FIG. 4: is a schematic which shows exemplary peptide coupling reagents.

In certain embodiments, covalent conjugation of an affinity ligand to a —C(=O)X group provided along the polymeric chain is achieved by reacting a coupling agent, an affinity ligand with at least one free hydroxyl (—OH) or free amino (—NH$_2$) group, and a conjugate with at least one pendant —CO$_2$H group together. In certain embodiments, the coupling agent is a peptide coupling agent. Exemplary peptide coupling agents include, but are not limited to, DCC, BOP, BrOP, AOP, PyBOP, PyAOP, PyBroP, PyCloP, HBTU, HATU, EDC/HOBT, or 1-ethyl-3-(3-dimethylaminopropyl)-carbodiimide (EDAC). Other exemplary peptide coupling reagents are provided in FIG. 4.

Thus, in another aspect, the present disclosure provides a method of preparing a conjugate of the formula:

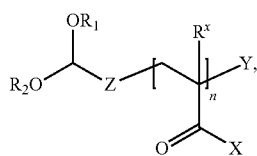

wherein the group:

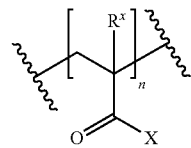

provided in the above formula corresponds to a mixture of the groups:

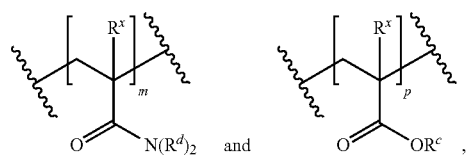

wherein the sum of (m+p) is equal to n;
and wherein R$_1$, R$_2$, Z, R$^x$, X, Y, m, n, and p are as described above and herein,
comprising the steps of:
(a) providing a conjugate as detailed above via the Free Radical Polymerization Method or ATRP method, wherein X is OR$^c$, and R$^c$ is hydrogen, optionally substituted aliphatic, optionally substituted heteroaliphatic, optionally substituted aryl, optionally substituted heteroaryl, or a cation group; and
(b) treating the conjugate with a compound HN(R$^d$)$_2$, wherein each R$^d$ is, independently, hydrogen, optionally substituted aliphatic, optionally substituted heteroaliphatic, optionally substituted aryl, optionally substituted heteroaryl, a suitable amino protecting group, or an affinity ligand.

Polymers of formula (II) may be prepared from any of the polymers of formula (I), as described above and herein, by removing the acetal moiety under suitable deprotection conditions (e.g., acid catalyzed) to provide the free aldehyde (—CHO) moiety. One of ordinary skill in the art will appreciate that a wide variety of reaction conditions may be employed to promote this transformation, therefore a wide variety of reaction conditions are envisioned; see generally, *March's Advanced Organic Chemistry: Reactions, Mechanisms, and Structure*, M. B. Smith and J. March, 5$^{th}$ Edition, John Wiley & Sons, 2001; *Comprehensive Organic Transformaions*, R. C. Larock, 2$^{nd}$ Edition, John Wiley & Sons, 1999; and *Protecting Groups in Organic Synthesis*, T. W. Greene and P. G. M. Wuts, 3$^{rd}$ edition, John Wiley & Sons, 1999. In certain embodiments, the acetal is removed by treating the conjugate of formula (I) with an acid. Exemplary acids include hydrochloric, sulfuric, phosphoric, polyphosphoric, methanesulfonic, Eaton's reagent (P$_2$O$_5$/MeSO$_3$H), chlorosulfonic, camphorsulfonic, and p-toluenesulfonic acid.

Thus, in another aspect, the present disclosure provides a method of preparing a conjugate of formula (II):

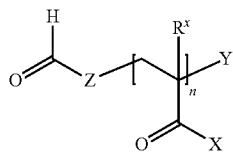

wherein R$^x$, X, Y, Z and n are as defined above and herein; comprising the steps of:
(a) providing a conjugate of formula (I):

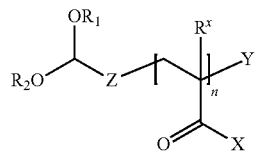

wherein n, R$_1$, R$_2$, R$^x$, Z, X, Y and Z are as defined herein; and
(b) treating the conjugate under suitable deprotection conditions to provide a conjugate of formula (II).

Conjugates of formula (III) may be prepared by covalently conjugating a drug or a detectable label to a conjugate of formula (II). In certain embodiments, this coupling reaction is achieved via reaction of a nucleophilic group (e.g., hydroxyl group, amino group, thiol group) present on a drug or detectable label with the terminal aldehyde moiety present on the conjugate of formula (II). In certain embodiments, the drug (or detectable label) has at least one free amino group, and the drug (or detectable label) is coupled to the conjugate of formula (II) via reductive amination.

For example, the drug may be an insulin molecule, or a protected form thereof (e.g., where some amines in the insulin molecule are protected to selectively react a given insulin residue to the polymer), and a free amine group present on the insulin molecule may react (via reductive amination) with the terminal aldehyde moiety of the conjugate of formula (II) to provide a conjugate of formula (III). One of ordinary skill in the art will appreciate that a wide variety of reaction conditions may be employed to promote this transformation, therefore a wide variety of reaction conditions are envisioned; see generally, *March's Advanced Organic Chemistry: Reactions, Mechanisms, and Structure*, M. B. Smith and J. March, 5$^{th}$ Edition, John Wiley & Sons, 2001; *Comprehensive Organic Transformaions*, R. C. Larock, 2$^{nd}$ Edition, John Wiley & Sons, 1999; and *Protecting Groups in Organic Synthesis*, T. W. Greene and P. G. M. Wuts, 3$^{rd}$ edition, John Wiley & Sons, 1999. In certain embodiments, the reductive amination step is conducted at room temperature. In certain embodiments, the reductive amination step is conducted with sodium cyanoborohydride (NaBH$_3$CN) or sodium triacetoxyborohydride (NaBH(OCOCH$_3$)$_3$). In certain embodiments, the reductive amination is a two step procedure involving imine formation, followed by reduction (e.g., NaBH$_4$, by hydrogenation, etc.).

Thus, in yet another aspect, the present disclosure provides a method of preparing a conjugate of formula (III):

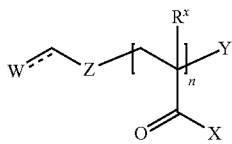

wherein -----, W, Z, R$^x$, X, Y and n are as defined above and herein;

comprising the steps of:

(a) providing a conjugate of formula (II):

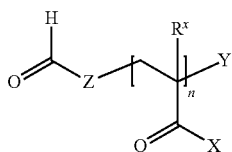

(II)

wherein R$^x$, X, Y, Z and n are as defined above and herein;

(b) providing a drug or detectable label comprising at least one free amino group; and (c) coupling the amino group with the aldehyde via reductive amination to provide a conjugate of formula (III).

In certain embodiments, the method further comprises removing non-covalently bound drug or detectable label (step d). In certain embodiments, this purification step (i.e., the step of removing) is a chromatographic purification (e.g., by reverse phase chromatography, ion exchange chromatography, and/or size exclusion chromatography). In certain embodiments, reverse phase chromatography is used to remove non-covalently bound drug or detectable label. In certain embodiments, ion exchange chromatography is used to remove non-covalently bound drug or detectable label. In certain embodiments, size exclusion chromatography is used to remove non-covalently bound drug or detectable label.

Multivalent Cross-Linking Agents

In one aspect, the present disclosure provides cross-linked materials that have been prepared by combining an inventive conjugate with a multivalent cross-linking agent. The following sections describe exemplary cross-linking agents that can be used for this purpose.

Figure 10:
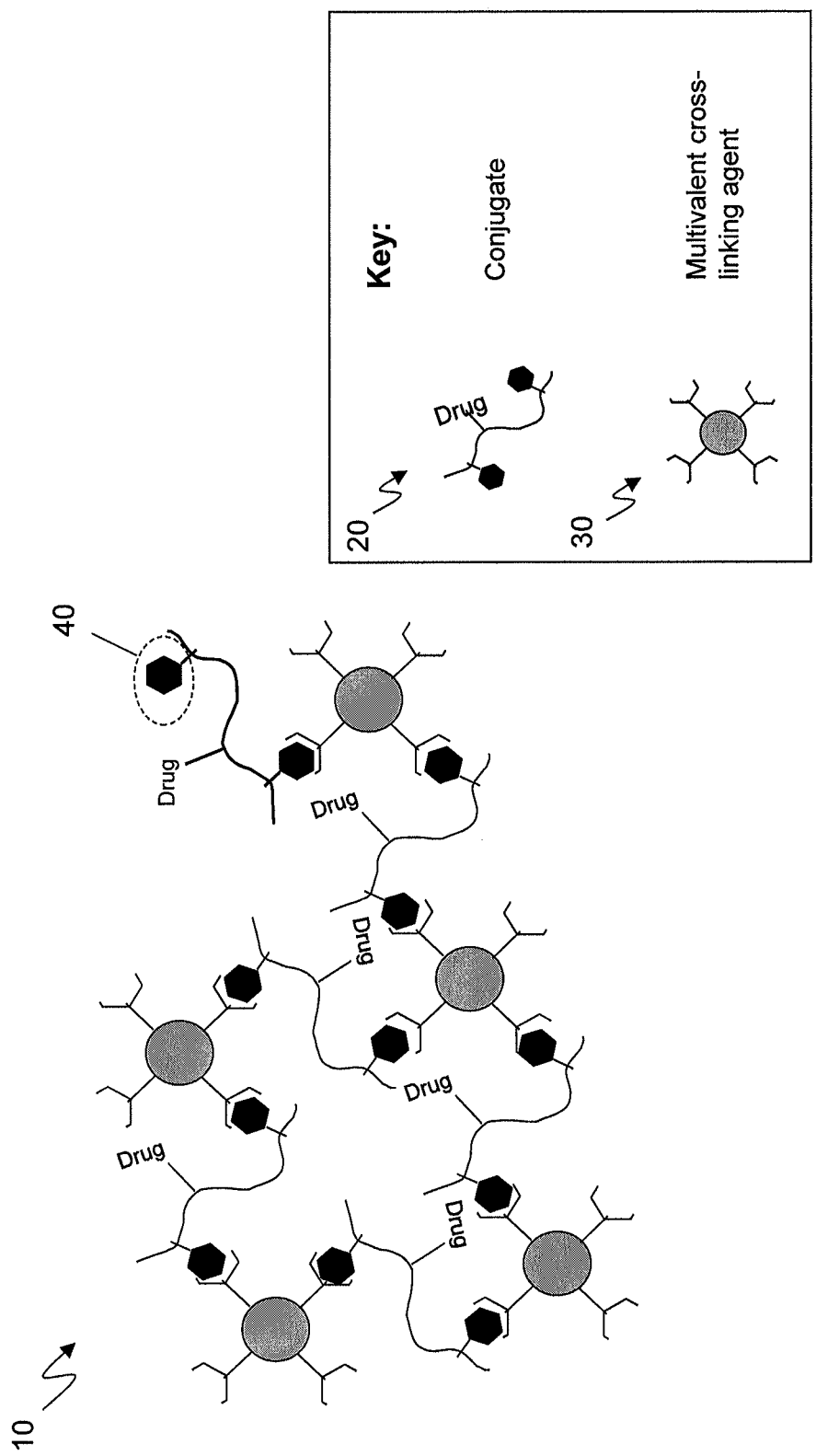
FIG. 10: is a schematic of a cross-linked material 10 which is capable of controllably releasing conjugates 20 in response to a target molecule (e.g., glucose). The materials are prepared by combining the conjugates 20 with multivalent cross-linking agents 30 that non-covalently bind the affinity ligands 40 of the conjugates 20 and thereby cross-link the conjugates 20 to form the cross-linked material 10. The non-covalent bonds between the multivalent cross-linking agents 30 and the affinity ligands 40 are competitively dissociated in the presence of excess amounts of the target molecule (e.g., glucose).

As discussed in more detail below and as illustrated in FIG. 10, the cross-linked material 10 is capable of controllably releasing the conjugates 20 in response to a target molecule (e.g., glucose). The materials are prepared by combining the conjugates 20 with multivalent cross-linking agents 30 that non-covalently bind the affinity ligands 40 of the conjugates 20 and thereby cross-link the conjugates 20 to form the cross-linked material 10. The non-covalent bonds between the multivalent cross-linking agents 30 and the affinity ligands 40 are competitively dissociated in the presence of excess amounts of the target molecule (e.g., glucose).

1. Polypeptide Cross-Linking Agents

In various embodiments, the multivalent cross-linking agents may include a polypeptide. As discussed in more detail below, suitable multivalent polypeptides exist in nature (e.g., various lectins) but can also be constructed by linking multiple monovalent binding proteins, e.g., monovalent lectins, peptide aptamers, antibodies, cell membrane receptors, etc. Still other multivalent polypeptides may be constructed by chemically linking binding fragments of these proteins.

A variety of mono- and multivalent ligand-binding proteins are available commercially (e.g., from Sigma-Aldrich), including a number of lectins, folate-binding protein, thyroxine-binding globulin, lactoferrin, etc. DeWolf and Best provide a review of ligand-binding proteins including biotin-binding proteins, lipid-binding proteins/transporters of hydrophobic molecules, bacterial periplasmic binding proteins, lectins, serum albumins, immunoglobulins, inactivated enzymes, odorant-binding proteins, immunosuppressant-binding proteins, and phosphate- and sulfate-binding proteins (see De Wolfe and Best, *Pharm. Rev.* 52: 207-236, 2000 and references cited therein). The cell membrane receptors for a variety of hormones have also been described in the art. In certain embodiments, mono- or multivalent binding proteins can be synthesized by rational computational design followed by site directed mutagenesis of existing ligand-binding proteins as described in Looger et al., *Nature* 423:185-190, 2003. Exemplary protein fragments include truncated MBP (Eda et al., *Biosci. Biotechnol. Biochem.*, 62:1326-1331, 1998), truncated conglutinin (Eda et al., *Biochem. J.* 316:43, 1996), truncated SP-D (Eda et al., *Biochem. J.* 323:393, 1997), and the glucose/galactose binding protein of *E. Coli* (Salins et al., *Analytical Biochemistry* 294:19-26, 2001).

a. Lectins

In certain embodiments, mono- or multivalent lectins may be included in a multivalent cross-linking agent. As discussed in more detail below, in certain embodiments, it may be advantageous to chemically modify the lectins. Lectins are particularly suitable for use in materials which are designed to respond to a saccharide target molecule (e.g., glucose). Lectins have been isolated from a variety of natural sources including seeds, roots, bark, fungi, bacteria, seaweed, sponges, mollusks, fish eggs, body fluids of invertebrates and lower vertebrates, and mammalian cell membranes (e.g., see *The Lectins: Properties, Functions, and Applications in Biology and Medicine*, Edited by Liener et al., Academic Press, 1986). A number of lectins have also been produced recombinantly (e.g., see Streicher and Sharon, *Methods Enzymol.* 363:47-77, 2003 and US 2006/0247154). As noted above, lectins bind saccharides and polysaccharides with a high degree of specificity. For example, some lectins will bind only to mannose or glucose residues, while others only recognize galactose residues. Some lectins require that the particular residue be in a terminal position, while others bind to residues within a polysaccharide chain. Some lectins require specific anomeric structures and yet others recognize specific sugar sequences. The structures and properties of lectins have been extensively described in the literature. For recent reviews see *Lectins*, Edited by Sharon and L is, Kluwer Academic Publishers, 2003; *Handbook of Animal Lectins: Properties and Biomedical Applications*, Edited by Kilpatrick, Wiley, 2000; and *Handbook of Plant Lectins: Properties and Biomedical Applications*, Edited by Van Damme et al., Wiley, 1998. Exemplary lectins include calnexin, calreticulin, CD22, CD33, galectin (galactose-binding lectin), myelin-associated glycoprotein, N-acetylglucosamine receptor, selectin, sialoadhesin, aggrecan, asialoglycoprotein receptor, CD94, collectin (mannose-binding lectin), mannose receptor, versican, abrin, ricin, concanavalin A, phytohaemagglutinin, and pokeweed mitogen. In various embodiments, human analogs of plant lectins may be used. These include, without limitation, human mannan binding protein (MBP, also called mannan binding lectin, Sheriff et al., *Structural Biology*, 1:789-794 (1994); Dumestre-Perard et al., *Molecular Immunology*, 39:465-473 (2002)), human pulmonary surfactant protein A (SP-A, Allen, et al., *Infection and Immunity*, 67:4563-4569 (1999)), human pulmonary surfactant protein D (SP-D, Persson et al., *The Journal of Biological Chemistry*, 265:5755-5760 (1990)), CL-43 (a human serum protein), and conglutinin.

b. Peptide Aptamers

In certain embodiments monovalent peptide aptamers may be included in a multivalent cross-linking agent. As is well known in the art, peptide aptamers consist of a variable ligand-binding peptide loop fused within a protein scaffold (e.g., see Hoppe-Seyler and Butz, *J. Mol. Med.* 78:426-430, 2000 and Crawford et al., *Briefings in Functional Genomics and Proteomics* 2:72-79, 2003). The variable loop typically includes between about 10 and 20 amino acids. A variety of scaffold proteins may be used. In general, the site of insertion is chosen such that the peptide loop disrupts a region of the scaffold that would otherwise mediate some wild-type function, e.g., the bacterial protein thioredoxin-A in which the variable loop is inserted within the reducing active site (a -Cys-Gly-Pro-Cys- loop in the wild-type protein). Peptide aptamers with suitable affinity for the target molecule can be prepared and selected using any known method. For example, yeast two-hybrid libraries, yeast expression libraries, bacterial expression libraries and/or retroviral libraries for expression in mammalian cells may be used.

In various embodiments, peptide aptamers may be selected by affinity chromatography. According to such embodiments, peptide aptamers in a library are exposed to the target molecule and those that do not bind the target are removed. The bound peptide aptamers are then eluted and cloned for subsequent rounds of selection. A new library is then generated from one or more of these peptide aptamers (e.g., the peptide aptamer with the highest affinity for the target molecule in the first round of selection) and the stringency of the elution conditions is increased or modified to identify peptide aptamers with the desired binding affinity and/or specificity. In various embodiments, the selection process may involve steps in which the stringency of the elution conditions are gradually increased in order to select peptide aptamers with high affinity for the target molecule. In various embodiments, the selection process may involve steps in which the elution conditions are modified (e.g., by using a different affinity column) in order to select peptide aptamers with desired specificity for the target molecule. In various embodiments the selection process may generate a collection of sublibraries (or "pools") each of which comprises peptide aptamers with similar affinities and/or specificities for the target molecule. In various embodiments the selection process may generate a single peptide aptamer sequence (or "monoclonal"). It will be appreciated that any of these peptide aptamer sequences may be cloned for future recombinant expression.

c. Generating Multivalent Cross-Linking Agents

Multivalent cross-linking agents can be generated by covalently or non-covalently linking two or more monovalent binding proteins into a single construct. Typically, two or more proteins (which may have the same or different sequences) may be linked directly to one another (e.g., via a coupling agent) or indirectly through a framework. In various embodiments 2, 3, 4, 5, 6, 7 or 8 or more proteins may be combined into a single construct. In various embodiments the 2, 3, 4, 5, 6, 7 or 8 or more proteins may have the same sequence. It will be appreciated that either one of these approaches may require the proteins to be chemically modified (e.g., to include pendant reactive groups) prior to coupling. It will also be appreciated that the multivalent cross-linking agents of the present disclosure are not limited to a particular coupling reaction or framework (e.g., they can be prepared using frameworks that include polymeric and/or non-polymeric structures). It will further be appreciated that the frameworks may be linear, branched, hyperbranched and/or a combination of these.

In various embodiments the monovalent binding proteins are covalently linked to each other or a framework. In such embodiments, the proteins can be directly linked (i.e., with no intervening chemical groups) or indirectly linked through a spacer (e.g., a coupling agent or covalent chain that provides some physical separation between the proteins or between the proteins and framework). It is to be understood that proteins may be covalently linked to each other or a framework through any number of chemical linkages, including but not limited to amide, ester, ether, isourea, and imine bonds.

In various embodiments, two or more monovalent binding proteins can be non-covalently linked to each other or to a framework. In certain embodiments, the dissociation constant ($K_d$) of the non-covalent linkage in human serum is less than 1 pmol/L. For example, proteins may be non-covalently linked to each other or a framework via a non-covalent ligand-receptor pair as is well known in the art (e.g., without limitation a biotin-avidin based pair). In such an embodiment, one member of the ligand receptor-pair is covalently linked to one protein while the other member of the pair is covalently linked to the other protein or framework. When the proteins (or proteins and framework) are combined, the strong non-covalent interaction between the ligand and its receptor causes the proteins to become non-covalently linked to each other (or the framework). Typical ligand/receptor pairs include protein/cofactor and enzyme/substrate pairs. Besides the commonly used biotin/avidin pair, these include without limitation, biotin/streptavidin, digoxigenin/anti-digoxigenin, FK506/FK506-binding protein (FKBP), rapamycin/FKBP, cyclophilin/cyclosporin and glutathione/glutathione transferase pairs. Other suitable ligand/receptor pairs would be recognized by those skilled in the art, e.g., monoclonal antibodies paired with a epitope tag such as, without limitation, glutathione-S-transferase (GST), c-myc, FLAG® and further those described in Kessler pp. 105-152 of *Advances in Mutagenesis* Ed. by Kessler, Springer-Verlag, 1990; *Affinity Chromatography: Methods and Protocols* (*Methods in Molecular Biology*) Ed. by Pascal Baillon, Humana Press, 2000; and *Immobilized Affinity Ligand Techniques* by Hermanson et al., Academic Press, 1992.

2. Polynucleotide Cross-Linking Agents

In various embodiments, the multivalent cross-linking agents may include a polynucleotide aptamer. The polynucleotide aptamers bind the target molecule and are multivalent (i.e., capable of binding more than one target molecule). In general, monovalent aptamers will first be generated based on their binding properties for the target molecule. As is well known in the art, aptamers to a variety of target molecules can be generated through a process of in vitro selection. See Ellington and Szostak (1990) Nature 346:818; Tuerk and Gold (1990) Science 249:505; and U.S. Pat. No. 5,582,981. See also the glucose binding polynucleotide aptamers that are described in U.S. Provisional Application No. 61/162,092 filed on Mar. 20, 2009 and corresponding PCT application filed on Jan. 27, 2010, each of which is incorporated herein by reference.

Typically, the process begins with the synthesis of a library consisting of randomly generated polynucleotide sequences of fixed length flanked by constant 5' and 3' ends that serve as primers. In certain embodiments (e.g., when optimizing an aptamer) one might start with a sequence which is known to bind the target molecule and generate a library which includes a collection of polynucleotides which exhibit a limited range of changes from the starting sequence (e.g., a random set of single mutations). The sequences in the library are then exposed to the target molecule and those that do not bind the target are removed (e.g., by affinity chromatography). The bound sequences are then eluted and amplified (e.g., by cloning and subsequent transcription or by PCR) to prepare for subsequent rounds of selection in which the stringency of the elution conditions is increased or modified to identify sequences with the desired binding affinity and/or specificity. Jarosch et al., *Nucleic Acids Res.* 34:86, 2006 have described methods that allow the process to be performed without the constant primer regions.

In various embodiments, the selection process may involve steps in which the stringency of the elution conditions are gradually increased in order to select aptamers with high affinity for the target molecule.

In various embodiments, the selection process may involve steps in which the elution conditions are modified (e.g., by using a different affinity column) in order to select aptamers with desired specificity for the target molecule.

In various embodiments the selection process may generate a collection of sublibraries (or "pools") each of which comprises aptamers with similar affinities and/or specificities for the target molecule. In various embodiments the selection process may generate a single aptamer sequence (or "monoclonal"). In various embodiments the aptamers are DNA based. In various embodiments the aptamers are RNA based. In various embodiments the aptamers are mixed RNA/DNA aptamers.

Multivalent aptamers can be generated by covalently or non-covalently linking two or more of these monovalent aptamers into a single construct. Typically, two or more aptamers (which may have the same or different sequences) may be bound directly to one another (e.g., via a coupling agent) or indirectly through an independent framework. In various embodiments 2, 3, 4, 5, 6, 7 or 8 aptamers may be combined into a single construct. In various embodiments the 2, 3, 4, 5, 6, 7 or 8 aptamers may have the same sequence. It will be appreciated that either one of these approaches may require the aptamers to be chemically modified (e.g., to include pendant reactive groups) prior to coupling. It will also be appreciated that the aptamers of the present disclosure are not limited to a particular coupling reaction or framework (e.g., they can be prepared using frameworks that include polymeric and/or non-polymeric structures). It will further be appreciated that the frameworks may be linear, branched, hyperbranched and/or a combination of these.

In various embodiments the aptamers are covalently bound to each other or a framework. In such embodiments, the aptamers can be directly bound (i.e., with no intervening chemical groups) or indirectly bound through a spacer (e.g., a coupling agent or covalent chain that provides some physical separation between the aptamers or between the aptamers and framework). It is to be understood that aptamers may be covalently bound to each other or a framework through any number of chemical linkages, including but not limited to amide, ester, ether, isourea, and imine bonds.

In various embodiments, the two or more aptamers are non-covalently bound to each other or to a framework. In certain embodiments, the dissociation constant ($K_d$) of the non-covalent linkage in human serum is less than 1 pmol/L. For example, aptamers may be non-covalently bound to each other or a framework via a non-covalent ligand-receptor pair as is well known in the art (e.g., without limitation a biotin-avidin based pair). In such an embodiment, one member of the ligand receptor-pair is covalently bound to one aptamer while the other member of the pair is covalently bound to the other aptamer or framework. When the aptamers (or aptamers and framework) are combined, the strong non-covalent interaction between the ligand and its receptor causes the aptamers to become non-covalently bound to each other (or the framework). Typical ligand/receptor pairs include protein/co-factor and enzyme/substrate pairs. Besides the commonly used biotin/avidin pair, these include without limitation, biotin/streptavidin, digoxigenin/anti-digoxigenin, FK506/FK506-binding protein (FKBP), rapamycin/FKBP, cyclophilin/cyclosporin and glutathione/glutathione transferase pairs. Other suitable ligand/receptor pairs would be recognized by those skilled in the art, e.g., monoclonal antibodies paired with a epitope tag such as, without limitation, glutathione-S-transferase (GST), c-myc, FLAG® and further those described in Kessler pp. 105-152 of *Advances in Mutagenesis*" Ed. by Kessler, Springer-Verlag, 1990; "*Affinity Chromatography: Methods and Protocols (Methods in Molecular Biology)*" Ed. by Pascal Baillon, Humana Press, 2000; and "*Immobilized Affinity Ligand Techniques*" by Hermanson et al., Academic Press, 1992.

3. Chemical Modification of Cross-Linking Agents

In general, it is to be understood that any of the aforementioned multivalent cross-linking agents may be chemically modified, e.g., in order to mitigate undesirable properties.

i. Non-Specific Modifications

In US 2007/0110811 we described the benefits of pegylating lectins in order to reduce their in vivo mitogenicity. Thus, in certain embodiments, a multivalent cross-linking agent may be covalently modified with one or more compounds. Without limitation this might involve reaction with an activated pegylation (PEG) agent (e.g., without limitation N-hydroxysuccinimide activated PEG, succinimidyl ester of PEG propionic acid, succinimidyl ester of PEG butanoic acid, succinimidyl ester of PEG alpha-methylbutanoate, etc.), another water soluble but non-PEG-containing polymer such as poly(vinyl alcohol), a reagent that can be easily coupled to lysines, e.g., through the use of carbodiimide reagents, a perfluorinated compound, etc. The skilled artisan will readily recognize other suitable compounds, e.g., by referring to the comprehensive review that can be found in *Chemical Reagents for Protein Modification* by Lundblad, CRC Press, 3$^{rd}$ Edition, 2004.

In general, the compound(s) may be attached to a multivalent cross-linking agent (e.g., a mitogenic lectin) via any of a number of attachment methods known to those skilled in the art (e.g., via amine, carboxyl, hydroxyl or sulfhydryl groups). The potential covalent linkages are similarly diverse (e.g., including amide bonds, carbamate bonds, ester bonds, thioether bonds, ether bonds, disulfide bonds, etc.). For example, PEGs are conveniently attached through amino or carboxyl groups. Amino acid residues with free amino groups include lysine residues and N-terminal amino acid residues. Amino acid residues with free carboxyl groups include aspartic acid residues, glutamic acid residues and C-terminal amino acid residues. Sulfhydryl groups found in cysteine residues may also be used as a reactive group for attaching the PEGs (or other compounds). In preferred embodiments PEGs are covalently attached to an amino group, especially the free amino group found in lysine residues.

Numerous methods for directly attaching PEGs to proteins are described in Delgado et al., *Crit. Rev. Thera. Drug Carrier Sys.* 9:249-304, 1992; Francis et al., *Intern. J. of Hematol.* 68:1-18, 1998; U.S. Pat. No. 4,002,531; U.S. Pat. No. 5,349, 052; WO 95/06058; and WO 98/32466. One such method uses tresylated monomethoxy poly(ethylene glycol) (MPEG), which is produced by reacting MPEG with tresyl-chloride ($ClSO_2CH_2CF_3$). Tresylated MPEG reacts with exposed amine groups on lectins. A skilled person will recognize that the invention is not limited to any specific pegylation agent (or compound) and will be able to identify other suitable compounds that are known in the art.

In certain embodiments PEGs (or other compounds) may be attached to a multivalent cross-linking agent via an intervening linker. For example, U.S. Pat. No. 5,612,460, discloses urethane linkers for connecting PEG to proteins. PEGs can be attached to a protein via a linker by reaction with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional PEG derivatives and reaction chemistries for attaching PEG to proteins are described in WO 98/32466 and other patents, e.g., those that are assigned to Shearwater of Huntsville, Ala.; Nektar Therapeutics of San Carlos, Calif.; and/or Enzon Pharmaceuticals of Bridgewater, N.J. Catalogs can be obtained from these commercial PEG suppliers that describe a range of suitable PEG compounds and chemistries (e.g., see the Nektar Advanced PEGylation CATALOG 2004).

In various embodiments, N-terminal alpha-amine and/or epsilon-amino lysine groups of polypeptide based cross-linking agents may be succinylated and/or acetylated to change the charge distribution as well as any tertiary and quaternary effects associated with such changes. For example, polypeptides may be succinylated by reaction in a saturated sodium acetate buffer with an excess of succinic anhydride. Acetylation may be performed using the same procedure but with acetic anhydride as the modifying agent. For example, when the protein is concanavalin A, both acetylation and succinylation not only increase the density of negative charge within the polypeptide but also forces it to assemble as dimers instead of tetramers at physiological pH (e.g., see Agrawal et al., *Biochemistry.* 7:4211-4218, 1968 and Gunther et al., *Proc. Natl. Acad. Sci.* (*USA*) 70:1012-1016, 1973). In addition, the in vivo safety profile of these resulting materials is greatly improved as a result.

ii. Binding-Site Modifications

In certain embodiments, it may be advantageous to use an alternative and more specific method for modifying the multivalent cross-linking agents. In particular, we have found that certain low molecular weight conjugates of the present disclosure do not form insoluble drug delivery systems when combined with highly pegylated lectins made using high molecular weight PEG reagents (>5 kDa). This poses a challenge since we have previously found that lower molecular weight PEGs (<5 kDa) are much less effective in reducing lectin mitogenicity. Without wishing to be limited to any particular theory, it may be that the larger PEG groups are capable of sterically preventing binding and network formation with smaller low-valency conjugates, but not larger high-valency conjugates. In view of this, we devised an alternative non-PEG based solution for improving the safety profile of lectin-based cross-linking agents. We achieved this by specifically targeting and modifying the sugar binding site of lectins. For example, by reacting a mannose ligand directly into the concanavalin A binding site and purifying the unreacted material by high affinity ligand chromatography, we have been able to synthesize cross-linking agents with safety profiles that rival those of the best pegylated lectins. Without wishing to be limited to any particular theory, the functional concept appears to be that cell surfaces have a defined sugar affinity, valency, and ligand density, whereas the conjugates can have all of these properties adjusted by design. Thus, while incorporation of mannose into the lectin binding site completely abolishes the cross-linking agents ability to bind and thereby agglutinate or stimulate cells, incorporation of a higher density of higher affinity ligands on the conjugates still allows gel formation. In certain embodiments, incorporation of a small degree of pegylation with low MW, discrete PEG chains may be used to stabilize the multivalent lectins in solution under a variety of extreme storage conditions, yielding manufacturable, safe, functional cross-linking agents which complement the newly engineered conjugates.

In general, binding-site modified lectins will include at least one covalently linked affinity ligand which is capable of associating with one of the lectin binding sites. In various embodiments, the modified lectins may include just one covalently linked affinity ligand. In various embodiments, the lectins may include one covalently linked affinity ligand per binding site. Typically a multivalent lectin will include 2 or 4 binding sites (e.g., a dimer or tetramer of a monovalent lectin) but the present disclosure also encompasses lectins with 3, 5 or more binding sites. The present disclosure also encompasses lectins with more than one covalently linked affinity ligand per binding site. The present disclosure further encompasses materials which include a mixture of lectins that include different numbers of covalently linked affinity ligands and/or that include unmodified lectins.

Any affinity ligand can be used for this purpose as long as it can associate with a binding site of the lectin once covalently linked to the lectin. Typically an affinity ligand will include a recognition element which interacts with the lectin binding site and a reactive linker which enables the affinity ligand to become covalently attached to the lectin once the recognition element is bound within the binding site.

Recognition Element

Any recognition element that can compete for binding with the lectin's cognate ligand (e.g., glucose or mannose in the case of Con A) could be used in an affinity ligand of the present disclosure. In various embodiments, the recognition element includes a saccharide. In certain embodiments the saccharide is a natural saccharide (e.g., glucose, fructose, galactose, mannose, arabinose, ribose, xylose, etc.). In certain embodiments the saccharide is a modified saccharide (e.g., 2'-fluororibose, 2'-deoxyribose, hexose, etc.). In certain embodiments the recognition element is glucose, sucrose, maltose, mannose, derivatives of these (e.g., glucosamine, mannosamine, methylglucose, methylmannose, ethylglucose, ethylmannose, etc.) and/or higher order combinations of these (e.g., a bimannose, a linear and/or branched trimannose, etc.).

Other exemplary saccharides will be recognized by those skilled in the art. In particular, it is to be understood that depending on the application any one of the saccharides that are described above in the context of the conjugate affinity ligands may be used (e.g., any one of the saccharides of formula IVa or IVb). In certain embodiments, the recognition element includes a monosaccharide. In certain embodiments, the recognition element includes a disaccharide. In certain embodiments, the recognition element includes a trisaccharide. In some embodiments, the recognition element includes a saccharide and one or more amine groups. In some embodiments, the recognition element is aminoethylglucose (AEG). In some embodiments, the recognition element is aminoethylmannose (AEM). In some embodiments, the recognition element is aminoethylbimannose (AEBM). In some embodiments, the recognition element is aminoethyltrimannose (AETM). In some embodiments, the recognition element is β-aminoethyl-N-acetylglucosamine (AEGA). In some embodiments, the recognition element is aminoethylfucose (AEF). In other embodiments, the recognition element is D-glucosamine (GA).

In various embodiments, the recognition element includes a polysaccharide, glycopeptide or glycolipid. In certain embodiments, the recognition element includes from 2-10 saccharide moieties, e.g., 2, 3, 4, 5, 6, 7, 8, 9 or 10 moieties. The terminal and/or internal residues of the polysaccharide, glycopeptide or glycolipid may be selected based on the saccharide specificity of the lectin in question (e.g., see Goldstein et al., *Biochem. Biophys. Acta* 317:500-504, 1973 and L is et al., *Ann. Rev. Biochem.* 55:35-67, 1986).

In various embodiments, the recognition element for a particular lectin/glucose combination may be selected empirically. According to such embodiments one or more recognition elements are screened based on their relative binding affinities for the lectin as compared to the target molecule glucose. In certain embodiments a library of saccharides and/or polysaccharides are screened in this manner. A suitable recognition element will exhibit a detectable level of competition with glucose but will not compete so strongly that it prevents all binding between the lectin and glucose. In certain embodiments, different recognition elements may be screened by testing the effect of different affinity ligands on relevant lectin properties (e.g., based on their ability to inhibit agglutination and/or their material set points as discussed in more detail below). In certain embodiments, the recognition element will be selected in view of the conjugate that the modified lectin is to be combined with (e.g., so that the conjugate is able to displace the recognition element from the binding site and thereby form a cross-linked material).

Reactive Linker

Affinity ligands may be covalently linked to a lectin in any manner. Most methods will involve allowing the recognition element of the ligand to associate with the lectin binding site and then causing the reactive linker to react with the lectin. In certain embodiments, the reactive linker may be attached to the recognition element at a position that does not substantially interfere with the binding properties of the recognition element. For example, when the recognition element is a saccharide or polysaccharide the linker may be attached to the C1, C2 or C6 position of a terminal saccharide. In certain embodiments, the linker may be attached to the C1 position. The C1 position is also referred to as the anomeric carbon and may be connected to the linker in the alpha or beta conformation. In certain embodiments, the linker is attached to the C1 position as the alpha anomer.

In certain embodiments, photoactivatable linkers may be used. For example, Beppu et al., *J. Biochem.* 78:1013-1019, 1975, described a method in which an arylazido linker was activated using ultraviolet light to form a covalent bond between concanavalin A and a sugar derivative within the binding site. Similar results were recorded by Fraser et al., *Proc. Natl. Acad. Sci. (USA)* 73:790-794, 1976 using succinylated concanavalin A. A similar procedure has also been employed using ricin and a photoactivatable derivative of galactose as described by Houston, *J. Biol. Chem.* 258:7208-7212, 1983. Photoactivatable derivatives of complex glycopeptide ligands having a higher affinity for lectins than saccharides and disaccharides have also been described by Baenziger et al., *J. Biol. Chem.* 257:4421-4425, 1982. These derivatives were made by covalently linking a photoactivatable group to the peptide portion of the glycopeptide ligand.

In general, any photoactivatable linker may be used such as an aryl, purine, pyrimidine, or alkyl azide, a diazo or diazirine group, a benzophenone, or a nitrobenzene. A more comprehensive list of potentially useful photoactivatable linkers may be found in Fleming, *Tetrahedron* 51:12479-12520, 1995 as well as Brunner, *Annu. Rev. Biochem.* 62:483-514, 1993 and Wong, S. S. *Chemistry of Protein Conjugation and Cross-Linking*, (1993), CRC Press, New York, pp. 168-194.

In various embodiments, the photoactivatable linker may include a diazirine group. Photoactivation of diazirine groups with ultraviolet (UV) light creates reactive carbene intermediates that can form covalent bonds through addition reactions with any amino acid side chain or peptide backbone within range of the linker. Long wavelength UV-light (about 320-370 nm, preferably about 345 nm) is typically used to activate diazirines (e.g., see Suchanek et al., *Nat. Methods* 2:261-268, 2005).

In various embodiments, the photoactivatable linker may include an aryl azide group. When aryl azide groups are exposed to UV-light they form nitrene groups that can initiate addition reactions with double bonds, insertion into C—H and N—H sites, or subsequent ring expansion to react as a nucleophile with primary amines. The latter reaction path predominates when primary amines are present in the sample. Without limitation, long wavelength UV-light (about 320-370 nm, preferably about 366 nm) is thought to be most efficient for substituted aryl azides (e.g., with hydroxy or nitro groups) while shorter wavelengths are thought to be most efficient for unsubstituted aryl azides. Suitable UV-light sources are available commercially, e.g., from Pierce, Rockford, Ill.

For example, in various embodiments the affinity ligand may be of the general formula (V): $R_e$-L where $R_e$ is a recognition element and L is a reactive linker. In certain embodiments $R_e$ is a saccharide moiety. In certain embodiments $R_e$ is a glucose or mannose moiety which is covalently bonded to the linker at the C1 position.

In certain embodiments -L may be of the general formula (VIa):

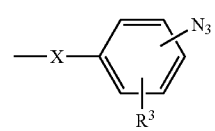

where:
$R^3$ is independently selected from the group consisting of hydrogen, —OH, —$NO_2$, and halogen (e.g., F or Cl);
X is a covalent bond or a bivalent, straight or branched, saturated or unsaturated, optionally substituted $C_{1-20}$ hydrocarbon chain wherein one or more methylene units of X are optionally and independently replaced by —O—, —S—, —N(R')—, —C(O)—, —C(O)O—, —OC(O)—, —N(R')C(O)—, —C(O)N(R')—, —S(O)—, —S(O)$_2$—, —N(R')SO$_2$—, —SO$_2$N(R')—, a heterocyclic group, an aryl group, or a heteroaryl group; and
each occurrence of R' is independently hydrogen, a suitable protecting group, or an acyl moiety, arylalkyl moiety, aliphatic moiety, aryl moiety, heteroaryl moiety, or heteroaliphatic moiety.

In any case where a chemical variable is shown attached to a bond that crosses a bond of ring (for example as shown for R³ above), this means that one or more such variables are optionally attached to the ring having the crossed bond. Each R³ group on such a ring can be attached at any suitable position, this is generally understood to mean that the group is attached in place of a hydrogen atom on the parent ring. This includes the possibility that two R³ groups can be attached to the same ring atom. Furthermore, when more than one R³ group is present on a ring, each may be the same or different than other R³ groups attached thereto, and each group is defined independently of other groups that may be attached elsewhere on the same molecule, even though they may be represented by the same identifier.

In certain embodiments, the —N₃ group is in the meta position. In certain embodiments, the —N₃ group is in the ortho position. In certain embodiments, the —N₃ group is in the para position.

In certain embodiments, one, two, three, four, or five methylene units of X are optionally and independently replaced. In certain embodiments, X is constructed from a $C_{1-10}$, $C_{1-8}$, $C_{1-6}$, $C_{1-4}$, $C_{2-12}$, $C_{4-12}$, $C_{6-12}$, $C_{8-12}$, or $C_{10-12}$ hydrocarbon chain wherein one or more methylene units of X are optionally and independently replaced by —O—, —S—, —N(R')—, —C(O)—, —C(O)O—, —OC(O)—, —N(R')C(O)—, —C(O)N(R')—, —S(O)—, —S(O)₂—, —N(R')SO₂—, —SO₂N(R')—, a heterocyclic group, an aryl group, or a heteroaryl group. In some embodiments, one or more methylene units of X is replaced by a heterocyclic group. In some embodiments, one or more methylene units of X is replaced by a triazole moiety. In certain embodiments, one or more methylene units of X is replaced by —C(O)—. In certain embodiments, one or more methylene units of X is replaced by —C(O)N(R')—. In certain embodiments, one or more methylene units of X is replaced by —O—.

In some embodiments, X is

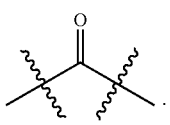 [SMILES: *C(*)=O]

In some embodiments, X is

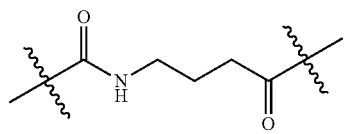

In some embodiments, X is

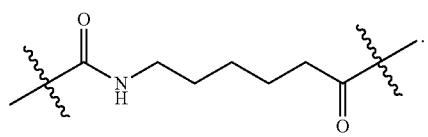 [SMILES: *C(=O)CCCCCNC(*)=O]

In some embodiments, X is

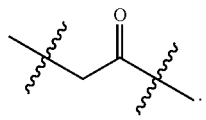 [SMILES: *CC(*)=O]

In some embodiments, X is

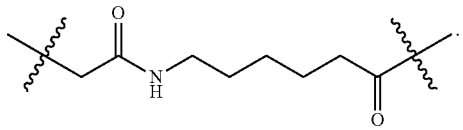 [SMILES: *CC(=O)NCCCCCC(*)=O]

In some embodiments, X is

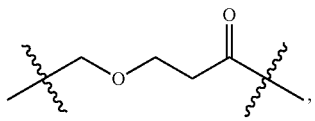 [SMILES: *COCCC(*)=O]

In certain embodiments -L may be of the general formula (VIb):

where X is as defined above for formula (VIa); and R⁴ is hydrogen, $C_1$-$C_6$ alkyl or —CF₃.

In certain embodiments, non-photoactivatable linkers may be used. For example, U.S. Pat. Nos. 5,239,062 and 5,395,924 describe linkers that can be activated by changes in pH or temperature. Exemplary reactive linkers which are discussed include those which can be introduced into an affinity ligand using reagents such as cyanuric chloride (Kay et al., *Nature* 216:514-515, 1967) or dichloro-S-triazines such as 2-amino-4,6-dichloro-S-triazine (Kay et al., *Biochim. Biophys. Acta* 198:276-285, 1970) and 2,4-dichloro-6-methoxy-S-triazine (Lang et al., *J. Chem. Soc. Perkin* 1:2189-2194, 1977). Reactive linkers with NHS-esters or aldehydes that would react primarily with terminal amines such as those found on lysines could also be used.

In various embodiments, the reactive linker for a particular lectin/target molecule combination may be selected empirically. According to such embodiments several affinity ligands with the same recognition element and different linkers (e.g., linkers of different lengths, linkers with different reactive groups, linkers with different hydrophobicity, etc.) are screened based on their effect on relevant lectin properties (e.g., based on their ability to inhibit agglutination and/or their material set points as discussed in more detail below).

ii. Extent of Modification

In general, the number of compounds that are attached to each multivalent cross-linking agent (i.e., the degree of substitution) will vary based on the nature of the cross-linking agent, the nature of the compound(s), the number of reaction sites available and the reaction conditions. For example, the subunits of concanavalin A each include twelve lysine residues. As a result, if concanavalin A is pegylated with a compound that reacts with lysine residues, then each subunit could be covalently linked to 1, 2, 3, 4, 5, 6, 7, 8, 9, 10, 11 or 12 of these compounds. Conversely, each subunit of concanavalin A includes just one glucose binding site. Thus, if concanavalin A is reacted with a compound that reacts at the binding site, then each subunit will be covalenly linked to just one such compound. Methods for determining the degree of substitution are discussed in Delgado et al., *Crit. Rev. Thera. Drug Carrier Sys.* 9:249-304, 1992.

In preferred embodiments, the chemical modification of a multivalent cross-linking agent may be optimized using a plurality of compounds and a plurality of reaction conditions (e.g., that vary the reagent concentrations, pH, temperature, etc.). Preferred compounds and reaction conditions are such that desirable properties (e.g., binding affinity) are not substantially impaired while undesirable properties (e.g., mitogenicity) are reduced as compared to an unmodified cross-linking agent. For example, an automated robotic handling device may be used to prepare a range of modified compositions with different compounds and different reaction conditions. Using routine orthogonal experimentation a skilled person can then screen the properties of the treated compositions. In certain embodiments further rounds of orthogonal optimization are performed around the preferred conditions to further refine the preferred compounds and reaction conditions.

In one embodiment, optimal reaction conditions are identified by separating treated compositions by electrophoresis, preferably by denaturing SDS-PAGE electrophoresis. In various embodiments, compositions which include uniformly modified cross-linking agents are preferred. These preferred compositions will have weaker bands at the molecular weight of the unmodified cross-linking agent as measured by SDS-PAGE.

4. Purification of Cross-Linking Agents

In various embodiments, multivalent cross-linking agents (whether they have been chemically modified or not) can be further processed in order to improve their properties. Thus, in certain embodiments, compositions comprising multivalent cross-linking agents can be purified in order to remove protein fragments, unmodified components, etc. In general, these separations can be achieved on the basis of physical properties (e.g., electrical charge; molecular weight; and/or size) and/or chemical properties (e.g., binding affinity for a target molecule). In certain embodiments optimal removal may be achieved by combining two or more methods that rely on these differential properties. In one embodiment, these separations are performed under denaturing conditions. For example, unmodified or partially modified cross-linking agents can be removed on the basis of their net charge by ion-exchange chromatography. Gel-filtration chromatography may be used to discriminate between differentially modified cross-linking agents on the basis of size. Affinity chromatography is another method that may be used to remove unmodified or partially modified cross-linking agents. This approach takes advantage of the differential binding affinity of modified, partially modified and unmodified cross-linking agents for a specific target molecule.

5. Characterization of Cross-Linking Agents

In various embodiments, multivalent cross-linking agents (whether they have been chemically modified or not) can be screened or further tested in order to confirm or characterize their properties. Representative assays include: affinity assays, agglutination assays, T-cell mitogenicity assays, T-cell viability assays, antigenicity assays, etc.

Affinity assays may involve passing the multivalent cross-linking agent over an affinity column (e.g., a resin with the target molecule) and determining the elution conditions required to remove the cross-linking agent from the column. Equilibrium dialysis can also be used as is known in the art. Set point assays in which the cross-linking agent is combined with one or more conjugates of the present disclosure and then contacted with varying concentrations of the target molecule may also be used. Preferably the binding affinity of a chemically modified cross-linking agents is at least 75% that of the unmodified cross-linking agent. More preferably the binding affinity is at least 85% and yet more preferably at least 95% that of the unmodified cross-linking agent.

In certain embodiments, an agglutination assay may be used to determine the minimum agglutinating concentration (MAC) of a multivalent cross-linking agent. For example, in certain embodiments the MAC may be determined using rabbit erythrocytes as described in US 2007/0110811. We have found that higher MAC values correlate strongly with reduced mitogenicity in the case of chemically modified lectins. In certain embodiments a modified cross-linking agent may have a MAC that is higher than the unmodified cross-linking agent. Preferably the MAC is 25 times that of the unmodified cross-linking agent. More preferably the MAC is 50 times and yet more preferably more than 100 times that of the unmodified cross-linking agent. In certain embodiments, the modified cross-linking agent exhibits a MAC with a 2% v/v suspension of formaldehyde-stabilized rabbit erythrocytes that is greater than 4 ug/ml. Preferably the MAC is greater than 6 ug/ml, more preferably greater than 10 ug/ml, even more preferably greater than 25 ug/ml.

Mitogenicity assays will typically involve contacting the compositions of interest with a T-cell culture (e.g., PBMC cells) for a period of time and then measuring the level of T-cell proliferation. Various methods for measuring cell proliferation are known. In one embodiment the cell density may be measured spectrophotometrically at 450 nm. In another embodiment an indirect measure can obtained by detecting the reduction of MTT at 570 nm (e.g., see Ohno et al., *J. Immunol. Methods* 145:199-203, 1991). In preferred embodiments, the level of cell proliferation is determined using a tritiated thymidine uptake assay. Those skilled in the art will recognize that other suitable methods may be used and that the invention is in no way limited to a specific proliferation assay. In certain embodiments, the T-cell mitogenicity of a modified cross-linking agent is less than 50% the T-cell mitogenicity of the unmodified cross-linking agent. The reduction in T-cell mitogenicity may be assessed by performing a comparative thymidine uptake assay across a range cross-linking agent concentrations, e.g., 0.01, 0.1, 1, 10, 100 and 1000 ug/ml. In preferred embodiments, the thymidine uptake assay is performed with samples that include approximately 500,000 PBMCs. The mitogenicity of the test composition (e.g., a modified composition) is then expressed as the % maximal unmodified mitogenicity. The % maximal unmodified mitogenicity is obtained by dividing the maximal CPM (counts per minute) value for the test composition over all measured concentrations by the maximal CPM value of the unmodified composition over all measured concentrations. Preferably, the test composition with reduced mitogenicity induces a level of T-cell proliferation that is at least 50% lower than the unmodified composition. More preferably, the level is at least 75% lower, even more preferably at least 90%, 95% or 99% lower.

T-cell viability can be measured using a similar experiment by adding Trypan Blue to the T-cell culture and counting a representative sample of the cells (noting those that either take up the trypan or still exclude the trypan, i.e., those that become blue vs. those that do not). The % viability is then calculated by dividing the number of cells that exclude the trypan (alive, "not blue") by the total number of cells counted (dead, "blue," plus live, "not blue"). Those skilled in the art will recognize that other suitable methods may be used and that the invention is in no way limited to a specific viability assay. In certain embodiments, a modified cross-linking agent exhibits a percentage cell viability at 100 ug/ml that is greater than 10% when assayed using PBMCs at a concentration of 500,000 cells/ml. Preferably the percentage cell viability is greater than 25%, more preferably greater than 50%, even more preferably greater than 90%.

Cross-Linked Materials

When conjugates and cross-linking agents are combined in the absence of the target molecule, a non-covalently cross-linked material is formed. In various embodiments, the material may be prepared in aqueous solution through self-assembly by mixing solutions of the cross-linking agent and conjugate. In various embodiments, particles of the material may be prepared by reverse emulsion. As described in more detail in US 2004/0202719, this can be achieved by adding the aforementioned aqueous solution to a mixture of a hydrophobic liquid and a surfactant and agitating the mixture.

Once formed, the cross-linked material can be used for a variety of applications. When the material is placed in the presence of free target molecules these compete for the interactions between the cross-linking agents and the conjugates. Above a certain concentration of free target molecule, the level of competition becomes such that the material begins to degrade by releasing conjugates from the surface. In various embodiments, the extent and/or rate of release increases as the concentration of target molecule increases. As a result, conjugates are released from the material in a manner which is directly tied to the local concentration of the target molecule.

In general, the release properties of the material will depend on the nature of the cross-linking agents, conjugates, target molecule and conditions (e.g., pH, temperature, etc.). If the affinity of the cross-linking agents for the conjugates is much greater than for the target molecule then the material will only release conjugates at high concentrations of target molecule. As the relative affinity of the cross-linking agents for the conjugates is decreased, release of conjugates from the material will occur at lower target molecule concentrations. The release properties of the material can also be adjusted by varying the relative amounts of cross-linking agent to conjugate. Higher ratios of cross-linking agent to conjugate will lead to materials that release conjugates at higher target molecule concentrations. Lower ratios of cross-linking agent to conjugate will lead to materials that release conjugates at lower target molecule concentrations. It will be appreciated that, depending on the application, these variables will enable one to produce materials which respond to a wide variety of target molecule concentrations.

In various embodiments, the cross-linked material is insoluble when placed in pH 7 HEPES buffered saline at 37 C (25 mM HEPES containing 150 mM NaCl and no target molecule). In various embodiments, the cross-linked material remains substantially insoluble when target molecule is added to the buffer up to a threshold concentration called the set point. Above the set point, the cross-linked material exhibits an increase in the extent and rate of release of conjugates. It will be appreciated that this transition may occur sharply or may occur gradually over a range of concentrations around the set point. In general, the desired set point and transition will depend on the nature of the target molecule and the intended application for the material. In particular, when the material is designed to respond to an increase in the level of a particular target molecule, the desired set point may be determined based on the normal physiological range of concentrations of the target molecule. It is to be understood that the amount of target molecule present in a patient may fluctuate based on internal and/or external factors. For example, in certain embodiments, the amount of target molecule may fluctuate naturally over time, e.g., in response to changes in hormonal cycles or metabolic pathways (lactate increasing during an endurance event, etc.). In certain embodiments, the fluctuations may result from an external event, e.g., an increase in glucose following a meal. In various embodiments, external factors may be used to artificially trigger the release of conjugates from a material of the present disclosure. For example, if release of conjugate is sensitive to an increase in glucose one could artificially release conjugates for a short period of time by ingesting a high-glucose drink.

In various embodiments, the target molecule is glucose. The normal physiological range of glucose concentrations in humans is 60 to 200 mg/dL. Glucose concentrations below 60 mg/dL are considered hypoglycemic. Glucose concentrations above 200 mg/dL are considered hyperglycemic. In various embodiments, a material of the present disclosure may remain substantially insoluble when placed in pH 7 HEPES buffered saline containing 20, 30, 40, 50, 60, 70, 80, 90, or 100 mg/dL glucose at 37 C for six hours using USP dissolution test method II at 50 rpm. In various embodiments, less than 1, 2, 4, 6, 8, or 10% of the material dissolves when placed in pH 7 HEPES buffered saline with 20, 30, 40, 50, 60, 70, 80, 90, or 100 mg/dL glucose at 37 C for six hours using USP dissolution test method II at 50 rpm. In various embodiments, at least 10, 20, 30, 40, 50, 60, 70, 80, 90 or 100% of a material of the present disclosure dissolves when it is placed in pH 7 HEPES buffered saline with 100, 150, 200, 250, 300, 350 or 400 mg/dL glucose at 37 C for six hours using USP dissolution test method II at 50 rpm.

The following tables provide normal physiological ranges for other exemplary target molecules:

|  | Low | High | Unit |
|---|---|---|---|
| Metabolites |  |  |  |
| Urea | 7 | 18 | mg/dL |
| Creatinine - male | 0.7 | 1.3 | mg/dL |
| Creatinine - female | 0.6 | 1.1 | mg/dL |
| Hormones |  |  |  |
| Thyroid stimulating hormone (TSH) | 0.4 | 4.7 | mIU/L |
| Free thyroxine (FT4) | 9 | 24 | pmol/L |
| Free triiodothyronine (FT3) | 2.5 | 5.3 | pmol/L |
| Adrenocorticotropic hormone (ACTH) | 1.3 | 15 | pmol/L |
| Cortisol (morning) | 250 | 850 | nmol/L |
| Cortisol (afternoon) | 110 | 390 | nmol/L |
| Prolactin (male) | n/a | 450 | mIU/L |
| Prolactin (female) | n/a | 580 | mIU/L |
| Testosterone (male post-puberty) | 8 | 38 | nmol/L |
| Testosterone (male pre-puberty) | 0.1 | 0.5 | nmol/L |
| Testosterone (female) | 0.3 | 2.5 | nmol/L |

It will be appreciated that the desired set point for these and other target molecules can be readily determined for a variety of different applications. It will also be appreciated that the set point may need to be adjusted for certain patients (e.g., based on patient gender, patients with abnormally low or high levels of a target molecule, etc.) or applications (e.g., a drug delivery system designed to release on a more frequent basis may require a lower threshold concentration than a system designed to release less frequently).

It will be appreciated that a material having a desired set point may be generated via routine experimentation using the materials and methods described herein. For example, the same cross-linking agent and conjugate can be combined to produce a series of materials with a gradually increasing ratio of cross-linking agent to conjugate (w/w). These materials will cover a spectrum of set points. Once a lead material with a suitable set point has been identified the process can be repeated with a finer resolution to yield an optimized material. Alternatively (or additionally) the same conjugate can be combined with a plurality of different cross-linking agents that have gradually increasing affinities for the conjugate. This will yield a plurality of materials with a spectrum of set points that can be further refined (e.g., by varying the w/w ratio of cross-linking agent to conjugate). Alternatively one could initiate the process by combining the same cross-linking agent with a plurality of different conjugates. In various embodiments, the conjugates may have varying affinities for the cross-linking agent (e.g., as a result of including different affinity ligands). In various embodiments, the conjugates may include the same affinity ligands but have different molecular weights (e.g., as a result of different conjugate frameworks).

Uses

In another aspect, the present disclosure provides methods of using the materials. In general, the materials can be used to controllably release conjugates in response to a target molecule. As discussed below, the material can be brought into contact with the target molecule in vitro or in vivo.

In various embodiments, a material may be used as a component of an in vitro or in vivo chemical sensor. This aspect is described below in the context of glucose sensors; however, it will be appreciated from the foregoing that other chemical sensors may be prepared by simply using a different target molecule.

For example, in various embodiments, a material of the present disclosure may be used in glucose sensors that are based on fluorescence resonance energy transfer (FRET). FRET is based on the fact that when two different fluorophores are brought closely together this allows for energy transfer between the two fluorophores, resulting in a decrease in the fluorescence of one or both of the fluorophores, which is called fluorescence quenching (Ballerstadt et al., *Anal. Chim. Acta* 345:203-212, 1997). In the absence of glucose, a mixture of a fluorescently labeled cross-linking agent and a fluorescently labeled conjugate will form an insoluble cross-linked material and the neighboring fluorophores will undergo FRET. In the presence of glucose, the average distance between the fluorescently labeled cross-linking agent and the fluorescently labeled conjugate will increase causing the level of FRET to decrease and thereby leading to an increase in the individual fluorescence signals. The level of fluorescence can thereby be directly correlated with the level of glucose.

In other exemplary embodiments, materials of the present disclosure may be used in viscosity-based glucose sensors (e.g., see U.S. Pat. Nos. 6,267,002; 6,477,891; and 6,938,463). Conjugates and cross-linking agents are again combined to form a cross-linked material. Addition of glucose to the material now causes a concentration dependent reduction in viscosity which can be measured (e.g., as a function of shear rate using a microviscometer set up in a cone-and-plate geometry). The viscosity of the sample can thereby be directly correlated with the level of glucose. It will be appreciated that these two exemplary glucose sensors do not require any drug to be present within the conjugates. It will also be appreciated that a viscosity-based sensor does not require a detectable label to be present within the conjugates.

In various embodiments, a material may be used to controllably deliver a drug to a patient. The invention encompasses treating a disease or condition by administering a material of the present disclosure. Although the materials can be used to treat any patient (e.g., dogs, cats, cows, horses, sheep, pigs, mice, etc.), they are most preferably used in the treatment of humans. A material can be administered to a patient by any route. In general the most appropriate route of administration will depend upon a variety of factors including the nature of the disease or condition being treated, the nature of the drug, the nature of the target molecule, the condition of the patient, etc. In general, the present disclosure encompasses administration by oral, intravenous, intramuscular, intra-arterial, subcutaneous, intraventricular, transdermal, rectal, intravaginal, intraperitoneal, topical (as by powders, ointments, or drops), buccal, or as an oral or nasal spray or aerosol. General considerations in the formulation and manufacture of pharmaceutical compositions for these different routes may be found, for example, in *Remington's Pharmaceutical Sciences*, 19$^{th}$ ed., Mack Publishing Co., Easton, Pa., 1995.

In various embodiments, the material may be administered subcutaneously, e.g., by injection. The material can be dissolved in a carrier for ease of delivery. For example, the carrier can be an aqueous solution including, but not limited to, sterile water, saline or buffered saline. In general, a therapeutically effective amount of a drug in the form of a conjugate will be administered. By a "therapeutically effective amount" of a drug is meant a sufficient amount of the drug to treat the disease or condition at a reasonable benefit/risk ratio, which involves a balancing of the efficacy and toxicity of the drug. In general, therapeutic efficacy and toxicity may be determined by standard pharmacological procedures in cell cultures or with experimental animals, e.g., by calculating the $ED_{50}$ (the dose that is therapeutically effective in 50% of the treated subjects) and the $LD_{50}$ (the dose that is lethal to 50% of treated subjects). The $ED_{50}/LD_{50}$ represents the therapeutic index of the drug. Although in general drugs having a large therapeutic index are preferred, as is well known in the art, a smaller therapeutic index may be acceptable in the case of a serious disease or condition, particularly in the absence of alternative therapeutic options. Ultimate selection of an appropriate range of doses for administration to humans is determined in the course of clinical trials.

In various embodiments, the drug is insulin and the average daily dose of insulin is in the range of 10 to 200 U, e.g., 25 to 100 U (where 1 Unit of insulin is ~0.04 mg). In certain embodiments, an amount of material with these insulin doses is administered on a daily basis. In certain embodiments, an amount of material with 5 to 10 times these insulin doses is administered on a weekly basis. In certain embodiments, an amount of material with 10 to 20 times these insulin doses is administered on a bi-weekly basis. In certain embodiments, an amount of material with 20 to 40 times these insulin doses is administered on a monthly basis. Those skilled in the art will be recognize that this same approach may be extrapolated to other approved drugs with known dose ranges, e.g., any of the approved insulin sensitizers and insulin secretagogues described herein.

It will be understood that the total daily usage of a drug for any given patient will be decided by the attending physician within the scope of sound medical judgment. The specific therapeutically effective amount for any particular patient will depend upon a variety of factors including the disease or condition being treated; the activity of the specific drug employed; the specific composition employed; the age, body weight, general health, sex and diet of the patient; the time of administration, route of administration and rate of excretion of the specific drug employed; the duration of the treatment; drugs used in combination or coincidental with the specific drug employed; and like factors well known in the medical arts. In various embodiments, a material of the present disclosure may be administered on more than one occasion. For example, the present disclosure specifically encompasses methods in which a material is administered by subcutaneous injection to a patient on a continuous schedule (e.g., once a day, once every two days, once a week, once every two weeks, once a month, etc.).

In certain embodiments, a material of the present disclosure may be used to treat hyperglycemia in a patient (e.g., a mammalian patient). In certain embodiments, the patient is diabetic. However, the present methods are not limited to treating diabetic patients. For example, in certain embodiments, a material may be used to treat hyperglycemia in a patient with an infection associated with impaired glycemic control. In certain embodiments, a material may be used to treat diabetes.

In various embodiments, a material of the present disclosure may be administered to a patient who is receiving at least one additional therapy. In various embodiments, the at least one additional therapy is intended to treat the same disease or disorder as the administered material. In various embodiments, the at least one additional therapy is intended to treat a side-effect of the primary drug. The two or more therapies may be administered within the same, overlapping or non-overlapping timeframes as long as there is a period when the patient is receiving a benefit from both therapies. The two or more therapies may be administered on the same or different schedules as long as there is a period when the patient is receiving a benefit from both therapies. The two or more therapies may be administered within the same or different formulations as long as there is a period when the patient is receiving a benefit from both therapies. In certain embodiments, a single material of the present disclosure may include more than one drug for treating the same disease or disorder. In certain embodiments, two or more separate materials of the present disclosure may be administered (as a mixture or separately) that include different drugs for treating the same disease or disorder. In certain embodiments, an unconjugated secondary drug may be included in a material of the present disclosure (i.e., a drug which is simply mixed with the components of the material and not covalently bound to the cross-linked material). For example, in certain embodiments, any of these approaches may be used to administer more than one anti-diabetic drug to a subject. Certain exemplary embodiments of this approach are described in more detail below in the context of insulin-related therapies; however, it will be appreciated from the foregoing that other therapies will benefit from such combination approaches.

Insulin sensitizers (e.g., biguanides such as metformin, glitazones) act by increasing a patient's response to a given amount of insulin. A patient receiving an insulin sensitizer will therefore require a lower dose of an insulin-based material of the present disclosure than an otherwise identical patient would. Thus, in certain embodiments, a material comprising insulin conjugates may be administered to a patient who is also being treated with an insulin sensitizer. In various embodiments, the material of the present disclosure may be administered at up to 75% of the normal dose required in the absence of the insulin sensitizer. In various embodiments, up to 50, 40, 30 or 20% of the normal dose may be administered.

Insulin resistance is a disorder in which normal amounts of insulin are inadequate to produce a normal insulin response. For example, insulin-resistant patients may require high doses of insulin in order to overcome their resistance and provide a sufficient glucose-lowering effect. In these cases, insulin doses that would normally induce hypoglycemia in less resistant patients fail to even exert a glucose-lowering effect in highly resistant patients. Similarly, the materials of the present disclosure are only effective for this subclass of patients when they release high levels of insulin-conjugates in a suitable timeframe. In certain embodiments, the treatment of this subclass of patients may be facilitated by combining the two approaches. Thus in certain embodiments, a traditional insulin-based therapy is used to provide a baseline level of insulin and a material of the present invention is administered to provide a controlled supplement of insulin when needed by the patient. Thus, in certain embodiments, a material comprising insulin conjugates may be administered to a patient who is also being treated with insulin. In various embodiments, the insulin may be administered at up to 75% of the normal dose required in the absence of the material of the present disclosure. In various embodiments, up to 50, 40, 30 or 20% of the normal dose may be administered. It will be appreciated that this combination approach may also be used with insulin resistant patients who are receiving an insulin secretagogue (e.g., a sulfonylurea, GLP-1, exendin-4, etc.) and/or an insulin sensitizer (e.g., a biguanide such as metformin, a glitazone).

Kits

A significant manufacturing advantage of the low molecular weight conjugates described herein was only realized after developing and testing cross-linked materials that had been prepared from these conjugates and affinity ligand modified lectins. Due to the low molecular weight of both the conjugates and affinity ligand modified lectins, the materials were found to form into a dispersion of particles rather than a single large volume gel network. This is significant because while cross-linked materials prepared with high molecular weight polymers and pegylated lectins flow easily through a narrow gauge needle once loaded and pressure is applied with the syringe plunger they cannot be pulled into a syringe with a narrow gauge needle. This means that the finished product needs to be pre-loaded into individual syringes, a complicated, costly process that does not readily lend itself to large scale production. The dispersions, on the other hand, can be manufactured in large quantities and loaded under aseptic conditions into conventional multi-use drug vials. In addition, given the large increase in drug mass loading per conjugate and the ratio at which the conjugate and affinity ligand modified lectins form optimal networks, the effective drug loading is about an order of magnitude higher in these materials versus materials prepared with high molecular weight conjugates. For example, the high mass loadings of insulin allow us to prepare dispersions containing up to 100 U/ml of insulin equivalents, the standard concentration used in all commercial insulin formulations. The dispersions are easily resuspended by gentle rolling just like other insulin products. Also like those commercial formulations, the new dispersions may be easily pulled up through a 28G needle to the appropriate dose volume and injected just like water without any significant pressure required. Incorporation of m-cresol as the bacteriostatic agent (used in all currently marketed insulin products) does not change the performance or safety profile and allows multiple daily usage for prolonged periods without any detectable microbial contamination. In various embodiments, the present disclosure therefore provides kits which include one or more vials with dispersion of cross-linked material.

In another aspect, the present disclosure provides libraries of conjugates and/or cross-linking agents. These libraries may be particularly useful for generating materials with a desired set point. In various embodiments, a library may include a plurality of conjugates which produce different set points with the same cross-linking agent. In various embodiments, a library may further include one or more cross-linking agents which form cross-linked materials with conjugates in the library. When the library includes more than one such conjugates, the different conjugates may have different molecular weights, a different number of affinity ligands per conjugate molecule and/or different affinity ligands. In various embodiments, a library may include one or more of the conjugates that include more than one type of affinity ligand.

EXAMPLES

I. Methods of Making Exemplary Conjugates

This first set of examples describes various methods for making exemplary conjugates. It is to be understood that these methods can be modified to produce other conjugates that fall within the scope of the invention.

Example 1

Synthesis Via Atom-Transfer Radical Polymerization

Figure 2:
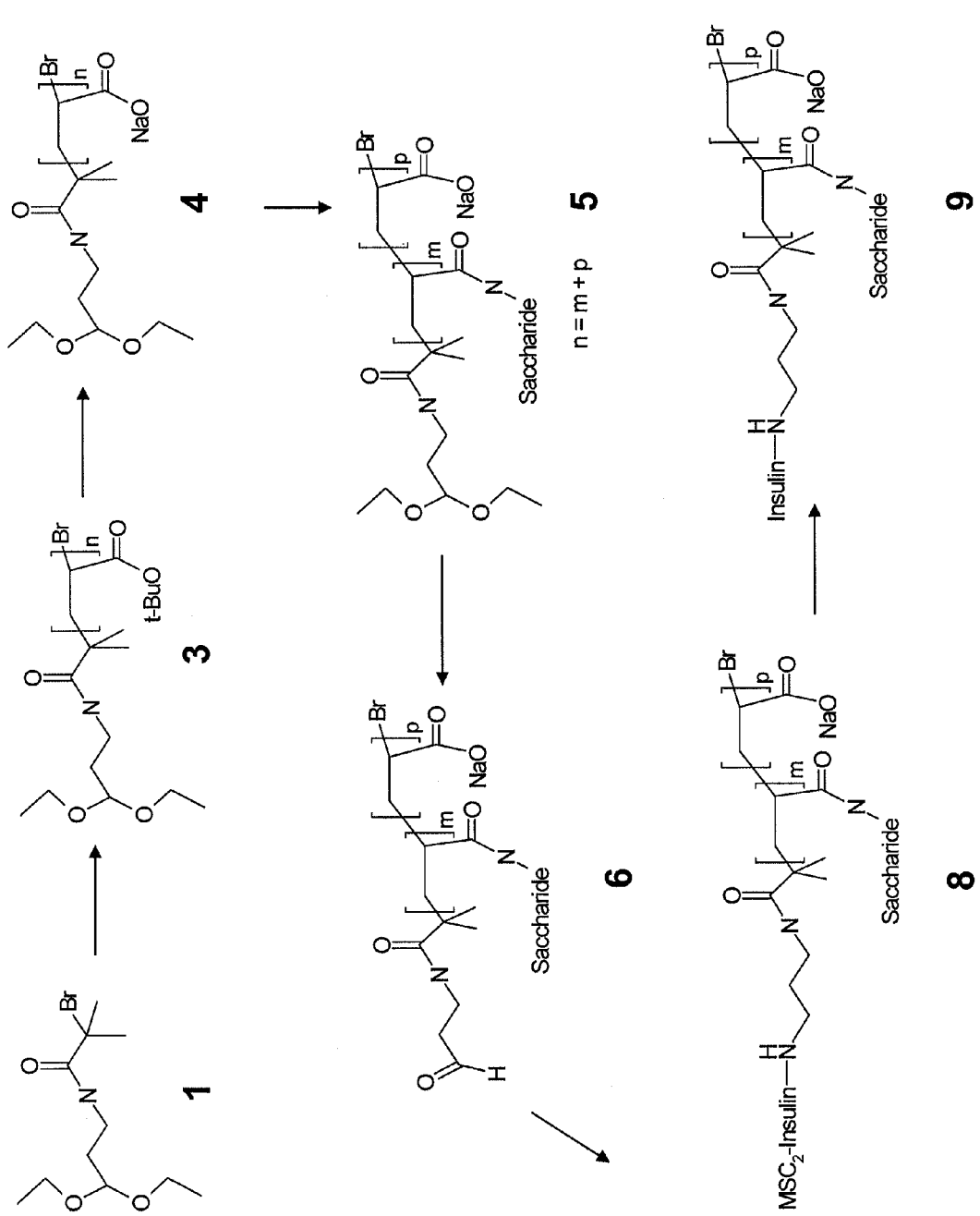
FIG. 2: is a schematic which shows an exemplary Atom Transfer Radical Polymerization (ATRP) process as described in Example 1.

FIG. 2 depicts a scheme for preparing conjugates via atom-transfer radical polymerization (ATRP), also known as "living" free radical polymerization. As a living radical polymerization, it allows the reaction to be carried out in a controlled way, and can be used to obtain polymers with low polydispersity.

In this case the polymerization initiator was synthesized separately and contained the acetal moiety. The initiator was used create polymer chains, each bearing a terminal acetal functionality.

a. Synthesis of the Initiator (1)

To a dichloromethane solution (30 ml) of 1-amino-3,3'-diethoxypropane (1 ml), 4-dimethylaminopyridine (4 mg), triethylamine (1.1 ml), and bromoisobutyryl bromide (0.824 ml) was added dropwise 0° C. The solution was stirred at that temperature for 15 min and was subsequently allowed to warm up to room temperature. It was then stirred for 4 hours. The reaction mixture was extracted with dichloromethane, and the organic layer was washed with acidified water, saturated aqueous sodium bicarbonate, brine, and water, dried with magnesium sulfate. The solution was filtered and dichloromethane was removed via rotory evaporation to give a pale yellow oil. Proton NMR of the oil showed that the oil was very pure, and could be used for polymerization or, if preferred, purified further by silica chromatography.

b. Synthesis of Ligand for ATRP Polymerization of t-Butyl Acrylate.

5.4 g of 2-pyridine carboxaldehyde was added to 40 ml of diethyl ether, and the reaction mixture was cooled to 0° C. under nitrogen. 5.0 ml of octylamine was added dropwise over 10 minutes to the stirring carboxaldehyde-ether mixture. The reaction mixture was stirred for 4 hours at 0° C., after which time the ice bath was removed and the reaction mixture was allowed to warm to room temperature for an additional two hours. At this time 4.0 g of magnesium sulfate was added and stirred during the final two hours. The mixture was filtered to remove insolubles, and the resulting solution was placed in a rotary evaporator to remove the diethyl ether, giving a dark orange oil. This oil was distilled at 120° C. under vacuum to give a clear yellow oil. This oil was found to be pure by $^1$H NMR. This ligand was used in the subsequent ATRP synthesis.

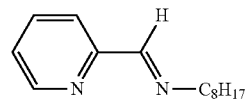

N-(pyridin-2-ylmethylene)octan-1-amine (ATRP ligand)

c. ATRP Polymerization Of t-Butyl Acrylate to Give Acetal Terminally Functionalized Poly(t-Butyl Acrylate) (3)

2.5 ml of inhibitor-free t-butyl acrylate, 1.67 ml of inhibitor-free toluene, and 1.37 mmol of either N,N,N',N'',N''-pentamethyldiethylenetriamine (PMDETA) or ATRP Ligand were added to a 100 ml Schlenk-type flask. These were degassed through three freeze/pump/thaw cycles after which time 198 mg of copper(I) bromide was added and stirred for 30 min at room temperature. Next 331 ul of ATRP initiator (1) was added to the solution, and the solution was stirred for 15 minutes at room temperature. Then the solution was placed into an oil bath at either 40 C, 60 C, or 90 C and heated for either 4 hours or overnight (14 hours) depending on the desired resulting degree of polymerization. The resulting polymer solution was filtered through a column of neutral alumina, and the toluene was removed by rotary evaporation to give a viscous polymer that was used in subsequent steps.

d. Hydrolysis of t-Butyl Acrylate to Provide Polymer (4)

The resulting viscous polymer was dissolved in 15 ml of dichloromethane and 12 ml of trifluoroacetic acid, and the mixture was stirred overnight to hydrolyze the t-butyl groups of the poly(t-butyl acrylate) to give a poly(acrylic acid) polymer. The next day, a gum like substance had precipitated in the flask—the liquid/solid mixture was placed in a rotary evaporator to remove all of the solvents to yield the gummy solid acetal terminally functionalized-poly(acrylic acid). This solid was taken up in 40 ml of deionized water and bring the pH of the solution up to 8.0 by using 50% sodium hydroxide. The polymer was precipitated by adding 4 parts acetone to 1 part polymer solution. The resulting suspension was mixed vigorously and centrifuge at 4500×g for 5 minutes. The first precipitation gave an oil, not a solid, and care was needed for decanting the acetone. The resulting oil was washed twice more with acetone to obtain a gummy solid and mechanical stirring. Remove trace acetone by washing/precipitating the polymer twice with diethyl ether. After the final decantation of diethyl ether, vacuum was used to remove residual solvent from the polymer to obtain a dry powder.

e. Conversion of Terminal Acetal to Aldehyde

During the hydrolysis step, it was found that the acetal spontaneously converted to the aldehyde functionality. This material could be used in the aldehyde form, or if desired, the aldehyde functionality could be converted back into the acetal functionality through methods known to those skilled in the art (e.g., suspending polymer in methanol or ethanol solution with an acid catalyst, heating at 40° C. overnight). Often it was found to be desirable to keep the aldehyde functionality protected as the acetal during subsequent chemical transformations.

f. Modification of Polymer with Saccharide to Provide Polymer (5)

The terminally functionalized acetal-poly(acrylic acid) polymer (4) was functionalized with 1-aminoethyl-($\alpha$-1,3),($\alpha$-1,6)-mannotriose as follows: 202 mg of the acetal-poly (acrylic acid) (sodium form) was added to 10.0 ml deionized water and the pH was adjusted to 6.0. 447 mg of EDAC and 293 mg of N-hydroxysuccinimide (NHS) was added to the solution, which was stirred for 25 minutes at room temperature. To this solution was added a solution of the 1-aminoethyl-($\alpha$-1,3),($\alpha$-1,6)mannotriose (300 mg of saccharide dissolved in 3.0 ml of a pH 6 buffered aqueous solution). The resulting mixture was stirred for 3 hours. The resulting saccharide-modified, acetal-poly(acrylic acid) was purified by size exclusion chromatography and used in subsequent steps.

g. Conversion of Acetal-Poly(Acrylic Acid-Saccharide) to Aldehyde-Poly(Acrylic Acid-Saccharide) (6)

The acetal-poly(acrylic acid) powder is stirred at 50 mg/ml in a pH 1.0 aqueous solution for 12 hours to convert the acetal functionality to the aldehyde functionality. The polymer solution is reneutralized to pH 7.0 and the resulting solution is purified by size exclusion chromatography.

h. Synthesis of MSC2-Insulin

The following synthesis of insulin was carried out in order that only one reactive amine be available to react with the aldehyde moiety of the aldehyde-poly(acrylic acid). Under rapid stirring 76 ml of anhydrous dimethyl sulfoxide and 3.977 mg of insulin was added to a reaction flask such that the concentration of insulin will be 52.33 mg/ml. 3.978 ml of anhydrous triethylamine was immediately added. After waiting for the insulin solution to dissolve completely 1.591 ml of a 1.0M 2-(methanosulfonyl)ethyl succinimidyl carbonate solution in tetrahydrofuran solution was added to the reaction mixture. After 60 minutes of stirring at room temperature, 3.977 ml of a 1:20 dilution of ethanolamine in dimethylsulfoxide was added to quench the reaction. The protein product was recovered by adding the reaction mixture to 1600 ml of acetone, and precipitating the insulin by addition of a hydrochloric acid solution, and filtration to recover the solid precipitate. The precipitate wa washed with acetone and the final powder was subjected to reverse phase chromatography to purify the desired MSC-Gly-A1, MSC-Lys-B29-insulin isomer from the undesirable isomers. The desired product identify was confirmed through liquid chromatography-mass spectroscopy, and Edman sequencing.

i. Reaction of MSC2-Insulin with Aldehyde-Poly(Acrylic Acid-Saccharide) to Provide Polymer (8)

To a reaction flask, 4.0 ml of a 50 mg/ml aldehyde-poly (acrylic acid-saccharide) polymer was added, and the pH was adjusted to 6.5. To this solution was added 1.2 ml of a 10 mg/ml solution of MSC2-insulin in dimethylsulfoxide, followed by 0.67 ml of a sodium cyanoborohydride solution (100 mg/ml) in a pH 6.5 aqueous solution. The reaction mixture was allowed to react at room temperature for 30 min, 1 hour, 12 hours, or longer depending on the desired conversion of the reaction. Removal of non-covalently attached insulin was accomplished through reverse phase chromatography, ion-exchange chromatography, or size exclusion chromatography. The amount of remaining non-covalently attached insulin was assayed either by reverse phase chromatography or by denaturing polyacrylamide gel electrophoresis (SDS-PAGE).

j. Removal of MSC Groups to Provide Polymer (9)

To a 1.0 ml solution of the $MSC_2$-insulin-poly(acrylic acid-saccharide) conjugate at 50 mg/ml in an aqueous buffer, 0.5 ml of methanol and 0.5 ml of dioxane was added. The resulting mixture was cooled to 0 C, after which time 0.15 ml of a 2.0N sodium hydroxide solution was added, and the mixture was stirred for 20 minutes. After this time, the reaction mixture was diluted by 3 volumes of deionized water, and the solution pH was neutralized by adding glacial acetic acid until the solution pH was 7.0.

k. Conjugate In Vivo Bioactivity

The $MSC_2$-insulin-poly(acrylic acid-saccharide) polymer solution (approximately 1-10 mg/ml concentration) was assayed for its solution absorbance to 280 nm light (A280). Normal Sprague-Dawley rats were fasted for at least 1 hour prior to the experiment. The polymer solution was filtered through 0.2 micron filters to make the solution sterile, and the insulin-containing conjugate was dosed subcutaneously into the animals at time zero. Blood glucose values in the animals were measured via the tail vein, and the time points were –15, 0, 15, 30, 60, 90, 120, 150, 180, 240, 300, 360 min post injection. It was observed that the insulin polymer conjugate demonstrated significant glucose depression activity in Sprague-Dawley rats (data not shown).

Example 2

Synthesis Via Free Radical Polymerization

Figure 3:
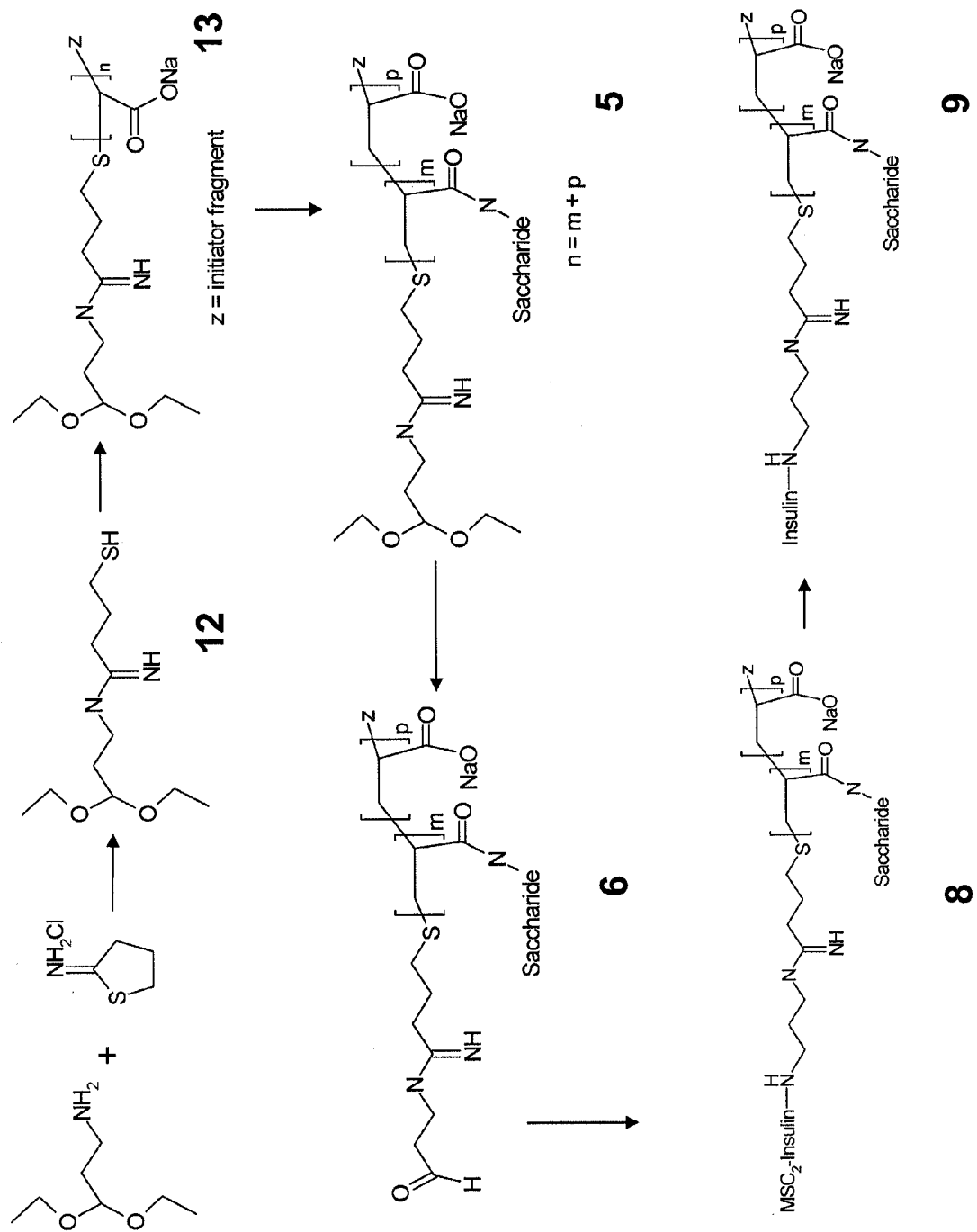
FIG. 3: is a schematic which shows an exemplary Free Radical-Chain Transfer Process as described in Example 2.

FIG. 3 depicts a scheme for preparing polymers via conventional free radical polymerization using an acetal containing chain transfer agent.

a. Synthesis of Chain Transfer Agent and Polymerization of Acrylic Acid

Preheat an oil bath to 60° C. over a stir plate. Begin a nitrogen purge through an oven dried long necked Schlenk flask. Under air free conditions and mild mixing add 170.0 mmols tetrahydrofuran and 17.9 mmols acrylic acid to the Schlenk flask.

b. Preparation of the Chain Termination Agent (12)

Mix 6 mmols of 1-amino-3,3-dietheoxypropane, 4.8 mmols of 2-iminothiolane hydrochloride and 2.5 ml deionized water together in a small vial. Stir rapidly for 5 minutes, and add the entire solution to the room temperature reaction mixture c. Preparation of Conjugate (13)

Add the initiator as follows: dissolve 0.7 mmols of 4,4'-azobis-(4-cyanovaleric acid) (VASO 68) in 2 mls tetrahydrofuran. Once dissolved, add 1 ml of the initiator solution to the reaction mixture at room temperature. After a few minutes remove the nitrogen outlet but maintain the nitrogen inlet connection to prevent pressure build up in the flask.

Move the Schlenk flask to the oil bath, and maintain the temperature at 60° C. for 60 minutes. Refluxing of the solvent inside the flask will occur. After the hour remove from heat, and transfer the polymer solution to a round bottom flask. Remove all solvent via rotary evaporation, and then use high vacuum to further dry the sample.

Once dry dissolve the polymer in 40 ml of deionized water and bring the pH of the solution up to 8.0 by using 50% sodium hydroxide. Precipitate the polymer by adding 4 parts acetone to 1 part polymer solution. Mix vigorously and centrifuge at 4500×g for 5 minutes. The first precipitation gives an oil, not a solid, care is needed for decanting the acetone. The resulting oil is washed twice more with acetone to obtain a gummy solid and mechanical stirring. Remove trace acetone by washing/precipitating the polymer twice with diethyl ether. After the final decantation of diethyl ether, use vacuum to remove residual solvent from the conjugate (13) to obtain a dry powder.

Reaction of conjugate (13) with a saccharide to provide conjugate (5), conversion of the acetal group to the aldehyde (6), synthesis of MSC2-insulin, gel formation and elution properties of the insulin-containing conjugate (8 and 9), and in vivo bioactivity of this material (8 and 9) are performed as previously presented in Example 1.

Example 3

Conjugates with Non-Human Insulin, Insulin Analogues, Etc.

Conjugates of formula (III) that include non-human insulin or insulin analogues (i.e., peptides with insulin like bioactivity that differ from insulin by one or more substitutions, additions or deletions) are prepared according to the methods of Example 1 and 2 using non-human insulin or insulin analogues instead of insulin.

Example 4

Conjugates with Symlin

The peptidic anti-diabetic drug symlin (pramlintide acetate) is derived from the natural peptide amylin. It can also be included in conjugates of formula (III) using the methods of Example 1 or 2.

Example 5

Conjugates with Peptidic Insulin Secretagogues

Peptidic insulin secretagogues (e.g., GLP-1 or the GLP-1 analogue exanitide) or sulfonylureas (SU), such as glibenclamide are incorporated into a conjugate of formula (III) using the methods of Example 1 or 2.

Example 6

Conjugates with rHGH

The peptidic drug recombinant human growth hormone (rHGH) is included in conjugates of formula (III) using the methods of Example 1 or 2.

Example 7

Conjugates with Glucagon

The peptidic drug glucagon is included in conjugates of formula (III) using the methods of Example 1 or 2.

II. In Vitro Assays of Exemplary Conjugates

This second set of examples provides some comparative in vitro assays that were performed to test the physicochemical properties of insulin-glycogen conjugates.

Example 8

Synthesis of Insulin-Glycogen Conjugates

This example describes the synthesis of an insulin-glycogen conjugate according to U.S. Patent Application Publication No. 20070099820. Briefly, 1 gm of commercially available, unpurified oyster glycogen (Type II, Sigma-Aldrich, St. Louis, Mo.) is dissolved in deionized water at a concentration of 10 mg/ml. Solid CNBr is added to the resulting solution at a CNBr to glycogen mass ratio of 0.68 and the pH maintained constant at 10.7+/−0.2 using 3N sodium hydroxide (NaOH) solution. After stirring for 15 minutes, another equal mass of solid CNBr equal is added and the pH maintained constant at 10.7+/−0.2 while stirring for 45 minutes. Insulin is then added to the solution at an insulin to glycogen mass ratio of 0.60 and the pH adjusted to 9.15 using solid sodium bicarbonate. The solution is stirred overnight, ultrafiltered exhaustively against deionized water using a 50 kDa MWCO polyethersulfone disc membrane filter (Millipore, Bedford, Mass.), and lyophilized. The resulting powder is then purified from unconjugated insulin by gel filtration HPLC (Waters, Milford, Mass.) using a 1 M acetic acid mobile phase over a Superdex™ 30 HiLoad 16/60 (Amersham Biosciences, Piscataway, N.J.) packed column. The insulin glycogen fraction is then lyophilized to obtain the conjugate as a pure white powder. The resulting purified material contained 1.0 wt % of insulin per insulin-glycogen conjugate as measured using amino acid analysis (UCLA Biopolymers Laboratory, Los Angeles, Calif.).

Example 9

Liquid Chromatography Analysis

This example describes the RP-HPLC profile of the insulin-glycogen conjugate synthesized according to Example 8. 100 ul of a 5 mg/ml solution of the insulin-glycogen conjugate was injected onto a Waters Symmetry C8 5 um column (4.6 mm×250 mm), equilibrated with a 80% Water/20% Acetonitrile (CH3CN) mobile phase (each containing 0.1% TFA). The sample was eluted at 1.0 ml/minutes using the following gradient method: 0-5 minutes—constant 80% Water/20% CH3CN, 5-35 minutes—linear gradient to 50% Water/50% CH3CN. The elution profile (data not shown) was broad and heterogenous, indicating a broad distribution of different chemical and/or molecular weight entitites.

Example 10

Molecular Weight Distribution Analysis

This example describes the MW distribution of the insulin-glycogen conjugate synthesized according to Example 8. The MW distribution was determined by injecting 1 ml of a 25 mg/ml solution in pH 7 HEPES buffered saline onto an Ultrahydrogel Size Exclusion Column (Waters Corporation, Millford, Mass.) equilibrated with HEPES buffered saline. The column was eluted over the course of 30 minutes at 0.5 ml per min, and the elution profile was measured as an absorbance at 280 nm. In separate experiments using the same protocol, dextran MW standards (Sigma-Aldrich, St. Louis, Mo.) were injected to establish a calibration curve of MW versus retention time. Based on the calibration curve and the elution profile of the insulin-glycogen conjugate, the average MW was determined to be 500,000 Da with 67% of the distribution eluting over the broad range of 250,000 to 1,000,000 Da (data not shown).

III. In Vivo Assays of Exemplary Conjugates

This third set of examples provides some comparative in vivo assays that were performed to test the bioactivity of insulin-dextran and insulin-glycogen conjugates.

Example 11

Bioactivity of Dextran and Glycogen Conjugates a. Insulin-Dextran Bioactivity This comparative example evaluates the in vivo pharmacodynamic profile of subcutaneously administered insulin-dextran (Sigma-Aldrich, MW ~70K). As shown below, the insulin-dextran conjugates synthesized according to U.S.

Patent Publication No. 20040202719 act relatively slowly after subcutaneous injection, because the high MW of the conjugate polymer significantly hinders the absorption rate into systemic circulation. Insulin-dextran was synthesized using a modified cyanogen bromide (CNBr) coupling reaction. Briefly, 500 mg of dextran (MW=70K, Sigma-Aldrich) was dissolved in 50 ml of deionized water. 56 mg of solid CNBr was added to the resulting solution and the pH was maintained at 10.7±0.2 using 5 N NaOH solution. After stirring for 15 min, another 56 mg of solid CNBr was added and the pH was maintained at 10.7±0.2 while stirring for 45 minutes. 300 mg of recombinant human insulin (RHI) was then added to the solution, and the pH was adjusted to 9.15 using solid sodium bicarbonate. The solution was stirred overnight, ultrafiltered exhaustively against DI water using a 10K MWCO polyethersulfone disc membrane filter (Millipore, Bedford, Mass.), and lyophilized. The resulting powder was then purified from unconjugated insulin by high performance liquid chromatography (Waters, Milford, Mass.) using a 1 M acetic acid mobile phase over a Superdex™ 75 packed column (Amersham Biosciences, Piscataway, N.J.). The insulin-dextran fraction was then lyophilized to obtain the conjugate as a pure powder. The degree of insulin conjugation was 10% (w/w) as determined by amino acid analysis (UCLA Biopolymers Laboratory, Los Angeles, Calif.).

Figure 5:
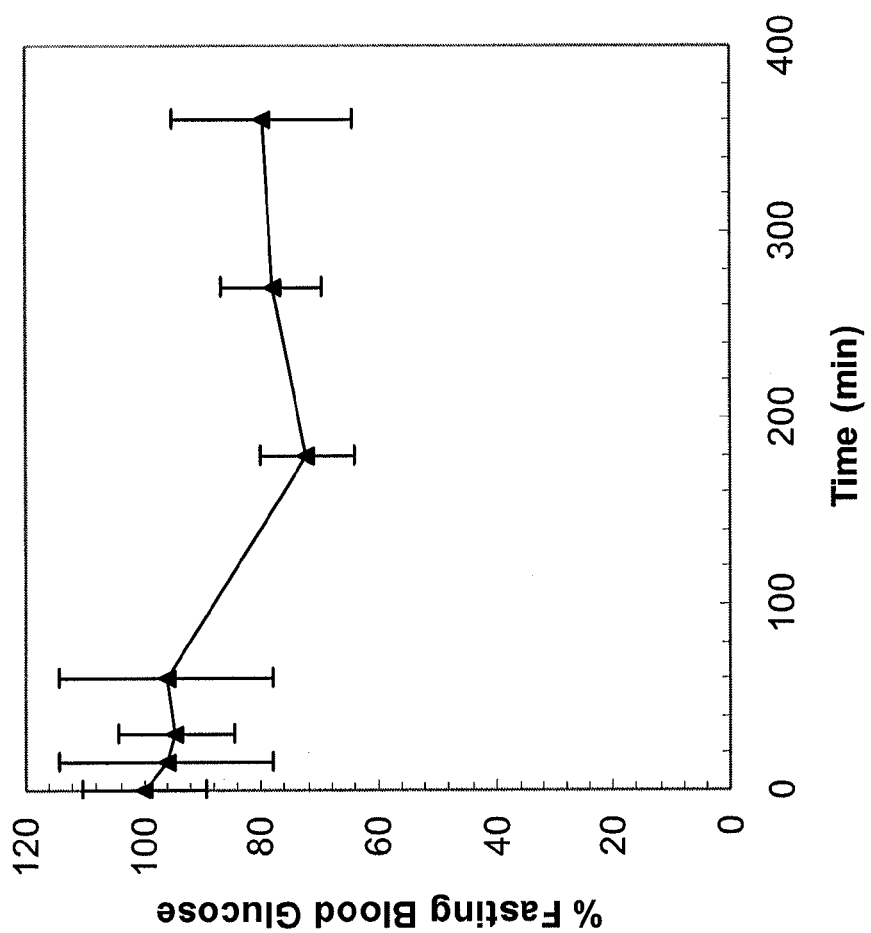
FIG. 5: shows the blood glucose depression profile in non-diabetic, male SD rats (n=3) for subcutaneously injected (▲) insulin-dextran (70 K) at a dose of ~20 U of insulin equivalents/kg.

Subcutaneous injections of the insulin-dextran were administered using 0.25 ml of a sterilized 1×PBS solution (20 U of equivalent insulin/ml) behind the neck of fasted normal non-diabetic rats (Male Sprague-Dawley, 200-250 g, n=4). Blood samples were collected via tail vein bleeding at −15 and 0 minutes, and at 15, 30, 45, 60, 90, 120, 180, 240, 300 and 360 minutes after injection. Blood glucose values were measured using commercially available test strips (Precision Xtra, Abbott Laboratories, Abbott Park, Ill.). As shown in FIG. 5, the times to reach the glucose nadir ($T_{nadir}$) concentration was found to be about 3 hours after injection, and the serum glucose levels remain depressed for at least five hours post injection.

b. Insulin-Glycogen Bioactivity

Figure 6:
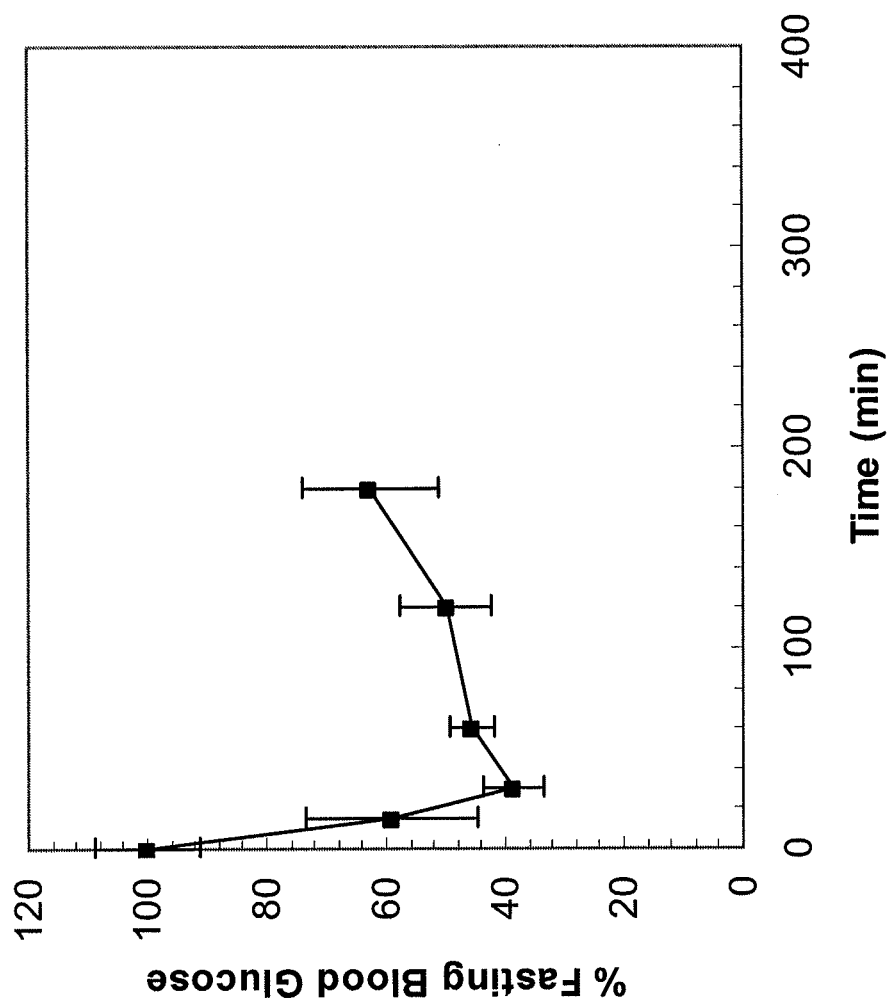
FIG. 6: shows the blood glucose depression profile in non-diabetic, male SD rats (n=3) for subcutaneously injected (■) insulin-glycogen (Type II oyster) at a dose of ~2.5 U of insulin equivalents/kg.

This example evaluates the in vivo pharmacodynamic profile of subcutaneously administered insulin-glycogen. The insulin-glycogen conjugate was synthesized according to Example 8. The bioactivity of the insulin-glycogen conjugate was evaluated by injecting a 2.5 equivalent U of insulin/kg dose behind the neck of fasted normal non-diabetic rats (Male Sprague-Dawley, 200-250 g, n=4). Blood samples were collected via tail vein bleeding at −15 and 0 minutes, and at 15, 30, 45, 60, 90, 120, 180, 240, 300 and 360 minutes after injection. Blood glucose values were measured using commercially available test strips (Precision Xtra, Abbott Laboratories, Abbott Park, Ill.). As compared to the insulin-dextran conjugates above, the high MW insulin-glycogen conjugates lower glucose levels much more rapidly and to a greater extent (see FIG. 6). This rapid action and elimination profile is due to the rapid enzymatic digestion of the high MW glycogen polymer chain following subcutaneous injection.

IV. Binding-Site Modified Lectins

This fourth set of examples describes the preparation and testing of a variety of binding-site modified lectins.

Example 12

Synthesis of Azidophenyl-Sugar Modified Con A

All steps were performed at room temperature unless otherwise specified. First, 5.0 g of native Con A (Sigma-Aldrich, St. Louis, Mo.) was dissolved in 200 ml of a 10 mM pH 5.0 acetate buffer solution containing 150 mM sodium chloride, 2 mM calcium chloride, 2 mM manganese chloride, and 0.1% w/v sodium azide (S28 buffer) and any insoluble material was separated by centrifugation and/or filtration. We have found that different commercial preparations of native Con A contain appreciable concentrations of inhibitory sugars that are, in certain embodiments, removed prior to photoaffinity modification. To that end, the solution was purified through a Biogel-P6 size exclusion column with an S28 mobile phase two times. Finally, the resulting solution was diluted with S28 to a final volume of 1 L. Under gentle stirring conditions, 0.4 g of hydroquinone (Sigma-Aldrich, St. Louis, Mo.) was added followed by 165 mg of either azidophenylglucose (APG, PolyOrg Inc., Leominster, Mass.) or azidophenylmannose (APM, PolyOrg Inc., Leominster, Mass.). The solution was stirred in the dark at 4 C for one hour at the lowest possible stir speed. After one hour of stirring, any additional insoluble material was removed via centrifugation and/or filtration. 200 ml of the solution was poured into a 9"×13" aluminum pan and reacted at 4 C inside a CL-1000 UV crosslinking oven (UVP, Upland, Calif.) for 15 min at 360 nm (the UV reaction may also take place using 302 nm light). Following the reaction, any additional insoluble material was removed via centrifugation and/or filtration. The clarified solution was then purified 1× through Biogel-P6 size exclusion columns (Econopak, Bio-Rad Labs, Hercules, Calif.) with an S28 mobile phase. The UV crosslinking reaction and P6 purification process was then repeated until the entire solution was reacted. Finally, the combined P6-purified solutions were concentrated down to ~180 ml using a Pall tangential flow filtration cartridge apparatus (Millipore, Billerica, Mass.) equipped with Omega 30K membranes. The resulting solution was clarified via centrifugation and/or filtration and passed through 0.22 um filters prior to affinity column purification.

Example 13

Generalized Synthesis of Diazirine Photoreactive Ligands 0.9 mmol of aminoethyl (AE) functionalized sugar ligand (e.g., AEG, AEM, AEBM, AETM) were dissolved in 4 ml of anhydrous DMSO after which 1.6 ml of anhydrous triethylamine (TEA) were added to form a cloudy emulsion. In a separate container, 200 mg (0.9 mmol) of NHS-diazirine (Thermo Fisher Scientific Inc., Rockford, Ill.) powder was dissolved in 4 ml of anhydrous DMSO under dark conditions. Once dissolved, the NHS-diazirine solution was added dropwise to the AE-sugar solution and then allowed to react overnight at room temperature in the dark. TLC analysis (50% ethanol:50% ethyl acetate) of the overnight solution confirmed complete reaction as evidenced by the co-elution of the UV signal of the diazirine moiety (254 nm) and the sugar signal (sulfuric acid-ethanol stain) and concomitant disappearance of the AE-functionalized sugar ligand from the origin of the TLC (sulfuric acid-ethanol stain). The solution was then diluted into 80 ml of a pH 5.0, 25 mM HEPES solution containing 0.15 M sodium chloride, pH adjusted to pH 5 if necessary, and then frozen until required for photoaffinity reaction with Con A.

Example 14

Synthesis and Characterization of Sugar-Functionalized Diazirine Con A

All steps were performed at room temperature unless otherwise specified. First, 5.0 g of native Con A (Sigma-Aldrich, St. Louis, Mo.) was dissolved in 200 ml of a 10 mM pH 5.0 acetate buffer solution containing 150 mM sodium chloride, 2 mM calcium chloride, 2 mM manganese chloride, and 0.1% w/v sodium azide (S28 buffer) and any insoluble material were separated by centrifugation and/or filtration. We have found that different commercial preparations of native Con A contain appreciable concentrations of inhibitory sugars that are, in certain embodiments, removed prior to photoaffinity modification. To that end, the solution was purified through a Biogel-P6 size exclusion column with an S28 mobile phase two times. Finally, the resulting solution was diluted with S28 to a final volume of 1 L. Next, the solution volume was brought up to 1 L-⅓ ligand volume, using 1×S28 and poured into a 1 L media bottle with stir bar. Under gentle stirring conditions in the dark, 0.4 g of hydroquinone (Sigma-Aldrich, St. Louis, Mo.) was dissolved. Next, 33 ml of the diazirine-sugar conjugate obtained in Example 43 was added in 7 aliquots under gentle stirring conditions in the dark. Once dissolved, the entire solution was incubated under gentle stirring for an additional 10 min at 4 C in the dark. After 10 min of stirring, any additional insoluble material was removed via centrifugation and/or filtration. 250 ml of the solution was poured into a 9"×13" aluminum pan and reacted at 4 C inside a CL-1000 UV crosslinking oven (UVP, Upland, Calif.) for 15 min at 360 nm. Following the reaction, any additional insoluble material was removed via centrifugation and/or filtration. The clarified solution was then purified 1× through Biogel-P6 size exclusion columns (Econopak, Bio-Rad Labs, Hercules, Calif.) with an S28 mobile phase. The UV crosslinking reaction and P6 purification process was then repeated until the entire solution was reacted. Finally, the combined P6-purified solutions were concentrated down to ~180 ml using a Pall tangential flow filtration cartridge apparatus (Millipore, Billerica, Mass.) equipped with Omega 30K membranes. The resulting solution was clarified via centrifugation and/or filtration and passed through 0.22 um filters prior to affinity column purification.

Example 15

Affinity Column Purification of Modified Con A Samples

Photoaffinity modified lectins synthesized according to Examples 12 and 14 were purified via affinity column chromatography to separate fully reacted material from unreacted and/or partially reacted material. 100-200 ml of solution was injected onto a XK50/100 column (50 mm diameter×100 cm length) packed with glucose-containing Superdex 30 beads (GE Healthcare Life Sciences, UK) equilibrated with S28 buffer. The column was then eluted for 4 hours at 5 ml/min with S28. The desired fraction, having been fully reacted, eluted first from the column followed by partially reacted material which still had a partial affinity for the glucose-containing stationary phase. Typically, material eluting from 70-120 min was collected and the rest discarded. The column was then washed at 5 ml/min with S28 buffer containing 80 mM alpha-methyl-mannose solution for six hours to remove any unreacted lectin followed by regeneration in S28 at 5 ml/min for another six hours. The collected fraction was concentrated using Amicon Ultra 30K ultrafiltration membranes (Millipore, Billerica, Mass.) to approximately 100 ml and passed through 0.22 um filters prior to any further affinity column purification steps. The column purification process was repeated a second, third, and fourth time to obtain sufficiently pure material for subsequent studies. After the fourth purification step, the material was concentrated using Amicon Ultra 30K ultrafiltration membranes (Millipore, Billerica, Mass.) to approximately 18 mg/ml as determined by the solution absorbance at 280 nm (A280). This solution was passed through a 0.22 um filter and stored at 4 C until required for future studies.

Example 16

Chemical Characterization of Modified Con A Samples a. SDS-PAGE

Denaturing polyacrylamide gel electrophoresis (PAGE) using sodium dodecyl sulfate (SDS) was performed on the materials to ensure that no adverse proteolytic cleavage occurred as a result of exposure to UV light. Briefly, a 10-15% Tris-HCl pre-made gel (Criterion, Bio-Rad, Hercules, Calif.) and 1× Tris-glycine-SDS buffer (Bio-Rad, Hercules, Calif.) were used to perform the PAGE experiment. A broad-range molecular weight standard (Bio-Rad, Hercules, Calif.) and a 2 mg/ml sample of native concanavlin A lectin (Con A, Type VI, Sigma-Aldrich, St. Louis, Mo.) were also run as controls. 25 uL of each modified lectin or control sample was dissolved in 50 uL of 1× Laemmli Buffer (Bio-Rad, Hercules, Calif.) containing 5 uL of -mercaptoethanol (Fisher Scientific), and the samples were heated in a boiling water bath for approximately 5 minutes. After the samples had cooled to room temperature, 20 uL of each sample was loaded into the wells of the pre-made PAGE gels. The samples were then run at 200 volts for 60 minutes. After the electrophoresis, the gels were fixed in a solution of deionized water:methanol:glacial acetic acid in a volume ratio of 60:30:10 for 30 minutes, followed by two washes in deionized water. Finally, the gels were stained with 1× Bio-Safe Coomassie Blue stain (Bio-Rad, Hercules, Calif.) for 60 minutes. The final gels were imaged with a light table and digital camera to record the stained gel. The stained protein bands were assayed for their molecular weights by comparing against the molecular weight and native Con A control samples. Proteolytic cleavage of the modified lectin samples during exposure to UV light would result in molecular weight bands that appear to be lower MW and distinctly different than those present in the native Con A control.

b. Matrix-Assisted Laser Desorption Ionization (MALDI) Mass Spectroscopy

Those skilled in the art will recognize that MALDI is a well known technique to characterize protein molecular weights. MALDI can be used to characterize the modified lectin subunit MW after conjugation to affinity ligand and subsequent affinity column purification to calculate the extent to which the modified lectin has been covalently linked with affinity ligand.

Modified lectin samples at 2 mg/ml were added to BioSpin 30 columns (Bio-Rad, Hercules, Calif.) that had been previously equilibrated with deionized water. The BioSpin columns were centrifuged for 4 minutes at 1000×g, and the resulting eluent contained modified lectin samples that had been substantially desalted. The samples were frozen on dry ice and shipped for MALDI analysis using a sinnapic acid matrix.

c. Analytical Ultracentrifugation (AUC)

AUC is a technique used to determine the native molecular weight of protein samples as they exist in solution. Since some lectins include quaternary structures (e.g., Con A) it is recommended to uncover the molecular mass of the modified lectins under non denaturing conditions (SDS-PAGE, MALDI).

Modified lectin samples and control native Con A (Type VI, Sigma-Aldrich, St. Louis, Mo.) samples were dissolved at concentrations of 1.0, 0.5, and 0.25 mg/ml in S28 buffer containing 12.5 mM α-D-mannose, and these were placed into the AUC cells of a Beckman XL-I analytical ultracentrifuge (Biophysical Instrumentation Facility, MIT, Cambridge, Mass.) and successively spun at speeds of 10 k, 20 k, 30 k, or 40 k rpm and allowed to equilibrate for multiple hours at each speed. Each cell was scanned at a wavelength of 280 nm, and Winmatch software (Cambridge, Mass.) was used to determine the equilibration times of the AUC cells. The obtained AUC data for each sample was fit using a non-linear least squares analysis using WinNonLin v1.06 (UConn, Rockville, Conn.) to obtain the molecular weight of the sample.

d. Isothermal Calorimetry

Titration calorimetry was performed at 25 C in a Micro-Cal VP-ITC microcalorimeter (Biophysical Instrumentation Facility, MIT, Cambridge, Mass.), using a 1.4 ml (nominal) titration cell. Typical modified lectin concentrations were in the range of 4-6 mg/ml in PBS buffer (10 mM $NaPO_4$ pH 7.2, 150 mM NaCl, 0.2 mM $CaCl_2$). Samples were titrated with 10 mM methyl-α-D-mannopyranoside in the same buffer, using one 2 μl increment initially to clear the syringe, followed by 9 injections of 4 μl, increasing to 8 μl for the 11th to 30th addition, at intervals of 240 sec. Normally, the latter additions showed only background heat of dilution (i.e., total saturation). Data (eliminating the first data point, and any others that were obviously bad) were fit to the single site model using Origins software supplied with the instrument.

e. MAC Assay

Various photoaffinity-labeled lectins such as those synthesized in Examples 12 and 14 and purified according to Example 15 were compared based on their ability to agglutinate cells possessing affinity ligands to which the unmodified lectin is capable of binding. The minimum agglutinating concentrations (MAC) of each composition was determined in V-well microtitre plates using a 2% v/v suspension of formaldehyde-stabilized rabbit erythrocytes according to the procedure of Crowley et al., Methods. Enzymol. 83:368-373, 1982. Formaldehyde-treated rabbit erythrocytes, prepared by published procedures (Nowak et al., Biochim. Biophys. Acta 393:115-123, 1975), from rabbit blood obtained from University of Michigan Unit for Laboratory Animal Medicine, were available from previous studies. The MAC was defined as the lectin protein concentration (exclusive of attached chemical compounds) in the highest dilution showing visible agglutination.

Briefly, an aqueous solution of a lectin composition was added to the wells of a 96-well plate using dilutions so that the lectin concentration spanned from about 0.1 to 1000 ug/ml. An aliquot of the formaldehyde-treated Rabbit erythrocytes was then pipetted into each well. At low lectin concentrations, there was insufficient lectin to form a network of crosslinked cells and the cells dropped to the bottom of the V-well forming what looks like a dark pin-point circle at the bottom of the plate when viewed from above. However, once the lectin concentration reached the minimum agglutination concentration (MAC), the lectin molecules began crosslinking the saccharide receptors on the erythrocyte surfaces, resulting in a network that cannot settle to the bottom of the V-well forming what looks like a large, opaque, diffuse circle when viewed from above. The lowest concentration that produces the large diffuse circle is the MAC value for a particular formulation.

Figure 7:
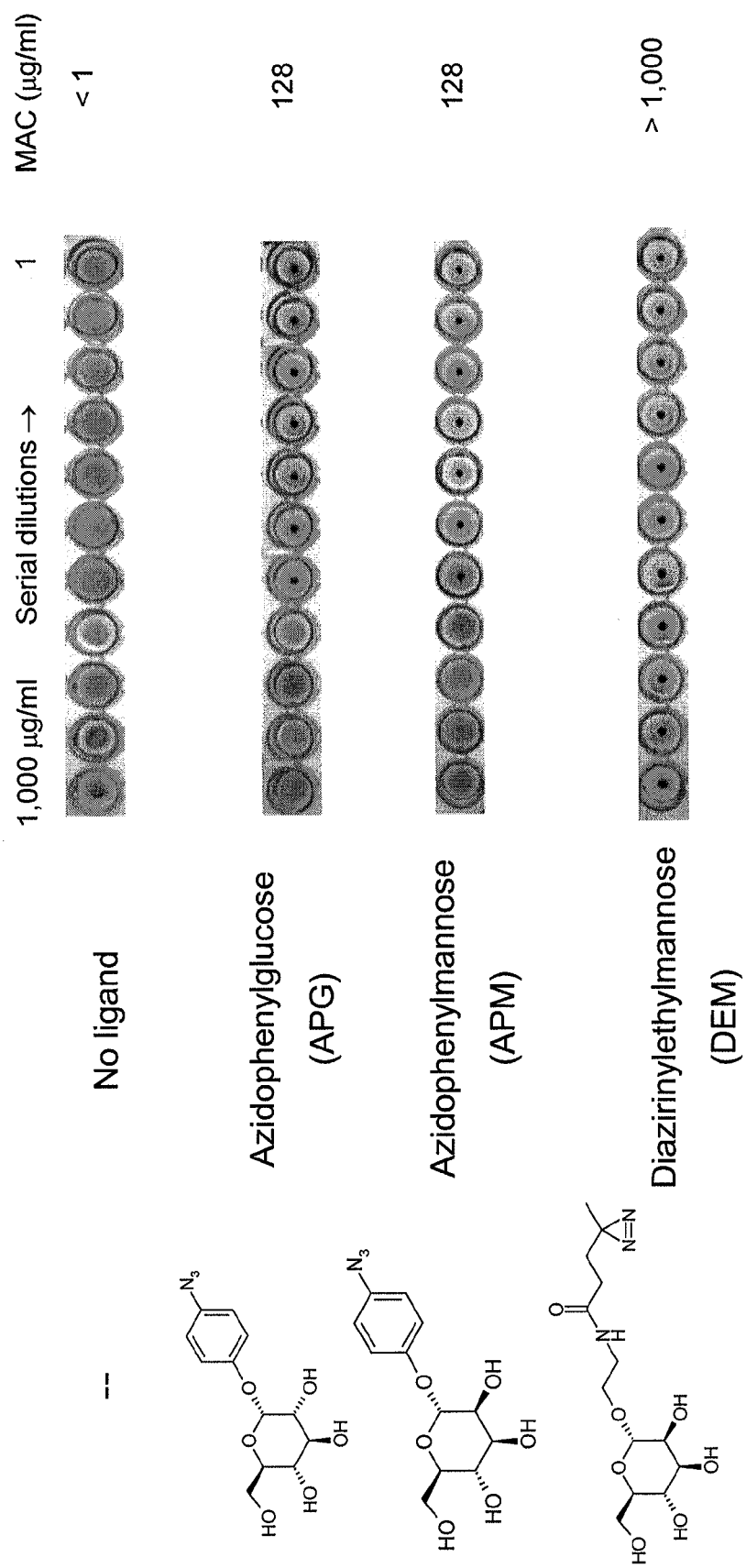
FIG. 7: compares the minimum agglutinating concentrations (MAC) for lectins modified with different affinity ligands.

The following table summarizes the MAC values for Con A-based formulations synthesized according to the examples described above (see also FIG. 7):

| Modified lectin | Affinity ligand type | Synthesis method | MAC (ug/ml) |
|---|---|---|---|
| Unmodified | — | — | <1 |
| APG-Con A | APG | Example 12 | 128 |
| APM-Con A | APM | Example 12 | 128 |
| DEM-Con A | AEM-diazirine | Examples 13-14 | >1,000 |

Example 17

Mitogenicity Assay

This example describes an assay that may be used to characterize and thereby compare the T-cell mitogenicity of different modified lectin compositions. Modifications and alternatives to this typical assay will be apparent to those skilled in the art. Peripheral blood mononuclear cells (PBMCs), rather than highly purified T-cells, are used for this assay since T-cell activation by lectins generally requires the presence of non-T-cell populations collectively termed accessory cells (e.g., monocytes, dendritic cells). In a typical assay, PBMCs are isolated from the whole blood of three healthy human donors and plated out separately at about 100,000 cells per well in a 96 well plate. Triplicate serial dilutions of different lectin compositions (e.g., native and treated) starting at 1000 (or 100) ug/ml concentration are then added to the wells. The plates are incubated for three days at 37 C, at which time 0.8 uCi of $^3$H-thymidine is added to each well for an additional 18 hours. The degree of mitogenicity is then measured by $^3$H-thymidine uptake by the proliferating PBMCs. In some cases, the mitogenicity of a novel lectin composition (e.g., a treated composition) is expressed as the % maximal native mitogenicity. The % maximal native mitogenicity is obtained by dividing the maximal CPM (counts per minute) value for the modified lectin composition over all measured concentrations by the maximal CPM value of the native lectin composition over all measured compositions.

In previous studies we have found a strong correlation between the MAC value and % Con A maximal mitogenicity, i.e., a significant increase in MAC value leads to a significant decrease in mitogenic effect. Therefore, MAC value is used in the present disclosure as a surrogate for determining potential reductions in mitogenicity for a given chemical modification.

V. Cross-Linked Materials for Controllably Releasing a Conjugate

This fifth set of examples describes the preparation of exemplary cross-linked materials for controllable releasing conjugates. A comparative example obtained using a material prepared with an insulin-glycogen conjugate is also included.

Example 18

Cross-Linked Materials Prepared from Modified Con A

An aqueous solution of the chemically modified Concanavalin A of Example 14 is added to an aqueous solution of the insulin conjugate of Example 1. At the proper ratio of both components, an insoluble cross-linked material is formed between the insulin conjugate and lectin. This cross-linked material could be formed over several lectin:polymer mass ratios, but often maximum formation will occur between 1:2 through 8:1 lectin:conjugate mass ratios. The cross-linked material dissolves when the concentration of glucose is increased. Addition of an aqueous buffer not containing a high concentration of a glucose causes no discernible dissolution of the cross-linked material.

Example 19

IPGTT Experiments in Non-Diabetic Rats 0.300 ml of a cross-linked material of Example 18 is injected subcutaneously into each of three normal male Sprague Dawley (SD) rats (Charles River Laboratories, location) weighing between 400 and 500 g. Prior to formulation injection, blood glucose values are measured via tail vein bleeding using a Precision Xtra glucometer (Abbott Laboratories, Alameda, Calif.) and approximately 100 ul of serum is obtained via tail vein bleeding to assay for background insulin levels. Food is removed from the rat cages during the duration of the study. Serum and blood glucose values are obtained at 30 min, 60 min, 90 min, and 120 min post-injection. At 120 min after the injection, an intraperitoneal injection of a 38% w/v glucose solution is injected to provide a 4 g/kg dose after which serum and blood glucose values are obtained at 135 min, 150 min, 180 min, 210 min, 240 min, and 300 min. Serum insulin concentrations are subsequently measured with a commercially available ELISA kit (Human Insulin ELISA, Mercodia, Uppsala, Sweden) using a standard curve generated from the pure insulin conjugate solution.

Example 20

Effect of Different Animal Sera on Glucose-Responsive Dissolution of Insulin-Glycogen Cross-Linked Materials and Correlation to Amylase Activity This example describes the in vitro dissolution in various animal sera as a function of glucose concentration for glucose-responsive formulations synthesized using an insulin-glycogen based conjugate. The insulin-glycogen conjugate was synthesized according to the following procedure. First, 62.5 ml of a 10 mg/ml recombinant human insulin solution (RHI) in pH 8.2, 25 mM HEPES buffer (Sigma-Aldrich, St. Louis, Mass.) was adjusted to pH 9.0 and cooled on ice to produce the RHI stock solution. Separately, 0.312 ml of triethylamine (TEA, Sigma-Aldrich, St. Louis, Mass.) was dissolved in 3 ml of DI water to produce the TEA stock solution. Separately, 0.300 g of cyanodimethylamino pyridinium tetrafluoroborate (CDAP, Sigma-Aldrich, St. Louis, Mo.) was dissolved in 1.2 ml of DMSO to produce the CDAP Stock solution. Separately, 100 mg of mannosamine-HCl (Sigma-Aldrich, St. Louis, Mo.) was dissolved in 1.5 ml of a 100 mM pH 9 HEPES saline buffered saline solution and pH adjusted to 9.0 to produce the mannosamine stock solution. Separately, 2.0 g of oyster Type IX glycogen (Sigma-Aldrich, St. Louis, Mo.) was dissolved in 40 ml of a 100 mM pH 9 HEPES saline buffered saline solution after which the solution was clarified by filtration and cooled on an ice bath. Next, 1 ml of the CDAP stock solution was added to the glycogen solution and mixed for one minute after which 1 ml of the TEA solution was added and the pH of the resulting solution adjusted to 9.0. After an additional 1 minute of stirring, 62 ml of the RHI solution were added and the resulting solution stirred for five minutes followed by addition of 1.065 ml of the mannosamine solution. The solution was stirred overnight at room temperature, ultrafiltered exhaustively against deionized water using a 50 kDa MWCO polyethersulfone disc membrane filter (Millipore, Bedford, Mass.), and lyophilized. The resulting powder was then purified 3× from unconjugated insulin by gel filtration HPLC (Waters, Milford, Mass.) using a 1 M acetic acid mobile phase over a Superdex™30 HiLoad 16/60 (Amersham Biosciences, Piscataway, N.J.) packed column. The insulin glycogen fraction was then lyophilized to obtain the conjugate as a pure white powder.

Twenty-four glucose-responsive formulations were prepared using acetylated Con A (ACA) as the multivalent crosslinking agent in the following manner. 200 ul of a 25 mg/ml insulin-glycogen conjugate solution in pH 7.0 HEPES buffered saline was mixed with 200 ul of a 25 mg/ml chemically-modified, acetylated Con A (ACA) solution in pH 7.0 HEPES buffered saline and allowed to stand for 20 minutes. Next, each formulation was centrifuged and washed 5× at room temperature with 400 ul of pH 7.0 HEPES buffered saline. After the last wash and centrifugation, the supernatant was discarded and the remaining insoluble material dispersed in 50 ul of 1×PBS.

The 24×50 ul dispersions were added to a 96-well plate along with 50 ul of serum from a particular animal species containing a specific amount of glucose according to the following format:

| Insulin-glycogen/ACA cross-linked material | Species sera | | | |
|---|---|---|---|---|
| Glucose Concentration (mg/dl) | pH 7, 1x PBS | Rat | Pig | Human |
| 0 | 1 | 7 | 13 | 19 |
| 50 | 2 | 8 | 14 | 20 |
| 100 | 3 | 9 | 15 | 21 |
| 200 | 4 | 10 | 16 | 22 |
| 400 | 5 | 11 | 17 | 23 |
| 800 | 6 | 12 | 18 | 24 |

At the start of the experiment each well appeared white and opaque (as measured by a decrease in light transmission or increase in absorbance at 450 nm, A450). The 96-well plate was then incubated for 6 hours at 37 C after which the A450 value for each well was measured again. The % of the formulation remaining was calculated by dividing the A450 (final) by the A450 (initial) and multiplying by 100. If all the material had dissolved, the A450 value was close to zero indicating almost 0% remaining. Alternatively, if no material had dissolved, the A450 was close to the initial value indicating almost 100% remaining.

Figure 8:
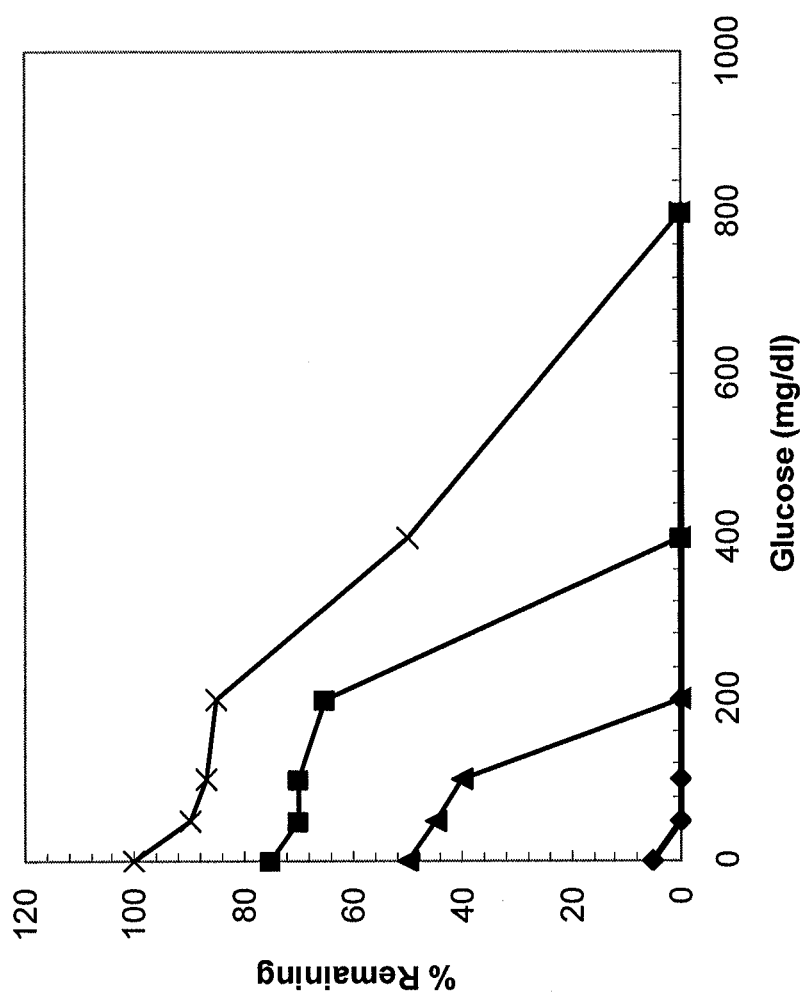
FIG. 8: shows the amounts of glucose-responsive, insulin-glycogen-based material remaining insoluble as a function of glucose concentration after six hours of incubation at 37° C. in the presence of (♦) porcine serum, (■) human serum, (▲) rat serum, and (x) 1×PBS buffer.

The results in FIG. 8 show that the cross-linked materials constructed from insulin-glycogen conjugates dissolve in an ideal glucose responsive manner over the six hour study when incubated in buffered saline. However, the materials dissolve completely regardless of the glucose concentration when incubated in pig serum. Rat serum maintains some glucose responsiveness but dissolves significantly over six hours even in the absence of glucose. Over 20% of the material incubated in human serum still dissolves in the absence of glucose.

Figure 9:
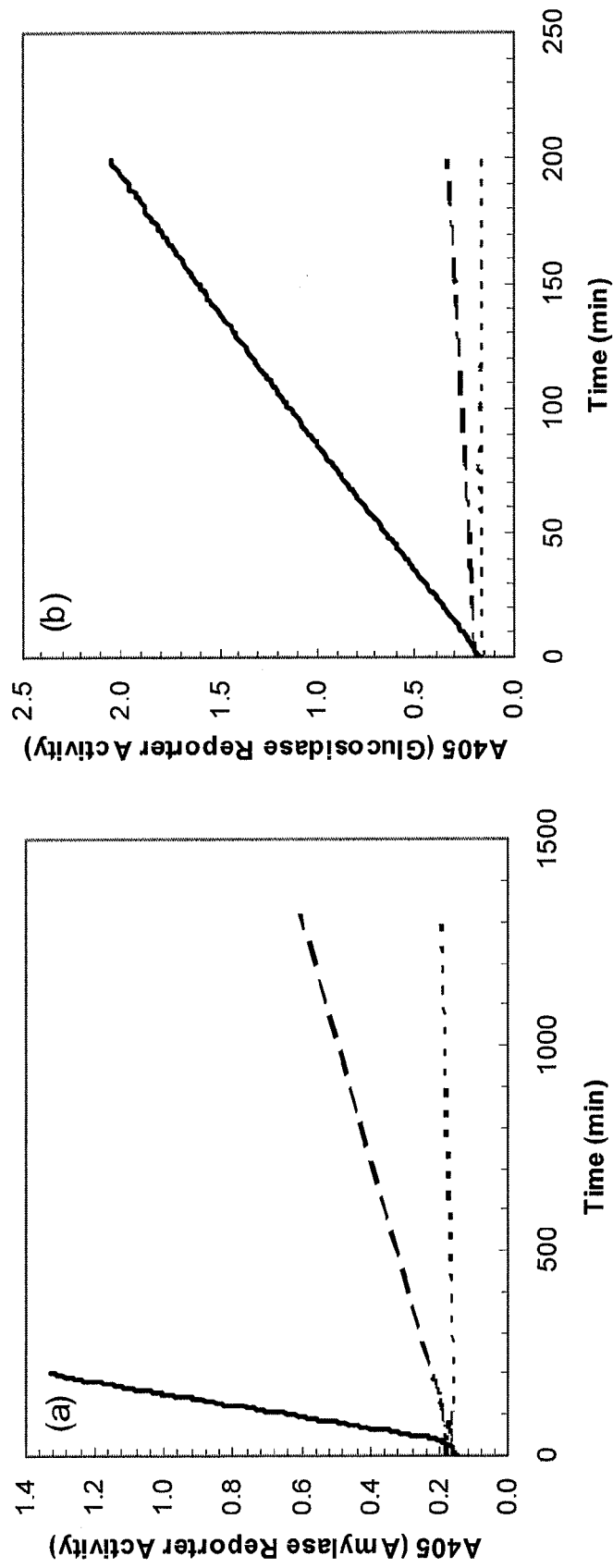
FIG. 9: shows the digestion activity of 1:8 dilutions of porcine (solid line), rat (long dash line), and human (short dash line) serum in PBS as measured by production of colorimetric signal (A405) for (a) amylase activity (4-Nitrophenyl α-D-penta-(1→4)-glucopyranoside reporter) and (b) glucosidase activity (4-Nitrophenyl α-D-glucopyranoside reporter).

These differences were correlated to each species' intrinsic amylase and glucosidase digestion activity by first developing a microplate assay that takes advantage of the production of a colorimetric signal from oligosaccharides connected through linear α-1,4 glycosidic bonds like glycogen. To investigate amylase activity, 4-Nitrophenyl α-D-penta-(1→4)-glucopyranoside (Sigma Aldrich, St. Louis, Mo.) was used, and 4-Nitrophenyl α-D-glucopyranoside (Sigma Aldrich, St. Louis, Mo.) was used to investigate glucosidase activity. For each assay, serum from a particular species was diluted by increasing amounts with 1×PBS and a known concentration of colorimetric reporter was spiked into the solution after which the absorbance signal at 405 nm (A405) was measured as a function of time. FIGS. 9a and 9b illustrate the A405 production due to enzyme activity in each of the different species of serum tested for amylase and glucosidase activity, respectively. Here we see that at a 1:8 dilution of serum in PBS, porcine serum exhibits approximately 17× the digestion activity of rat serum. Furthermore, there appears to be almost no activity whatsoever in the human serum tested under these conditions. Therefore, the differences in the material dissolution profiles in each species' serum appear to be directly correlated with the ability for that species' serum to digest the underlying glycogen conjugate. Taken together, these results provided the impetus for designing bioactive conjugates such as the ones described in this disclosure to circumvent the glycogen-digestion limitation but still form glucose-responsive materials.

OTHER EMBODIMENTS

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

We claim:

1. A conjugate having a formula selected from the group consisting of:

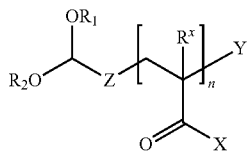

wherein:

$R_1$ and $R_2$ are independently selected from the group consisting of optionally substituted aliphatic, optionally substituted heteroaliphatic, optionally substituted aryl, or optionally substituted heteroaryl;

$R^x$ is hydrogen or optionally substituted $C_{1-6}$ alkyl;

Z is an optionally substituted bivalent $C_{1-10}$ hydrocarbon chain, wherein 1, 2, 3, 4 or 5 methylene units of Z are optionally and independently replaced with one or more groups selected from —S—, —O—, —NR$^a$—, —(C=NR$^a$)—, —(C=O)—, —(S=O)—, —S(=O)$_2$—, —(CR$^b$=CR$^b$)—, —(N=N)—, an optionally substituted arylene moiety or an optionally substituted heteroarylene moiety, wherein R$^a$ is hydrogen, optionally substituted aliphatic, optionally substituted heteroaliphatic, optionally substituted aryl, optionally substituted heteroaryl, or a suitable amino protecting group; and R$^b$ is hydrogen, optionally substituted aliphatic, optionally substituted heteroaliphatic, optionally substituted aryl, optionally substituted heteroaryl;

each instance of X is independently —OR$^c$ or —N(R$^d$)$_2$, wherein R$^c$ is hydrogen, optionally substituted aliphatic, optionally substituted heteroaliphatic, optionally substituted aryl, optionally substituted heteroaryl, a suitable hydroxyl protecting group, a cation group, or an affinity ligand, and each R$^d$ is, independently, hydrogen, optionally substituted aliphatic, optionally substituted heteroaliphatic, optionally substituted aryl, optionally substituted heteroaryl, a suitable amino protecting group, or an affinity ligand, wherein at least two occurrences of X include an affinity ligand selected from aminoethylglucose (AEG), aminoethylmannose (AEM), aminoethylbimannose (AEBM) and aminoethyltrimannose (AETM);

Y is hydrogen, halogen, optionally substituted aliphatic, optionally substituted heteroaliphatic, optionally substituted aryl, optionally substituted heteroaryl, —OR$^e$ or —SR$^e$ wherein R$^e$ is hydrogen, optionally substituted aliphatic, optionally substituted heteroaliphatic, optionally substituted aryl, or optionally substituted heteroaryl; and n is an integer between 5-25, inclusive;

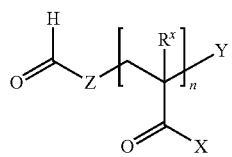

wherein:

$R^x$ is hydrogen or optionally substituted $C_{1-6}$ alkyl;

Z is an optionally substituted bivalent $C_{1-10}$ hydrocarbon chain, wherein 1, 2, 3, 4 or 5 methylene units of Z are optionally and independently replaced with one or more groups selected from —S—, —O—, —NR$^a$—, —(C=NR$^a$)—, —(C=O)—, —(S=O)—, —S(=O)$_2$—, —(CR$^b$=CR$^b$)—, —(N=N)—, an optionally substituted arylene moiety or an optionally substituted heteroarylene moiety, wherein $R^a$ is hydrogen, optionally substituted aliphatic, optionally substituted heteroaliphatic, optionally substituted aryl, optionally substituted heteroaryl, or a suitable amino protecting group; and $R^b$ is hydrogen, optionally substituted aliphatic, optionally substituted heteroaliphatic, optionally substituted aryl, optionally substituted heteroaryl;

each instance of X is independently —OR$^c$ or —N(R$^d$)$_2$, wherein R$^c$ is hydrogen, optionally substituted aliphatic, optionally substituted heteroaliphatic, optionally substituted aryl, optionally substituted heteroaryl, a suitable hydroxyl protecting group, a cation group, or an affinity ligand, and each R$^d$ is, independently, hydrogen, optionally substituted aliphatic, optionally substituted heteroaliphatic, optionally substituted aryl, optionally substituted heteroaryl, a suitable amino protecting group, or an affinity ligand, wherein at least two occurrences of X include an affinity ligand selected from aminoethylglucose (AEG), aminoethylmannose (AEM), aminoethylbimannose (AEBM) and aminoethyltrimannose (AETM);

Y is hydrogen, halogen, optionally substituted aliphatic, optionally substituted heteroaliphatic, optionally substituted aryl, optionally substituted heteroaryl, —OR$^e$ or —SR$^e$ wherein R$^e$ is hydrogen, optionally substituted aliphatic, optionally substituted heteroaliphatic, optionally substituted aryl, or optionally substituted heteroaryl; and n is an integer between 5-25, inclusive; and

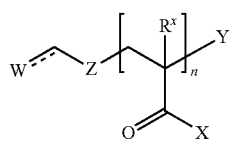
III wherein:

W is a covalently conjugated drug or detectable label;

═════ corresponds to a single or double bond;

$R^x$ is hydrogen or optionally substituted $C_{1-6}$ alkyl;

Z is an optionally substituted bivalent $C_{1-10}$ hydrocarbon chain, wherein 1, 2, 3, 4 or 5 methylene units of Z are optionally and independently replaced with one or more groups selected from —S—, —O—, —NR$^a$—, —(C=NR$^a$)—, —(C=O)—, —(S=O)—, —S(=O)$_2$—, —(CR$^b$=CR$^b$)—, —(N=N)—, an optionally substituted arylene moiety or an optionally substituted heteroarylene moiety, wherein $R^a$ is hydrogen, optionally substituted aliphatic, optionally substituted heteroaliphatic, optionally substituted aryl, optionally substituted heteroaryl, or a suitable amino protecting group; and $R^b$ is hydrogen, optionally substituted aliphatic, optionally substituted heteroaliphatic, optionally substituted aryl, optionally substituted heteroaryl;

each instance of X is independently —OR$^c$ or —N(R$^d$)$_2$, wherein R$^c$ is hydrogen, optionally substituted aliphatic, optionally substituted heteroaliphatic, optionally substituted aryl, optionally substituted heteroaryl, a suitable hydroxyl protecting group, a cation group, or an affinity ligand, and each R$^d$ is, independently, hydrogen, optionally substituted aliphatic, optionally substituted heteroaliphatic, optionally substituted aryl, optionally substituted heteroaryl, a suitable amino protecting group, or an affinity ligand, wherein at least two occurrences of X include an affinity ligand selected from aminoethylglucose (AEG), aminoethylmannose (AEM), aminoethylbimannose (AEBM) and aminoethyltrimannose (AETM);

Y is hydrogen, halogen, optionally substituted aliphatic, optionally substituted heteroaliphatic, optionally substituted aryl, optionally substituted heteroaryl, —OR$^e$ or —SR$^e$ wherein R$^e$ is hydrogen, optionally substituted aliphatic, optionally substituted heteroaliphatic, optionally substituted aryl, or optionally substituted heteroaryl; and n is an integer between 5-25, inclusive.

2. The conjugate of claim 1, wherein the group:

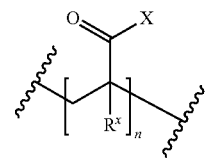

corresponds to a mixture of the groups:

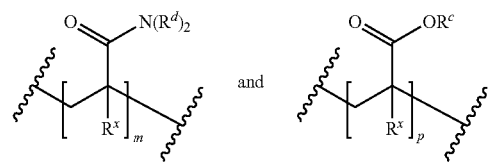

wherein the sum of (m+p) is equal to n.

3. The conjugate of claim 1, wherein W is a covalently conjugated drug.

4. The conjugate of claim 3, wherein the drug is an insulin molecule.

5. A method of preparing a conjugate of Formula I of claim 1, comprising the steps of:
(a) providing a mixture of a catalyst, initiating compound and one or more monomers; and
(b) polymerizing the mixture, wherein:
the initiating compound is of the formula:

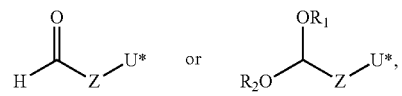

or a mixture thereof, wherein U* is a suitable leaving group; and the monomer(s) is of the formula:

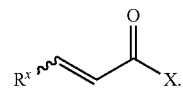

6. A method of preparing a conjugate of Formula I of claim 1, comprising the steps of:
(a) providing a mixture of a free radical initiator and one or more monomers;
(b) polymerizing the mixture; and
(c) terminating the polymerization by adding a chain terminating agent;

wherein:
the monomer(s) is of the formula:

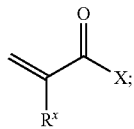

and
the chain terminating agent is a compound of the formulae:

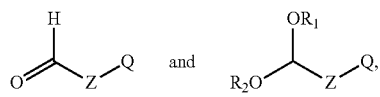

or a mixture thereof, wherein Q is selected from —SH, —OH or —NH$_2$.

7. A cross-linked material comprising:
conjugates of Formula III of claim 1; and
multivalent cross-linking agents that non-covalently bind the affinity ligands of the conjugates and thereby cross-link the conjugates to form a cross-linked material, wherein the non-covalent bonds between the multivalent cross-linking agents and the affinity ligands are competitively dissociated in the presence of excess amounts of a target molecule.

8. The material of claim 7, wherein the target molecule is glucose and the affinity ligands of the conjugates include a saccharide.

9. The material of claim 7, wherein the multivalent cross-linking agent includes a lectin.

10. The material of claim 9, wherein the lectin is chemically modified.

11. The material of claim 7, wherein the multivalent cross-linking agent includes a peptide aptamer.

12. The material of claim 7, wherein the drug is an insulin molecule.

13. A method comprising administering a material of claim 7 to a patient.

* * * * *